US007189559B2

(12) United States Patent
Damude et al.

(10) Patent No.: US 7,189,559 B2

(45) Date of Patent: Mar. 13, 2007

(54) ***MORTIERELLA ALPINA* LYSOPHOSPHATIDIC ACID ACYLTRANSFERASE HOMOLOG FOR ALTERATION OF POLYUNSATURATED FATTY ACIDS AND OIL CONTENT IN OLEAGINOUS ORGANISMS**

(75) Inventors: Howard Glenn Damude, Hockessin, DE (US); Zhixiong Xue, Chadds Ford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/251,466

(22) Filed: Oct. 14, 2005

(65) Prior Publication Data

US 2006/0094090 A1 May 4, 2006

Related U.S. Application Data

(60) Provisional application No. 60/689,031, filed on Jun. 9, 2005, provisional application No. 60/624,812, filed on Nov. 4, 2004.

(51) Int. Cl.

| | |
|---|---|
| ***C12N 1/16*** | (2006.01) |
| ***C12N 9/10*** | (2006.01) |
| ***C12N 15/70*** | (2006.01) |
| ***C12N 15/04*** | (2006.01) |
| ***C12P 21/06*** | (2006.01) |
| ***C07H 21/04*** | (2006.01) |

(52) U.S. Cl. .................. 435/254.2; 435/193; 435/69.1; 435/320.1; 435/483; 536/23.2

(58) Field of Classification Search ................ 435/193, 435/69.1, 254.2, 320.1; 536/23.2

See application file for complete search history.

(56) References Cited

U.S. PATENT DOCUMENTS

2005/0136519 A1 6/2005 Picataggio et al.

FOREIGN PATENT DOCUMENTS

WO WO 2004/087902 A2 10/2004

OTHER PUBLICATIONS

U.S. Appl. No. 10/840,579, filed May 6, 2004, Picataggio et al.

U.S. Appl. No. 60/624,812, filed Nov. 4, 2004, Zhu et al.

U.S. Appl. No. 11/265,761, filed Nov. 2, 2005, Zhu et al.

National Center for Biotechnology Information General Identifier No. 55163909, Accession No. CQ891250, Nov. 1, 2004, A. Renz et al., Novel Plant Acyltransferases Specific for Long-Chained, Multiply Unsaturated Fatty Acids.

National Center for Biotechnology Information General Identifier No. 55163911, Accession No. CQ891252, Nov. 1, 2004, A. Renz et al., Novel Plant Acyltransferases Specific for Long-Chained, Multiply Unsaturated Fatty Acids.

National Center for Biotechnology Information General Identifier No. 3914356, Accession No. Q93841, Feb. 7, 2006, Genome Sequence of the Nematode C. Elegans: A Platform for Investigating Biology.

National Center for Biotechnology Information General Identifier No. 3914366, Accession No. Q22267, Feb. 7, 2006, Genome Sequence of the Nematode C. Elegans: A Platform for Investigating Biology.

National Center for Biotechnology Information General Identifier No. 3914372, Accession No. Q99943, Feb. 7, 2006, J. West et al., Cloning and Expression of Two Human Lysophosphatidic Acid Acyltransferase cDNAS That Enhance Cytokine-Induced Signaling Response in Cells.

National Center for Biotechnology Information General Identifier No. 3914362, Accession No. O15120, Feb. 7, 2006, C. Eberhardt et al., Human Lysophosphatidic Acid Acyltransferase. cDNA Cloning, Expression, and Localization to Chromosome 9Q34.3.

National Center for Biotechnology Information General Identifier No. 12643817, Accession No. Q9NRZ7, Feb. 7, 2006, D. W. Leung.

National Center for Biotechnology Information General Identifier No. 12230468, Accession No. Q9NRZ5, Feb. 7, 2006, D. W. Leung.

National Center for Biotechnology Information General Identifier No. 30923427, Accession No. Q9NUQ2, Feb. 7, 2006, D. W. Leung.

National Center for Biotechnology Information General Identifier No. 3914383, Accession No. O35083, Feb. 7, 2006, K. Kume et al., CDNA Cloning and Expression of Murine.

National Center for Biotechnology Information General Identifier No. 30923346, Accession No. Q9D1E8, Feb. 7, 2006, B. Lu et al.

National Center for Biotechnology Information General Identifier No. 20138810, Accession No. Q924S1, Feb. 7, 2006, W. Li et al.

National Center for Biotechnology Information General Identifier No. 3914378, Accession No. Q59188, Feb. 7, 2006, C. M. Fraser et al. Genomic Sequence of a Lyme Disease Spirochaete, Borrelia Burgdorferi.

National Center for Biotechnology Information General Identifier No. 3914374, Accession No. Q42670, Feb. 7, 2006, D. S. Knutzon et al., Cloning of a Coconut Endosperm cDNA Encoding a 1-Acyl-SN-Glycerol-3-Phosphate Acyltransferase That Accepts Medium-Chain-Length Substrates.

National Center for Biotechnology Information General Identifier No. 130327, Accession No. P26647, Feb. 7, 2006, J. Coleman, Characterization of the *Escherichia coli* Gene for 1-Acyl-SN-Glycerol-3-Phosphate Acyltransferase (PLSC).

(Continued)

*Primary Examiner*—Manujunath N. Rao
*Assistant Examiner*—Iqbal Chowdhury

(57) ABSTRACT

Lysophosphatidic acid acyltransferase (LPAAT) participates in the second step of oil biosynthesis and is expected to play a key role in altering the quantity of long-chain polyunsaturated fatty acids produced in oils of oleaginous organisms. The present application provides a nucleic acid fragment (identified as "LPAAT2") isolated from *Mortierella alpina* encoding a LPAAT homolog that is suitable for use in the manufacture of oils enriched in omega fatty acids in oleaginous organisms. Most desirably, the substrate specificity of the instant LPAAT2 will be particularly useful to enable accumulation of long-chain PUFAs having chain lengths equal to or greater than $C_{20}$ in oleaginous yeast, such as *Yarrowia lipolytica*.

7 Claims, 8 Drawing Sheets

OTHER PUBLICATIONS

National Center for Biotechnology Information General Identifier No. 1172534, Accession No. P44848, May 1, 2005, R. D. Fleischmann et al., Whole-Genome Random Sequencing and Assembly of *Haemophilus influenzae* RD.

National Center for Biotechnology Information General Identifier No. 12230506, Accession No. Q9ZJN8, May 1, 2005, R. A. Alm et al. Genomic-Sequence Comparison of Two Unrelated Isolates of the Human Gastric Pathogen *Helicobacter pylori*.

National Center for Biotechnology Information General Identifier No. 3914373, Accession No. O25903, May 1, 2005, J. -F. Tomb et al., The Complete Genome Sequence of the Gastric Pathogen *Helicobacter pylori*.

National Center for Biotechnology Information General Identifier No. 3914375, Accession No. Q42868, Feb. 7, 2006, M. W. Lassner et al., Lysophosphatidic Acid Acyltransferase from Meadowfoam Mediates Insertion of Erucic Acid at the SN-2 Position of Triacylglycerol in Transgenic Rapeseed Oil.

National Center for Biotechnology Information General Identifier No. 3914376, Accession No. Q42870, Feb. 7, 2006, C. Hanke et al., A Plant Acyltransferase Involved in Triacylglycerol Biosynthesis Complements an *Escherichia coli* SN-1-Acylglycerol-3-Phosphate Acyltransferase Mutant.

National Center for Biotechnology Information General Identifier No. 130329, Accession No. P26974, May 1, 2005, A. L. Luttinger et al., A Cluster of Genes That Affects Nucleoid Segregation in Salmonella Typhimurium.

National Center for Biotechnology Information General Identifier No. 464422, Accession No. Q33333, Feb. 7, 2006, M. M. Nagiec et al., A Suppressor Gene That Enables *Saccharomyces cerevisiae* to Grow Without Making Sphingolipids Encodes a Protein That Resembles an *Escherichia coli* Fatty Acyltransferase.

National Center for Biotechnology Information General Identifier No. 83287830, Accession No. Q9XFW4, Feb. 7, 2006, A. Graefin Zu Muenster et al.

National Center for Biotechnology Information General Identifier No. 55163919, Accession No. CQ891260, Nov. 1, 2004, A. Renz et al., Novel Plant Acyltransferases Specific for Long-Chained, Multiply Unsaturated Fatty Acids.

National Center for Biotechnology Information General Identifier No. 55163917, Accession No. CQ891258, Nov. 1, 2004, A. Renz et al., Novel Plant Acyltransferases Specific for Long-Chained, Multiply Unsaturated Fatty Acids.

National Center for Biotechnology Information General Identifier No. 55163907, Accession No. CQ891248, Nov. 1, 2004, A. Renz et al., Novel Plant Acyltransferases Specific for Long-Chained, Multiply Unsaturated Fatty Acids.

National Center for Biotechnology Information General Identifier No. 55163904, Accession No. CQ891245, Nov. 1, 2004, A. Renz et al., Novel Plant Acyltransferases Specific for Long-Chained, Multiply Unsaturated Fatty Acids.

National Center for Biotechnology Information General Identifier No. 55163900, Accession No. CQ891241, Nov. 1, 2004, A. Renz et al., Novel Plant Acyltransferases Specific for Long-Chained, Multiply Unsaturated Fatty Acids.

National Center for Biotechnology Information General Identifier No. 55163897, Accession No. CQ891238, Nov. 1, 2004, A. Renz et al., Novel Plant Acyltransferases Specific for Long-Chained, Multiply Unsaturated Fatty Acids.

National Center for Biotechnology Information General Identifier No. 55163913, Accession No. CQ891254, Nov. 1, 2004, A. Renz et al., Novel Plant Acyltransferases Specific for Long-Chained, Multiply Unsaturated Fatty Acids.

National Center for Biotechnology Information General Identifier No. 55163894, Accession No. CQ891235, Nov. 1, 2004, A. Renz et al., Novel Plant Acyltransferases Specific for Long-Chained, Multiply Unsaturated Fatty Acids.

National Center for Biotechnology Information General Identifier No. 49649227, Accession No. CR382131, Nov. 9, 2005, B. Dujon et al., Genome Evolution in Yeasts.

National Center for Biotechnology Information General Identifier No. 49646199, Accession No. CR382128, Nov. 9, 2005, B. Dujon et al., Genome Evolution in Yeasts.

```
            1                                                        50
A:    (1) MDESTTTTTHHSETSSKTSSHPRRLGPEMNPIYKGLRAIVWAFYFNLGAS
B:    (1) ---------------------------MNPIYKGLRAIVWAFYFNLGAS
C:    (1) --------------------------MLGSVTRPTKALLYGSALFSFCS

            51                                                       100
A:   (51) LISITQVLSLPLALIAPGVYQWHISKTQGHFGAFLLRMNQLFAPSDIVLT
B:   (23) LISITQVLSLPLALIAPGVYQWHISKTQGHFGAFLLRMNQLFAPSDIVLT
C:   (24) LLNMVQVFSILLQPFSKRLFFEVNARVAGSMWKVMQLIMEKKHKAATFS

            101                                                      150
A:  (101) GDESVRGIVKVYKGRNLKEAGEPGSGQGEDILLDMPERMVFIANHQIYSD
B:   (73) GDESVRGIVKVYKGRNLKEAGEPGSGQGEDILLDMPERMVFIANHQIYSD
C:   (74) GDKIPHHESAIVFG-----------------------------NHRSFVD

            151                                                      200
A:  (151) WMYLWCFSYFAERHRALKIILRGDLTWIPVFGWGMRFFDFIFLKRNDWAH
B:  (123) WMYLWCFSYFAERHRALKIILRGDLTWIPVFGWGMRFFDFIFLKRNDWAH
C:   (95) FYMFHTVAARRGMLNYMKYFAKDSLKYIPFYGWGMWIMGMLFINRNWQQD

            201                                                      250
A:  (201) DRRAIEENLGRVKEKDPLWLVVFPEGTVVSKETRLRSVAFSKKASLSDHR
B:  (173) DRRAIEENLGRVKEKDPLWLVVFPEGTVVSKETRLRSVAFSKKASLSDHR
C:  (145) QLKINKMFARIEDIQAPVWVASFLEGSRLTPSKLAASQKFMLGRGLPLLS
```

FIG. 2A

```
301
350
A: (299)
LYINKAQPKEINMHLRRFAIKDIPTSEPEFVEWVRARWVEKDELMEEFYT
B: (271)
LYINKAQPKEINMHLRRFAIKDIPTSEPEFVEWVRARWVEKDELMEEFYT
C: (245) GQLSPEY--
KFHVHVRRYQLDDLPTDEEKLSEWVVQKYVEKDAFLEQMKE

351
400
A: (349)
KGRFPSQLTAADIGEKEVKTAGGPTEGQSVRIPLKARGMMDYLMPSVMNL
B: (321)
KGRFPSQLTAADIGEKEVKTAGGPTEGQSVRIPLKARGMMDYLMPSVMNL
C: (293) N--WTDGIDGGVWSENWM------------------------------
--

        401                 420
A: (399) IALPVLAFAMRYAVQQASG-
B: (371) IALPVLAFAMRYAVQQASG-
C: (309) --------------------
```

A. GenBank Accession No. CAH68669, corresponding to SEQ ID NO:17 of WO 2004/087902
B. GenBank Accession No. CAH68670, corresponding to SEQ ID NO:19 of WO 2004/087902
C. SEQ ID NO:2

FIG. 2B

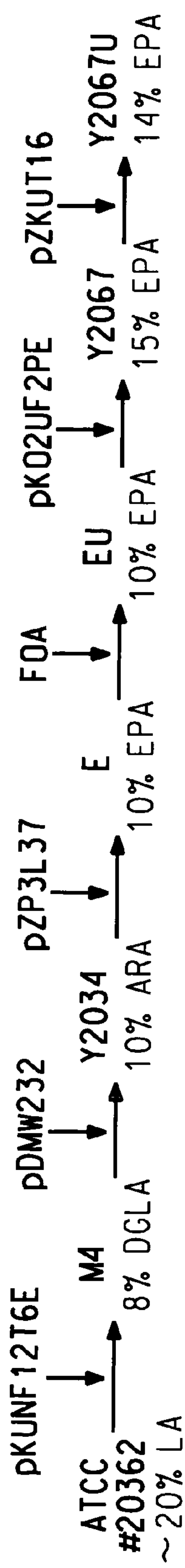
FIG. 3A
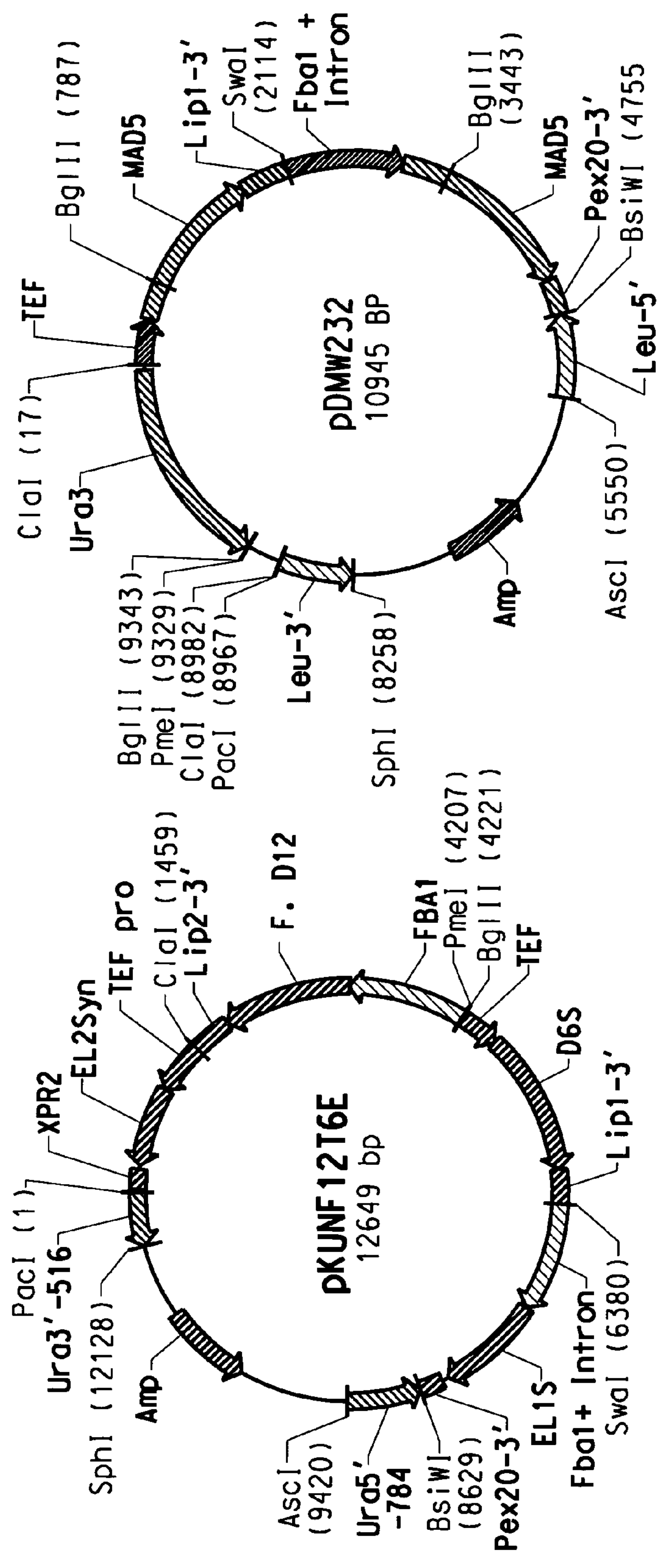
FIG. 3B
FIG. 3C

SEQUENCE LISTING

```
<160> NUMBER OF SEQ ID NOS: 55

<210> SEQ ID NO 1
<211> LENGTH: 1086
<212> TYPE: DNA
<213> ORGANISM: Mortierella alpina
<220> FEATURE:
<221> NAME/KEY: CDS
<222> LOCATION: (22)..(948)

<400> SEQUENCE: 1

gggattcccc cgcttcccgg c atg ctc ggg tcc gtc acc cga ccc aca aag        51
                        Met Leu Gly Ser Val Thr Arg Pro Thr Lys
                        1               5                   10

gcc ctg ctc tat gga tca gcc ctc ttc agt ttc tgc tca ttg ctc aat        99
Ala Leu Leu Tyr Gly Ser Ala Leu Phe Ser Phe Cys Ser Leu Leu Asn
            15                  20                  25
```

-continued

```
gtg gtc cag gtg ttc tcc ata ctc ctg cag ccg ttc tcg aag cgt ctc      147
Val Val Gln Val Phe Ser Ile Leu Leu Gln Pro Phe Ser Lys Arg Leu
            30                  35                  40

ttc ttt gaa gtg aac gct cgc gtg gcc ggc tcc atg tgg aag gtt atg      195
Phe Phe Glu Val Asn Ala Arg Val Ala Gly Ser Met Trp Lys Val Met
        45                  50                  55

cag ctg att atg gag aaa aag cac aag gcc gcc atc acc ttc tca gga      243
Gln Leu Ile Met Glu Lys Lys His Lys Ala Ala Ile Thr Phe Ser Gly
    60                  65                  70

gac aag atc cct cac cac gag agt gcc atc gtc ttt ggc aac cac cgg      291
Asp Lys Ile Pro His His Glu Ser Ala Ile Val Phe Gly Asn His Arg
75                  80                  85                  90

tcc ttt gtc gac ttt tac atg ttt cac acc gtt gct gct cgg aga ggc      339
Ser Phe Val Asp Phe Tyr Met Phe His Thr Val Ala Ala Arg Arg Gly
                95                  100                 105

atg ctc aac tat atg aag tac ttt gcc aag gac tct ctg aaa tac att      387
Met Leu Asn Tyr Met Lys Tyr Phe Ala Lys Asp Ser Leu Lys Tyr Ile
            110                 115                 120

cca ttc tat gga tgg ggc atg tgg atc atg gga atg cta ttc atc aat      435
Pro Phe Tyr Gly Trp Gly Met Trp Ile Met Gly Met Leu Phe Ile Asn
        125                 130                 135

cgc aac tgg cag cag gat cag ctc aag atc aac aag atg ttt gca cgg      483
Arg Asn Trp Gln Gln Asp Gln Leu Lys Ile Asn Lys Met Phe Ala Arg
    140                 145                 150

ata ttg gac atc caa gcg ccc gtt tgg gtc gcc agt ttc ttg gag ggc      531
Ile Leu Asp Ile Gln Ala Pro Val Trp Val Ala Ser Phe Leu Glu Gly
155                 160                 165                 170

tct cgg ttg acg ccc agc aaa ctg gct gcc tct caa aag ttc atg ctg      579
Ser Arg Leu Thr Pro Ser Lys Leu Ala Ala Ser Gln Lys Phe Met Leu
                175                 180                 185

gga cgc gga ttg cct ctg ctg tca aac gtc atg atg ccc agg acc aag      627
Gly Arg Gly Leu Pro Leu Leu Ser Asn Val Met Met Pro Arg Thr Lys
            190                 195                 200

gga ttc att gcc tgt gtc aac aaa ttc cgg gga act cat gtg aaa tgt      675
Gly Phe Ile Ala Cys Val Asn Lys Phe Arg Gly Thr His Val Lys Cys
        205                 210                 215

gtt tat gat ttc acg ttc gcc tac tac cac aag acc aag ggc ttt gga      723
Val Tyr Asp Phe Thr Phe Ala Tyr Tyr His Lys Thr Lys Gly Phe Gly
    220                 225                 230

gtg cct cca gat ctg gtc cgt gtt cac act ggc cag ctc agc ccc gag      771
Val Pro Pro Asp Leu Val Arg Val His Thr Gly Gln Leu Ser Pro Glu
235                 240                 245                 250

tac aaa ttc cat gtt cat gtg aga cgc tat cag ctc gac gat ctg ccc      819
Tyr Lys Phe His Val His Val Arg Arg Tyr Gln Leu Asp Asp Leu Pro
                255                 260                 265

acg gat gag gag aag ctg agc gag tgg gtg gtc caa aag tat gtg gag      867
Thr Asp Glu Glu Lys Leu Ser Glu Trp Val Val Gln Lys Tyr Val Glu
            270                 275                 280

aag gac gcc ttt ttg gag cag atg aag gag aat tgg aca gat ggt att      915
Lys Asp Ala Phe Leu Glu Gln Met Lys Glu Asn Trp Thr Asp Gly Ile
        285                 290                 295

gat ggg ggt gtg tgg tca gag aac tgg atg tga gcgagatgca ccgcaaactg    968
Asp Gly Gly Val Trp Ser Glu Asn Trp Met
    300                 305

tgtacagcgt cttagaggga taagaaagga ttgatatatt taaagaaagg aaacctatcg   1028

ccgattacaa gtaaaaacct ccataatgaa aaaaaaaaaa aaaaaaaaaa aaaaaaa      1086
```

<210> SEQ ID NO 2

-continued

<211> LENGTH: 308
<212> TYPE: PRT
<213> ORGANISM: Mortierella alpina

<400> SEQUENCE: 2

```
Met Leu Gly Ser Val Thr Arg Pro Thr Lys Ala Leu Leu Tyr Gly Ser
1               5                   10                  15

Ala Leu Phe Ser Phe Cys Ser Leu Leu Asn Val Val Gln Val Phe Ser
            20                  25                  30

Ile Leu Leu Gln Pro Phe Ser Lys Arg Leu Phe Phe Glu Val Asn Ala
        35                  40                  45

Arg Val Ala Gly Ser Met Trp Lys Val Met Gln Leu Ile Met Glu Lys
    50                  55                  60

Lys His Lys Ala Ala Ile Thr Phe Ser Gly Asp Lys Ile Pro His His
65                  70                  75                  80

Glu Ser Ala Ile Val Phe Gly Asn His Arg Ser Phe Val Asp Phe Tyr
                85                  90                  95

Met Phe His Thr Val Ala Ala Arg Arg Gly Met Leu Asn Tyr Met Lys
            100                 105                 110

Tyr Phe Ala Lys Asp Ser Leu Lys Tyr Ile Pro Phe Tyr Gly Trp Gly
        115                 120                 125

Met Trp Ile Met Gly Met Leu Phe Ile Asn Arg Asn Trp Gln Gln Asp
    130                 135                 140

Gln Leu Lys Ile Asn Lys Met Phe Ala Arg Ile Leu Asp Ile Gln Ala
145                 150                 155                 160

Pro Val Trp Val Ala Ser Phe Leu Glu Gly Ser Arg Leu Thr Pro Ser
                165                 170                 175

Lys Leu Ala Ala Ser Gln Lys Phe Met Leu Gly Arg Gly Leu Pro Leu
            180                 185                 190

Leu Ser Asn Val Met Met Pro Arg Thr Lys Gly Phe Ile Ala Cys Val
        195                 200                 205

Asn Lys Phe Arg Gly Thr His Val Lys Cys Val Tyr Asp Phe Thr Phe
    210                 215                 220

Ala Tyr Tyr His Lys Thr Lys Gly Phe Gly Val Pro Pro Asp Leu Val
225                 230                 235                 240

Arg Val His Thr Gly Gln Leu Ser Pro Glu Tyr Lys Phe His Val His
                245                 250                 255

Val Arg Arg Tyr Gln Leu Asp Asp Leu Pro Thr Asp Glu Glu Lys Leu
            260                 265                 270

Ser Glu Trp Val Val Gln Lys Tyr Val Glu Lys Asp Ala Phe Leu Glu
        275                 280                 285

Gln Met Lys Glu Asn Trp Thr Asp Gly Ile Asp Gly Gly Val Trp Ser
    290                 295                 300

Glu Asn Trp Met
305
```

<210> SEQ ID NO 3
<211> LENGTH: 927
<212> TYPE: DNA
<213> ORGANISM: Mortierella alpina

<400> SEQUENCE: 3

```
atgctcgggt ccgtcacccg acccacaaag gccctgctct atggatcagc cctcttcagt     60

ttctgctcat tgctcaatgt ggtccaggtg ttctccatac tcctgcagcc gttctcgaag    120

cgtctcttct ttgaagtgaa cgctcgcgtg gccggctcca tgtggaaggt tatgcagctg    180
```

-continued

```
attatggaga aaaagcacaa ggccgccatc accttctcag gagacaagat ccctcaccac    240

gagagtgcca tcgtctttgg caaccaccgg tcctttgtcg acttttacat gtttcacacc    300

gttgctgctc ggagaggcat gctcaactat atgaagtact ttgccaagga ctctctgaaa    360

tacattccat tctatggatg gggcatgtgg atcatgggaa tgctattcat caatcgcaac    420

tggcagcagg atcagctcaa gatcaacaag atgtttgcac ggatattgga catccaagcg    480

cccgtttggg tcgccagttt cttggagggc tctcggttga cgcccagcaa actggctgcc    540

tctcaaaagt tcatgctggg acgcggattg cctctgctgt caaacgtcat gatgcccagg    600

accaagggat tcattgcctg tgtcaacaaa ttccggggaa ctcatgtgaa atgtgtttat    660

gatttcacgt tcgcctacta ccacaagacc aagggctttg gagtgcctcc agatctggtc    720

cgtgttcaca ctggccagct cagccccgag tacaaattcc atgttcatgt gagacgctat    780

cagctcgacg atctgcccac ggatgaggag aagctgagcg agtgggtggt ccaaaagtat    840

gtggagaagg acgccttttt ggagcagatg aaggagaatt ggacagatgg tattgatggg    900

ggtgtgtggt cagagaactg gatgtga                                        927


<210> SEQ ID NO 4
<211> LENGTH: 39
<212> TYPE: DNA
<213> ORGANISM: Artificial Sequence
<220> FEATURE:
<223> OTHER INFORMATION: SMART IV oligonucleotide

<400> SEQUENCE: 4

aagcagtggt atcaacgcag agtggccatt acggccggg                            39


<210> SEQ ID NO 5
<211> LENGTH: 59
<212> TYPE: DNA
<213> ORGANISM: Artificial Sequence
<220> FEATURE:
<223> OTHER INFORMATION: CDSIII/3'PCR primer
<220> FEATURE:
<221> NAME/KEY: misc_feature
<222> LOCATION: (28)..(57)
<223> OTHER INFORMATION: thymidine (dT); see BD Biosciences Clontech's
      SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 5

attctagagg ccgaggcggc cgacatgttt tttttttttt tttttttttt tttttttvn      59


<210> SEQ ID NO 6
<211> LENGTH: 23
<212> TYPE: DNA
<213> ORGANISM: Artificial Sequence
<220> FEATURE:
<223> OTHER INFORMATION: 5'-PCR primer

<400> SEQUENCE: 6

aagcagtggt atcaacgcag agt                                            23


<210> SEQ ID NO 7
<211> LENGTH: 18
<212> TYPE: DNA
<213> ORGANISM: Artificial Sequence
<220> FEATURE:
<223> OTHER INFORMATION: Primer M13
```

<400> SEQUENCE: 7
tgtaaaacga cggccagt 18

<210> SEQ ID NO 8
<211> LENGTH: 325
<212> TYPE: DNA
<213> ORGANISM: Mortierella alpina

<400> SEQUENCE: 8
cgagtacaaa ttccatgttc atgtgagacg ctatcagctc gacgatctgc ccacggatga 60
ggagaagctg agcgagtggg tggtccaaaa gtatgtggag aaggacgcct ttttggagca 120
gatgaaggag aattggacag atggtattga tgggggtgtg tggtcagaga actggatgtg 180
agcgagatgc accgcaaact gtgtacagcg tcttagaggg ataagaaagg attgatatat 240
ttaaagaaag gaaacctatc gccgattaca agtaaaaacc tccataatga aaaaaaaaaa 300
aaaaaaaaaa aaaaaaaaac atgtc 325

<210> SEQ ID NO 9
<211> LENGTH: 22
<212> TYPE: DNA
<213> ORGANISM: Artificial Sequence
<220> FEATURE:
<223> OTHER INFORMATION: Primer MLPAT-RC-1

<400> SEQUENCE: 9
gagctgatag cgtctcacat ga 22

<210> SEQ ID NO 10
<211> LENGTH: 21
<212> TYPE: DNA
<213> ORGANISM: Artificial Sequence
<220> FEATURE:
<223> OTHER INFORMATION: Primer MLPAT-RC-2

<400> SEQUENCE: 10
gaatttgtac tcggggctga g 21

<210> SEQ ID NO 11
<211> LENGTH: 21
<212> TYPE: DNA
<213> ORGANISM: Artificial Sequence
<220> FEATURE:
<223> OTHER INFORMATION: Primer MLPAT-RC-3

<400> SEQUENCE: 11
gaacacggac cagatctgga g 21

<210> SEQ ID NO 12
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 12

-continued

```
taaccctcac taaagggaac aaaagctgga gctccaccgc ggacacaata tctggtcaaa      60
tttcagtttc gttacataaa tcgttatgtc aaaggagtgt gggaggttaa gagaattatc     120
accggcaaac tatctgttaa ttgctaggta cctctagacg tccacccggg tcgcttggcg     180
gccgaagagg ccggaatctc gggccgcggt ggcggccgct tagttggtct tggacttctt     240
gggcttcttc aggtaggact ggacaaagaa gttgccgaac agagcgagca gggtgatcat     300
gtacacgccg agcagctgga ccagagcctg agggtagtcg caggggaaga ggtagtcgta     360
cagggactgc accagcatag ccatgaactg ggtcatctgc agagtggtga tgtagggctt     420
gatgggcttg acgaagccga agccctgaga ggaaaagaag tagtaggcgt acatgacggt     480
gtggacgaag gagttgagga tgacggagaa gtaggcgtcg ccaccaggag cgtacttggc     540
aatagcccac cagatggcga agatggtggc atggtggtac acgtgcagga aggagacctg     600
gttgaacttc ttgcacagga tcatgatagc ggtgtccagg aactcgtagg ccttggagac     660
gtagaacacg tagacgattc gggacatgcc ctgagcgtgg gactcgttgc ccttctccat     720
gtcgttgccg aagaccttgt agccacccag gatagcctgt cggatggtct cgacgcacat     780
gtagagggac agtccgaaga ggaacaggtt gtggagcagc ttgatggtct tcagctcgaa     840
gggcttctcc atctgcttca tgatgggaat gccgaagagc agcatggcca tgtagccgac     900
ctcgaaggcg agcatggtgg agacgtccat catgggcaga ccgtcggtca gagcgtaggg     960
cttagctccg tccatccact ggtcgacacc ggtctcgact cgtccgacca cgtcgtccca    1020
gacagaggag ttggccatgg tgaatgattc ttatactcag aaggaaatgc ttaacgattt    1080
cgggtgtgag ttgacaagga gagagagaaa agaagaggaa aggtaattcg ggacggtgg     1140
tcttttatac ccttggctaa agtcccaacc acaaagcaaa aaaattttca gtagtctatt    1200
ttgcgtccgg catgggttac ccggatggcc agacaaagaa actagtacaa agtctgaaca    1260
agcgtagatt ccagactgca gtaccctacg cccttaacgg caagtgtggg aaccggggga    1320
ggtttgatat gtggggtgaa gggggctctc gccggggttg ggcccgctac tgggtcaatt    1380
tggggtcaat tggggcaatt ggggctgttt tttgggacac aaatacgccg ccaacccggt    1440
ctctcctgaa ttctgcatcg atcgaggaag aggacaagcg gctgcttctt aagtttgtga    1500
catcagtatc caaggcacca ttgcaaggat tcaaggcttt gaacccgtca tttgccattc    1560
gtaacgctgg tagacaggtt gatcggttcc ctacggcctc cacctgtgtc aatcttctca    1620
agctgcctga ctatcaggac attgatcaac ttcggaagaa acttttgtat gccattcgat    1680
cacatgctgg tttcgatttg tcttagagga acgcatatac agtaatcata gagaataaac    1740
gatattcatt tattaaagta gatagttgag gtagaagttg taaagagtga taaatagcgg    1800
ccgcgcctac ttaagcaacg ggcttgataa cagcgggggg ggtgcccacg ttgttgcggt    1860
tgcggaagaa cagaacaccc ttaccagcac cctcggcacc agcgctgggc tcaacccact    1920
ggcacatacg cgcactgcgg tacatggcgc ggatgaagcc acgaggacca tcctggacat    1980
cagcccggta gtgcttgccc atgatgggct taatggcctc ggtggcctcg tccgcgttgt    2040
agaaggggat gctgctgacg tagtggtgga ggacatgagt ctcgatgatg ccgtggagaa    2100
ggtggcggcc gatgaagccc atctcacggt caatggtagc agcggcacca cggacgaagt    2160
tccactcgtc gttggtgtag tggggaaggg tagggtcggt gtgctggagg aaggtgatgg    2220
caacgagcca gtggttaacc cagaggtagg gaacaaagta ccagatggcc atgttgtaga    2280
aaccgaactt ctgaacgagg aagtacagag cagtggccat cagaccgata ccaatatcgc    2340
tgaggacgat gagcttagcg tcactgttct cgtacagagg gctgcgggga tcgaagtggt    2400
```

-continued

```
taacaccacc gccgaggccg ttatgcttgc ccttgccgcg accctcacgc tggcgctcgt   2460
ggtagttgtg gccggtaaca ttggtgatga ggtagttggg ccagccnacg annnnctcag   2520
taagatgagc gagctcgtgg gtcatctttc cgagacgagt agcctgctgc tcgcgggttc   2580
ggggaacgaa gaccatgtca cgctccatgt tgccagtggc cttgtggtgc tttcggtggg   2640
agatttgcca gctgaagtag gggacaagga gggaagagtg aagaacccag ccagtaatgt   2700
cgttgatgat gcgagaatcg gagaaagcac cgtgaccgca ctcatgggca ataacccaga   2760
gaccagtacc gaaaagaccc tgaagaacgg tgtacacggc ccacagacca gcgcgggcgg   2820
gggtggaggg gatatattcg ggggtcacaa agttgtacca gatgctgaaa gtggtagtca   2880
ggaggacaat gtcgcggagg atataaccgt atcccttgag agcggagcgc ttgaagcagt   2940
gcttagggat ggcattgtag atgtccttga tggtaaagtc gggaacctcg aactggttgc   3000
cgtaggtgtc gagcatgaca ccatactcgg acttgggctt ggcgatatca acctcggaca   3060
tggacgagag cgatgtggaa gaggccgagt ggcggggaga gtctgaagga gagacggcgg   3120
cagactcaga atccgtcaca gtagttgagg tgacggtgcg tctaagcgca gggttctgct   3180
tgggcagagc cgaagtggac gccatggaga gctgggttag tttgtgtaga gagtgtgtgt   3240
tgctagcgac tttcggattg tgtcattaca caaaacgcgt cgtctcgaca ctgatcttgt   3300
cgtggatact cacggctcgg acatcgtcgc cgacgatgac accggacttt cgcttaagga   3360
cgtcagtaac aggcattgtg tgatgtgtag tttagatttc gaatctgtgg ggaaagaaag   3420
gaaaaaagag actggcaacc gattgggaga gccactgttt atatataccc tagacaagcc   3480
ccccgcttgt aagatgttgg tcaatgtaaa ccagtattaa ggttggcaag tgcaggagaa   3540
gcaaggtgtg ggtaccgagc aatggaaatg tgcggaaggc aaaaaaatga ggccacggcc   3600
tattgtcggg gctatatcca gggggcgatt gaagtacact aacatgacat gtgtccacag   3660
accctcaatc tggcctgatg agccaaatcc atacgcgctt tcgcagctct aaaggctata   3720
acaagtcaca ccaccctgct cgacctcagc gccctcactt tttgttaaga caaactgtac   3780
acgctgttcc agcgttttct gcctgcacct ggtgggacat ttggtgcaac ctaaagtgct   3840
cggaacctct gtggtgtcca gatcagcgca gcagttccga ggtagttttg aggcccttag   3900
atgatgcaat ggtgtcagtc gctggatcac gagtcttaat ggcagtattc gttcttattt   3960
gtgccattga gccccgttat cctcgtatct tctacccccc atcccatccc tttgttggtg   4020
caaccctacc catttattgt tgggtgcagc ccaaccgacg tggagagctt ggcttggcca   4080
tataaaaagg ccccccccta gtggcaatgg cagaaagtca gctgtgagtt gttgaatttg   4140
tcatctaggc ggcctggccg tcttctccgg ggcaattgtt cctctatagt actgcgtaca   4200
ctgtttaaac agtgtacgca gatctgcgac gacggaattc ctgcagccca tctgcagaat   4260
tcaggagaga ccgggttggc ggcgtatttg tgtcccaaaa aacagcccca attgccccaa   4320
ttgaccccaa attgacccag tagcgggccc aaccccggcg agagccccct tcaccccaca   4380
tatcaaacct cccccggttc ccacacttgc cgttaagggc gtagggtact gcagtctgga   4440
atctacgctt gttcagactt tgtactagtt tctttgtctg gccatccggg taacccatgc   4500
cggacgcaaa atagactact gaaaattttt ttgctttgtg gttgggactt tagccaaggg   4560
tataaaagac caccgtcccc gaattacctt tcctcttctt ttctctctct ccttgtcaac   4620
tcacacccga aatcgttaag catttccttc tgagtataag aatcattcac catggctgcc   4680
gctccctctg tgcgaacctt tacccgagcc gaggttctga acgctgaggc tctgaacgag   4740
```

-continued

```
ggcaagaagg acgctgaggc tcccttcctg atgatcatcg acaacaaggt gtacgacgtc   4800
cgagagttcg tccctgacca tcctggaggc tccgtgattc tcacccacgt tggcaaggac   4860
ggcaccgacg tctttgacac ctttcatccc gaggctgctt gggagactct cgccaacttc   4920
tacgttggag acattgacga gtccgaccga gacatcaaga acgatgactt tgccgctgag   4980
gtccgaaagc tgcgaaccct gttccagtct ctcggctact acgactcctc taaggcctac   5040
tacgccttca aggtctcctt caacctctgc atctggggac tgtccaccgt cattgtggcc   5100
aagtggggtc agacctccac cctcgccaac gtgctctctg ctgccctgct cggcctgttc   5160
tggcagcagt gcggatggct ggctcacgac tttctgcacc accaggtctt ccaggaccga   5220
ttctggggtg atctcttcgg agccttcctg ggaggtgtct gccagggctt ctcctcttcc   5280
tggtggaagg acaagcacaa cactcaccat gccgctccca acgtgcatgg cgaggatcct   5340
gacattgaca cccaccctct cctgacctgg tccgagcacg ctctggagat gttctccgac   5400
gtccccgatg aggagctgac ccgaatgtgg tctcgattca tggtcctgaa ccagacctgg   5460
ttctacttcc ccattctctc cttcgctcga ctgtcttggt gcctccagtc cattctcttt   5520
gtgctgccca acggtcaggc tcacaagccc tccggagctc gagtgcccat ctccctggtc   5580
gagcagctgt ccctcgccat gcactggacc tggtacctcg ctaccatgtt cctgttcatc   5640
aaggatcctg tcaacatgct cgtgtacttc ctggtgtctc aggctgtgtg cggaaacctg   5700
ctcgccatcg tgttctccct caaccacaac ggtatgcctg tgatctccaa ggaggaggct   5760
gtcgacatgg atttctttac caagcagatc atcactggtc gagatgtcca tcctggactg   5820
ttcgccaact ggttcaccgg tggcctgaac taccagatcg agcatcacct gttcccttcc   5880
atgcctcgac acaacttctc caagatccag cctgccgtcg agaccctgtg caagaagtac   5940
aacgtccgat accacaccac tggtatgatc gagggaactg ccgaggtctt ctcccgactg   6000
aacgaggtct ccaaggccac ctccaagatg ggcaaggctc agtaagcggc cgcatgagaa   6060
gataaatata taaatacatt gagatattaa atgcgctaga ttagagagcc tcatactgct   6120
cggagagaag ccaagacgag tactcaaagg ggattacacc atccatatcc acagacacaa   6180
gctggggaaa ggttctatat acactttccg gaataccgta gtttccgatg ttatcaatgg   6240
gggcagccag gatttcaggc acttcggtgt ctcggggtga aatggcgttc ttggcctcca   6300
tcaagtcgta ccatgtcttc atttgcctgt caaagtaaaa cagaagcaga tgaagaatga   6360
acttgaagtg aaggaattta aattgccccg gagaagacgg ccaggccgcc tagatgacaa   6420
attcaacaac tcacagctga ctttctgcca ttgccactag gggggggcct tttatatgg   6480
ccaagccaag ctctccacgt cggttgggct gcacccaaca ataaatgggt agggttgcac   6540
caacaaaggg atgggatggg gggtagaaga tacgaggata acggggctca atggcacaaa   6600
taagaacgaa tactgccatt aagactcgtg atccagcgac tgacaccatt gcatcatcta   6660
agggcctcaa aactacctcg gaactgctgc gctgatctgg acaccacaga ggttccgagc   6720
actttaggtt gcaccaaatg tcccaccagg tgcaggcaga aaacgctgga acagcgtgta   6780
cagtttgtct taacaaaaag tgagggcgct gaggtcgagc agggtggtgt gacttgttat   6840
agcctttaga gctgcgaaag cgcgtatgga tttggctcat caggccagat tgagggtctg   6900
tggacacatg tcatgttagt gtacttcaat cgccccctgg atatagcccc gacaataggc   6960
cgtggcctca tttttttgcc ttccgcacat ttccattgct cggtacccac accttgcttc   7020
tcctgcactt gccaacctta atactggttt acattgacca acatcttaca agcggggggc   7080
ttgtctaggg tatatataaa cagtggctct cccaatcggt tgccagtctc tttttttcctt   7140
```

-continued

```
tctttcccca cagattcgaa atctaaacta cacatcacac aatgcctgtt actgacgtcc   7200
ttaagcgaaa gtccggtgtc atcgtcggcg acgatgtccg agccgtgagt atccacgaca   7260
agatcagtgt cgagacgacg cgttttgtgt aatgacacaa tccgaaagtc gctagcaaca   7320
cacactctct acacaaacta acccagctct ccatggagtc cattgctccc ttcctgccct   7380
ccaagatgcc tcaggacctg ttcatggacc tcgccagcgc tatcggtgtc cgagctgctc   7440
cctacgtcga tcccctggag gctgccctgg ttgcccaggc cgagaagtac attcccacca   7500
ttgtccatca cactcgaggc ttcctggttg ccgtggagtc tcccctggct cgagagctgc   7560
ctctgatgaa cccctccac gtgctcctga tcgtgctcgc ctacctggtc accgtgtttg   7620
tgggtatgca gatcatgaag aactttgaac gattcgaggt caagaccttc tccctcctgc   7680
acaacttctg tctggtctcc atctccgcct acatgtgcgg tggcatcctg tacgaggctt   7740
atcaggccaa ctatggactg tttgagaacg ctgccgatca caccttcaag ggtctcccta   7800
tggctaagat gatctggctc ttctacttct ccaagatcat ggagtttgtc gacaccatga   7860
tcatggtcct caagaagaac aaccgacaga tttcctttct gcacgtgtac caccactctt   7920
ccatcttcac catctggtgg ctggtcacct tcgttgctcc caacggtgaa gcctacttct   7980
ctgctgccct gaactccttc atccacgtca tcatgtacgg ctactacttt ctgtctgccc   8040
tgggcttcaa gcaggtgtcg ttcatcaagt tctacatcac tcgatcccag atgacccagt   8100
tctgcatgat gtctgtccag tcttcctggg acatgtacgc catgaaggtc cttggccgac   8160
ctggataccc cttcttcatc accgctctgc tctggttcta catgtggacc atgctcggtc   8220
tcttctacaa cttttaccga aagaacgcca agctcgccaa gcaggccaag gctgacgctg   8280
ccaaggagaa ggccagaaag ctccagtaag cggccgcaag tgtggatggg gaagtgagtg   8340
cccggttctg tgtgcacaat tggcaatcca agatggatgg attcaacaca gggatatagc   8400
gagctacgtg gtggtgcgag gatatagcaa cggatattta tgtttgacac ttgagaatgt   8460
acgatacaag cactgtccaa gtacaatact aaacatactg tacatactca tactcgtacc   8520
cgggcaacgg tttcacttga gtgcagtggc tagtgctctt actcgtacag tgtgcaatac   8580
tgcgtatcat agtctttgat gtatatcgta ttcattcatg ttagttgcgt acgaagtcgt   8640
caatgatgtc gatatgggtt ttgatcatgc acacataagg tccgacctta tcggcaagct   8700
caatgagctc cttggtggtg gtaacatcca gagaagcaca caggttggtt ttcttggctg   8760
ccacgagctt gagcactcga gcggcaaagg cggacttgtg gacgttagct cgagcttcgt   8820
aggagggcat tttggtggtg aagaggagac tgaaataaat ttagtctgca gaacttttta   8880
tcggaacctt atctggggca gtgaagtata tgttatggta atagttacga gttagttgaa   8940
cttatagata gactggacta tacggctatc ggtccaaatt agaaagaacg tcaatggctc   9000
tctgggcgtc gcctttgccg acaaaaatgt gatcatgatg aaagccagca atgacgttgc   9060
agctgatatt gttgtcggcc aaccgcgccg aaaacgcagc tgtcagaccc acagcctcca   9120
acgaagaatg tatcgtcaaa gtgatccaag cacactcata gttggagtcg tactccaaag   9180
gcggcaatga cgagtcagac agatactcgt cgaccttttc cttgggaacc accaccgtca   9240
gcccttctga ctcacgtatt gtagccaccg acacaggcaa cagtccgtgg atagcagaat   9300
atgtcttgtc ggtccatttc tcaccaactt taggcgtcaa gtgaatgttg cagaagaagt   9360
atgtgccttc attgagaatc ggtgttgctg atttcaataa agtcttgaga tcagtttggc   9420
gcgccagctg cattaatgaa tcggccaacg cgcggggaga ggcggtttgc gtattgggcg   9480
```

-continued

```
ctcttccgct tcctcgctca ctgactcgct gcgctcggtc gttcggctgc ggcgagcggt    9540
atcagctcac tcaaaggcgg taatacggtt atccacagaa tcaggggata acgcaggaaa    9600
gaacatgtga gcaaaaggcc agcaaaaggc caggaaccgt aaaaaggccg cgttgctggc    9660
gtttttccat aggctccgcc cccctgacga gcatcacaaa aatcgacgct caagtcagag    9720
gtggcgaaac ccgacaggac tataaagata ccaggcgttt ccccctggaa gctccctcgt    9780
gcgctctcct gttccgaccc tgccgcttac cggatacctg tccgcctttc tcccttcggg    9840
aagcgtggcg ctttctcata gctcacgctg taggtatctc agttcggtgt aggtcgttcg    9900
ctccaagctg ggctgtgtgc acgaaccccc cgttcagccc gaccgctgcg ccttatccgg    9960
taactatcgt cttgagtcca acccggtaag acacgactta tcgccactgg cagcagccac   10020
tggtaacagg attagcagag cgaggtatgt aggcggtgct acagagttct tgaagtggtg   10080
gcctaactac ggctacacta gaagaacagt atttggtatc tgcgctctgc tgaagccagt   10140
taccttcgga aaaagagttg gtagctcttg atccggcaaa caaaccaccg ctggtagcgg   10200
tggttttttt gtttgcaagc agcagattac gcgcagaaaa aaaggatctc aagaagatcc   10260
tttgatcttt tctacggggt ctgacgctca gtggaacgaa aactcacgtt aagggatttt   10320
ggtcatgaga ttatcaaaaa ggatcttcac ctagatcctt ttaaattaaa aatgaagttt   10380
taaatcaatc taaagtatat atgagtaaac ttggtctgac agttaccaat gcttaatcag   10440
tgaggcacct atctcagcga tctgtctatt tcgttcatcc atagttgcct gactccccgt   10500
cgtgtagata actacgatac gggagggctt accatctggc cccagtgctg caatgatacc   10560
gcgagaccca cgctcaccgg ctccagattt atcagcaata aaccagccag ccggaagggc   10620
cgagcgcaga agtggtcctg caactttatc cgcctccatc cagtctatta attgttgccg   10680
ggaagctaga gtaagtagtt cgccagttaa tagtttgcgc aacgttgttg ccattgctac   10740
aggcatcgtg gtgtcacgct cgtcgtttgg tatggcttca ttcagctccg gttcccaacg   10800
atcaaggcga gttacatgat cccccatgtt gtgcaaaaaa gcggttagct ccttcggtcc   10860
tccgatcgtt gtcagaagta agttggccgc agtgttatca ctcatggtta tggcagcact   10920
gcataattct cttactgtca tgccatccgt aagatgcttt tctgtgactg gtgagtactc   10980
aaccaagtca ttctgagaat agtgtatgcg gcgaccgagt tgctcttgcc cggcgtcaat   11040
acgggataat accgcgccac atagcagaac tttaaaagtg ctcatcattg gaaaacgttc   11100
ttcggggcga aaactctcaa ggatcttacc gctgttgaga tccagttcga tgtaacccac   11160
tcgtgcaccc aactgatctt cagcatcttt tactttcacc agcgtttctg ggtgagcaaa   11220
aacaggaagg caaaatgccg caaaaaaggg aataagggcg acacggaaat gttgaatact   11280
catactcttc ctttttcaat attattgaag catttatcag ggttattgtc tcatgagcgg   11340
atacatattt gaatgtattt agaaaaataa acaaataggg gttccgcgca catttccccg   11400
aaaagtgcca cctgatgcgg tgtgaaatac cgcacagatg cgtaaggaga aaataccgca   11460
tcaggaaatt gtaagcgtta atattttgtt aaaattcgcg ttaaattttt gttaaatcag   11520
ctcatttttt aaccaatagg ccgaaatcgg caaaatccct tataaatcaa aagaatagac   11580
cgagataggg ttgagtgttg ttccagtttg gaacaagagt ccactattaa agaacgtgga   11640
ctccaacgtc aaagggcgaa aaaccgtcta tcagggcgat ggcccactac gtgaaccatc   11700
accctaatca agtttttttgg ggtcgaggtg ccgtaaagca ctaaatcgga accctaaagg   11760
gagcccccga tttagagctt gacggggaaa gccggcgaac gtggcgagaa aggaagggaa   11820
gaaagcgaaa ggagcgggcg ctagggcgct ggcaagtgta gcggtcacgc tgcgcgtaac   11880
```

```
caccacaccc gccgcgctta atgcgccgct acagggcgcg tccattcgcc attcaggctg  11940

cgcaactgtt gggaagggcg atcggtgcgg gcctcttcgc tattacgcca gctggcgaaa  12000

gggggatgtg ctgcaaggcg attaagttgg gtaacgccag ggttttccca gtcacgacgt  12060

tgtaaaacga cggccagtga attgtaatac gactcactat agggcgaatt gggcccgacg  12120

tcgcatgcag tggtggtatt gtgactgggg atgtagttga gaataagtca tacacaagtc  12180

agctttcttc gagcctcata taagtataag tagttcaacg tattagcact gtacccagca  12240

tctccgtatc gagaaacaca acaacatgcc ccattggaca gatcatgcgg atacacaggt  12300

tgtgcagtat catacatact cgatcagaca ggtcgtctga ccatcataca agctgaacaa  12360

gcgctccata cttgcacgct ctctatatac acagttaaat tacatatcca tagtctaacc  12420

tctaacagtt aatcttctgg taagcctccc agccagcctt ctggtatcgc ttggcctcct  12480

caataggatc tcggttctgg ccgtacagac ctcggccgac aattatgata tccgttccgg  12540

tagacatgac atcctcaaca gttcggtact gctgtccgag agcgtctccc ttgtcgtcaa  12600

gacccacccc gggggtcaga ataagccagt cctcagagtc gcccttaat             12649
```

<210> SEQ ID NO 13
<211> LENGTH: 973
<212> TYPE: DNA
<213> ORGANISM: Yarrowia lipolytica
<220> FEATURE:
<221> NAME/KEY: misc_feature
<223> OTHER INFORMATION: Promoter FBAIN

<400> SEQUENCE: 13

```
aaattgcccc ggagaagacg gccaggccgc ctagatgaca aattcaacaa ctcacagctg     60

actttctgcc attgccacta gggggggcc tttttatatg gccaagccaa gctctccacg     120

tcggttgggc tgcacccaac aataaatggg tagggttgca ccaacaaagg gatgggatgg    180

ggggtagaag atacgaggat aacggggctc aatggcacaa ataagaacga atactgccat    240

taagactcgt gatccagcga ctgacaccat tgcatcatct aagggcctca aaactacctc    300

ggaactgctg cgctgatctg gacaccacag aggttccgag cactttaggt tgcaccaaat    360

gtcccaccag gtgcaggcag aaaacgctgg aacagcgtgt acagtttgtc ttaacaaaaa    420

gtgagggcgc tgaggtcgag cagggtggtg tgacttgtta tagcctttag agctgcgaaa    480

gcgcgtatgg atttggctca tcaggccaga ttgagggtct gtggacacat gtcatgttag    540

tgtacttcaa tcgccccctg gatatagccc cgacaatagg ccgtggcctc atttttttgc    600

cttccgcaca tttccattgc tcggtaccca caccttgctt ctcctgcact tgccaacctt    660

aatactggtt tacattgacc aacatcttac aagcgggggg cttgtctagg gtatatataa    720

acagtggctc tcccaatcgg ttgccagtct cttttttcct ttctttcccc acagattcga    780

aatctaaact acacatcaca caatgcctgt tactgacgtc cttaagcgaa agtccggtgt    840

catcgtcggc gacgatgtcc gagccgtgag tatccacgac aagatcagtg tcgagacgac    900

gcgttttgtg taatgacaca atccgaaagt cgctagcaac acacactctc tacacaaact    960

aacccagctc tcc                                                       973
```

<210> SEQ ID NO 14
<211> LENGTH: 957
<212> TYPE: DNA
<213> ORGANISM: Mortierella alpina
<220> FEATURE:
<221> NAME/KEY: misc_feature -continued
<223> OTHER INFORMATION: synthetic elongase 1 (codon-optimized)

<400> SEQUENCE: 14

```
atggagtcca ttgctccctt cctgccctcc aagatgcctc aggacctgtt catggacctc     60
gccagcgcta tcggtgtccg agctgctccc tacgtcgatc ccctggaggc tgccctggtt    120
gcccaggccg agaagtacat tcccaccatt gtccatcaca ctcgaggctt cctggttgcc    180
gtggagtctc ccctggctcg agagctgcct ctgatgaacc ccttccacgt gctcctgatc    240
gtgctcgcct acctggtcac cgtgtttgtg ggtatgcaga tcatgaagaa ctttgaacga    300
ttcgaggtca agaccttctc cctcctgcac aacttctgtc tggtctccat ctccgcctac    360
atgtgcggtg gcatcctgta cgaggcttat caggccaact atggactgtt tgagaacgct    420
gccgatcaca ccttcaaggg tctccctatg gctaagatga tctggctctt ctacttctcc    480
aagatcatgg agtttgtcga caccatgatc atggtcctca agaagaacaa ccgacagatt    540
tcctttctgc acgtgtacca ccactcttcc atcttcacca tctggtggct ggtcaccttc    600
gttgctccca acggtgaagc ctacttctct gctgccctga actccttcat ccacgtcatc    660
atgtacggct actactttct gtctgccctg ggcttcaagc aggtgtcgtt catcaagttc    720
tacatcactc gatcccagat gacccagttc tgcatgatgt ctgtccagtc ttcctgggac    780
atgtacgcca tgaaggtcct tggccgacct ggatacccct tcttcatcac cgctctgctc    840
tggttctaca tgtggaccat gctcggtctc ttctacaact ttaccgaaa gaacgccaag     900
ctcgccaagc aggccaaggc tgacgctgcc aaggagaagg ccagaaagct ccagtaa       957
```

<210> SEQ ID NO 15
<211> LENGTH: 318
<212> TYPE: PRT
<213> ORGANISM: Mortierella alpina AX464731

<400> SEQUENCE: 15

```
Met Glu Ser Ile Ala Pro Phe Leu Pro Ser Lys Met Pro Gln Asp Leu
1               5                   10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190
```

-continued

```
Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315
```

<210> SEQ ID NO 16
<211> LENGTH: 1374
<212> TYPE: DNA
<213> ORGANISM: Mortierella alpina
<220> FEATURE:
<221> NAME/KEY: misc_feature
<223> OTHER INFORMATION: synthetic delta-6 desaturase (codon-optimized)

<400> SEQUENCE: 16

```
atggctgccg ctccctctgt gcgaaccttt acccgagccg aggttctgaa cgctgaggct     60

ctgaacgagg gcaagaagga cgctgaggct cccttcctga tgatcatcga caacaaggtg    120

tacgacgtcc gagagttcgt ccctgaccat cctggaggct ccgtgattct cacccacgtt    180

ggcaaggacg gcaccgacgt ctttgacacc tttcatcccg aggctgcttg ggagactctc    240

gccaacttct acgttggaga cattgacgag tccgaccgag acatcaagaa cgatgacttt    300

gccgctgagg tccgaaagct gcgaaccctg ttccagtctc tcggctacta cgactcctct    360

aaggcctact acgccttcaa ggtctccttc aacctctgca tctggggact gtccaccgtc    420

attgtggcca agtggggtca gacctccacc ctcgccaacg tgctctctgc tgccctgctc    480

ggcctgttct ggcagcagtg cggatggctg gctcacgact ttctgcacca ccaggtcttc    540

caggaccgat tctggggtga tctcttcgga gccttcctgg gaggtgtctg ccagggcttc    600

tcctcttcct ggtggaagga caagcacaac actcaccatg ccgctcccaa cgtgcatggc    660

gaggatcctg acattgacac ccaccctctc ctgacctggt ccgagcacgc tctggagatg    720

ttctccgacg tccccgatga ggagctgacc cgaatgtggt ctcgattcat ggtcctgaac    780

cagacctggt tctacttccc cattctctcc ttcgctcgac tgtcttggtg cctccagtcc    840

attctctttg tgctgcccaa cggtcaggct cacaagccct ccggagctcg agtgcccatc    900

tccctggtcg agcagctgtc cctcgccatg cactggacct ggtacctcgc taccatgttc    960

ctgttcatca aggatcctgt caacatgctc gtgtacttcc tggtgtctca ggctgtgtgc   1020

ggaaacctgc tcgccatcgt gttctccctc aaccacaacg gtatgcctgt gatctccaag   1080

gaggaggctg tcgacatgga tttctttacc aagcagatca tcactggtcg agatgtccat   1140

cctggactgt tcgccaactg gttcaccggt ggcctgaact accagatcga gcatcacctg   1200

ttcccttcca tgcctcgaca caacttctcc aagatccagc ctgccgtcga gaccctgtgc   1260

aagaagtaca acgtccgata ccacaccact ggtatgatcg agggaactgc cgaggtcttc   1320
```

-continued

```
tcccgactga acgaggtctc caaggccacc tccaagatgg gcaaggctca gtaa        1374


<210> SEQ ID NO 17
<211> LENGTH: 457
<212> TYPE: PRT
<213> ORGANISM: Mortierella alpina AF465281

<400> SEQUENCE: 17

Met Ala Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365
```

```
Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Thr Ser Lys Met Gly Lys Ala Gln
    450                 455


<210> SEQ ID NO 18
<211> LENGTH: 1001
<212> TYPE: DNA
<213> ORGANISM: Yarrowia lipolytica
<220> FEATURE:
<221> NAME/KEY: misc_feature
<223> OTHER INFORMATION: Promoter FBA

<400> SEQUENCE: 18

taaacagtgt acgcagtact atagaggaac aattgccccg gagaagacgg ccaggccgcc      60

tagatgacaa attcaacaac tcacagctga ctttctgcca ttgccactag gggggggcctt     120

tttatatggc caagccaagc tctccacgtc ggttgggctg cacccaacaa taaatgggta     180

gggttgcacc aacaaaggga tgggatgggg ggtagaagat acgaggataa cggggctcaa     240

tggcacaaat aagaacgaat actgccatta agactcgtga tccagcgact gacaccattg     300

catcatctaa gggcctcaaa actacctcgg aactgctgcg ctgatctgga caccacagag     360

gttccgagca ctttaggttg caccaaatgt cccaccaggt gcaggcagaa aacgctggaa     420

cagcgtgtac agtttgtctt aacaaaaagt gagggcgctg aggtcgagca gggtggtgtg     480

acttgttata gcctttagag ctgcgaaagc gcgtatggat ttggctcatc aggccagatt     540

gagggtctgt ggacacatgt catgttagtg tacttcaatc gccccctgga tatagccccg     600

acaataggcc gtggcctcat ttttttgcct tccgcacatt tccattgctc ggtacccaca     660

ccttgcttct cctgcacttg ccaaccttaa tactggttta cattgaccaa catcttacaa     720

gcgggggct tgtctagggt atatataaac agtggctctc ccaatcggtt gccagtctct     780

tttttccttt ctttccccac agattcgaaa tctaaactac acatcacaca atgcctgtta     840

ctgacgtcct taagcgaaag tccggtgtca tcgtcggcga cgatgtccga gccgtgagta     900

tccacgacaa gatcagtgtc gagacgacgc gttttgtgta atgacacaat ccgaaagtcg     960

ctagcaacac acactctcta cacaaactaa cccagctctc c                         1001


<210> SEQ ID NO 19
<211> LENGTH: 1434
<212> TYPE: DNA
<213> ORGANISM: Fusarium monoliforme
<220> FEATURE:
<221> NAME/KEY: misc_feature
<223> OTHER INFORMATION: delta-12 desaturase

<400> SEQUENCE: 19

atggcgtcca cttcggctct gcccaagcag aaccctgcgc ttagacgcac cgtcacctca      60

actactgtga cggattctga gtctgccgcc gtctctcctt cagactctcc ccgccactcg     120
```

-continued

```
gcctcttcca catcgctctc gtccatgtcc gaggttgata tcgccaagcc caagtccgag    180

tatggtgtca tgctcgacac ctacggcaac cagttcgagg ttcccgactt taccatcaag    240

gacatctaca atgccatccc taagcactgc ttcaagcgct ccgctctcaa gggatacggt    300

tatatcctcc gcgacattgt cctcctgact accactttca gcatctggta caactttgtg    360

acccccgaat atatcccctc cacccccgcc cgcgctggtc tgtgggccgt gtacaccgtt    420

cttcagggtc ttttcggtac tggtctctgg gttattgccc atgagtgcgg tcacggtgct    480

ttctccgatt ctcgcatcat caacgacatt actggctggg ttcttcactc ttccctcctt    540

gtcccctact tcagctggca aatctcccac cgaaagcacc acaaggccac tggcaacatg    600

gagcgtgaca tggtcttcgt tccccgaacc cgcgagcagc aggctactcg tctcggaaag    660

atgacccacg agctcgctca tcttactgag gagacccccg ctttcactct tctcatgctc    720

gtccttcagc agctcgttgg ctggcccaac tacctcatca ccaatgttac cggccacaac    780

taccacgagc gccagcgtga gggtcgcggc aagggcaagc ataacggcct cggcggtggt    840

gttaaccact tcgatccccg cagccctctg tacgagaaca gtgacgctaa gctcatcgtc    900

ctcagcgata ttggtatcgg tctgatggcc actgctctgt acttcctcgt tcagaagttc    960

ggtttctaca acatggccat ctggtacttt gttccctacc tctgggttaa ccactggctc   1020

gttgccatca ccttcctcca gcacaccgac cctacccttc cccactacac caacgacgag   1080

tggaacttcg tccgtggtgc cgctgctacc attgaccgtg agatgggctt catcggccgc   1140

caccttctcc acggcatcat cgagactcat gtcctccacc actacgtcag cagcatcccc   1200

ttctacaacg cggacgaggc caccgaggcc attaagccca tcatgggcaa gcactaccgg   1260

gctgatgtcc aggatggtcc tcgtggcttc atccgcgcca tgtaccgcag tgcgcgtatg   1320

tgccagtggg ttgagcccag cgctggtgcc gagggtgctg gtaagggtgt tctgttcttc   1380

cgcaaccgca acaacgtggg caccccccc gctgttatca agcccgttgc ttaa          1434
```

```
<210> SEQ ID NO 20
<211> LENGTH: 477
<212> TYPE: PRT
<213> ORGANISM: Fusarium monoliforme

<400> SEQUENCE: 20

Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30

Pro Ser Asp Ser Pro Arg His Ser Ala Ser Ser Thr Ser Leu Ser Ser
        35                  40                  45

Met Ser Glu Val Asp Ile Ala Lys Pro Lys Ser Glu Tyr Gly Val Met
    50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
            100                 105                 110

Phe Ser Ile Trp Tyr Asn Phe Val Thr Pro Glu Tyr Ile Pro Ser Thr
        115                 120                 125

Pro Ala Arg Ala Gly Leu Trp Ala Val Tyr Thr Val Leu Gln Gly Leu
    130                 135                 140
```

-continued

```
Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
    210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415

Lys His Tyr Arg Ala Asp Val Gln Asp Gly Pro Arg Gly Phe Ile Arg
            420                 425                 430

Ala Met Tyr Arg Ser Ala Arg Met Cys Gln Trp Val Glu Pro Ser Ala
        435                 440                 445

Gly Ala Glu Gly Ala Gly Lys Gly Val Leu Phe Phe Arg Asn Arg Asn
    450                 455                 460

Asn Val Gly Thr Pro Pro Ala Val Ile Lys Pro Val Ala
465                 470                 475
```

<210> SEQ ID NO 21
<211> LENGTH: 819
<212> TYPE: DNA
<213> ORGANISM: Thraustochytrium aureum
<220> FEATURE:
<221> NAME/KEY: misc_feature
<223> OTHER INFORMATION: synthetic elongase (codon-optimized)

<400> SEQUENCE: 21

```
atggccaact cctctgtctg ggacgacgtg gtcggacgag tcgagaccgg tgtcgaccag     60

tggatggacg gagctaagcc ctacgctctg accgacggtc tgcccatgat ggacgtctcc    120

accatgctcg ccttcgaggt cggctacatg gccatgctgc tcttcggcat tcccatcatg    180
```

```
aagcagatgg agaagccctt cgagctgaag accatcaagc tgctccacaa cctgttcctc    240

ttcggactgt ccctctacat gtgcgtcgag accatccgac aggctatcct gggtggctac    300

aaggtcttcg gcaacgacat ggagaagggc aacgagtccc acgctcaggg catgtcccga    360

atcgtctacg tgttctacgt ctccaaggcc tacgagttcc tggacaccgc tatcatgatc    420

ctgtgcaaga agttcaacca ggtctccttc ctgcacgtgt accaccatgc caccatcttc    480

gccatctggt gggctattgc caagtacgct cctggtggcg acgcctactt ctccgtcatc    540

ctcaactcct tcgtccacac cgtcatgtac gcctactact tcttttcctc tcagggcttc    600

ggcttcgtca agcccatcaa gccctacatc accactctgc agatgaccca gttcatggct    660

atgctggtgc agtccctgta cgactacctc ttcccctgcg actaccctca ggctctggtc    720

cagctgctcg gcgtgtacat gatcaccctg ctcgctctgt tcggcaactt ctttgtccag    780

tcctacctga agaagcccaa gaagtccaag accaactaa                           819
```

<210> SEQ ID NO 22
<211> LENGTH: 272
<212> TYPE: PRT
<213> ORGANISM: Thraustochytrium aureum

<400> SEQUENCE: 22

```
Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
    130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
    210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255
```

-continued

```
Phe Phe Val Gln Ser Tyr Leu Lys Lys Pro Lys Lys Ser Lys Thr Asn
            260                 265                 270
```

<210> SEQ ID NO 23
<211> LENGTH: 10945
<212> TYPE: DNA
<213> ORGANISM: Artificial Sequence
<220> FEATURE:
<223> OTHER INFORMATION: Plasmid pDMW232

<400> SEQUENCE: 23

```
aattcctgca gcccatcgat caggagagac cgggttggcg gcgtatttgt gtcccaaaaa     60
acagccccaa ttgccccaat tgaccccaaa ttgacccagt agcgggccca accccggcga    120
gagcccccctt caccccacat atcaaacctc ccccggttcc cacacttgcc gttaagggcg    180
tagggtactg cagtctggaa tctacgcttg ttcagacttt gtactagttt ctttgtctgg    240
ccatccgggt aacccatgcc ggacgcaaaa tagactactg aaaatttttt tgctttgtgg    300
ttgggacttt agccaagggt ataaaagacc accgtccccg aattaccttt cctcttcttt    360
tctctctctc cttgtcaact cacacccgaa atcgttaagc atttccttct gagtataaga    420
atcattcacc atgggaacgg accaaggaaa aaccttcacc tgggaagagc tggcggccca    480
taacaccaag gacgacctac tcttggccat ccgcggcagg gtgtacgatg tcacaaagtt    540
cttgagccgc catcctggtg gagtggacac tctcctgctc ggagctggcc gagatgttac    600
tccggtcttt gagatgtatc acgcgtttgg ggctgcagat gccattatga agaagtacta    660
tgtcggtaca ctggtctcga atgagctgcc catcttcccg gagccaacgg tgttccacaa    720
aaccatcaag acgagagtcg agggctactt tacggatcgg aacattgatc ccaagaatag    780
accagagatc tggggacgat acgctcttat ctttggatcc ttgatcgctt cctactacgc    840
gcagctcttt gtgcctttcg ttgtcgaacg cacatggctt caggtggtgt ttgcaatcat    900
catgggattt gcgtgcgcac aagtcggact caaccctctt catgatgcgt ctcacttttc    960
agtgacccac aaccccactg tctggaagat tctgggagcc acgcacgact ttttcaacgg   1020
agcatcgtac ctggtgtgga tgtaccaaca tatgctcggc catcacccct acaccaacat   1080
tgctggagca gatcccgacg tgtcgacgtc tgagcccgat gttcgtcgta tcaagcccaa   1140
ccaaaagtgg tttgtcaacc acatcaacca gcacatgttt gttcctttcc tgtacggact   1200
gctggcgttc aaggtgcgca ttcaggacat caacattttg tactttgtca agaccaatga   1260
cgctattcgt gtcaatccca tctcgacatg gcacactgtg atgttctggg gcggcaaggc   1320
tttctttgtc tggtatcgcc tgattgttcc cctgcagtat ctgcccctgg gcaaggtgct   1380
gctcttgttc acggtcgcgg acatggtgtc gtcttactgg ctggcgctga ccttccaggc   1440
gaaccacgtt gttgaggaag ttcagtggcc gttgcctgac gagaacggga tcatccaaaa   1500
ggactgggca gctatgcagg tcgagactac gcaggattac gcacacgatt cgcacctctg   1560
gaccagcatc actggcagct tgaactacca ggctgtgcac catctgttcc ccaacgtgtc   1620
gcagcaccat tatcccgata ttctggccat catcaagaac acctgcagcg agtacaaggt   1680
tccatacctt gtcaaggata cgttttggca agcatttgct tcacatttgg agcacttgcg   1740
tgttcttgga ctccgtccca aggaagagta ggcagctaag cggccgcatg agaagataaa   1800
tatataaata cattgagata ttaaatgcgc tagattagag agcctcatac tgctcggaga   1860
gaagccaaga cgagtactca aaggggatta caccatccat atccacagac acaagctggg   1920
gaaaggttct atatacactt tccggaatac cgtagtttcc gatgttatca atgggggcag   1980
```

-continued

```
ccaggatttc aggcacttcg gtgtctcggg gtgaaatggc gttcttggcc tccatcaagt   2040
cgtaccatgt cttcatttgc ctgtcaaagt aaaacagaag cagatgaaga atgaacttga   2100
agtgaaggaa tttaaattgc cccggagaag acggccaggc cgcctagatg acaaattcaa   2160
caactcacag ctgactttct gccattgcca ctaggggggg gcctttttat atggccaagc   2220
caagctctcc acgtcggttg ggctgcaccc aacaataaat gggtagggtt gcaccaacaa   2280
agggatggga tgggggtag aagatacgag gataacgggg ctcaatggca caaataagaa   2340
cgaatactgc cattaagact cgtgatccag cgactgacac cattgcatca tctaagggcc   2400
tcaaaactac ctcggaactg ctgcgctgat ctggacacca cagaggttcc gagcacttta   2460
ggttgcacca aatgtcccac caggtgcagg cagaaaacgc tggaacagcg tgtacagttt   2520
gtcttaacaa aaagtgaggg cgctgaggtc gagcagggtg gtgtgacttg ttatagcctt   2580
tagagctgcg aaagcgcgta tggatttggc tcatcaggcc agattgaggg tctgtggaca   2640
catgtcatgt tagtgtactt caatcgcccc ctggatatag ccccgacaat aggccgtggc   2700
ctcatttttt tgccttccgc acatttccat tgctcggtac ccacaccttg cttctcctgc   2760
acttgccaac cttaatactg gtttacattg accaacatct tacaagcggg gggcttgtct   2820
agggtatata taaacagtgg ctctcccaat cggttgccag tctctttttt cctttctttc   2880
cccacagatt cgaaatctaa actacacatc acacaatgcc tgttactgac gtccttaagc   2940
gaaagtccgg tgtcatcgtc ggcgacgatg tccgagccgt gagtatccac gacaagatca   3000
gtgtcgagac gacgcgtttt gtgtaatgac acaatccgaa agtcgctagc aacacacact   3060
ctctacacaa actaacccag ctctccatgg gaacggacca aggaaaaacc ttcacctggg   3120
aagagctggc ggcccataac accaaggacg acctactctt ggccatccgc ggcagggtgt   3180
acgatgtcac aaagttcttg agccgccatc ctggtggagt ggacactctc ctgctcggag   3240
ctggccgaga tgttactccg gtctttgaga tgtatcacgc gtttggggct gcagatgcca   3300
ttatgaagaa gtactatgtc ggtacactgg tctcgaatga gctgcccatc ttcccggagc   3360
caacggtgtt ccacaaaacc atcaagacga gagtcgaggg ctactttacg gatcggaaca   3420
ttgatcccaa gaatagacca gagatctggg gacgatacgc tcttatcttt ggatccttga   3480
tcgcttccta ctacgcgcag ctctttgtgc ctttcgttgt cgaacgcaca tggcttcagg   3540
tggtgtttgc aatcatcatg ggatttgcgt gcgcacaagt cggactcaac cctcttcatg   3600
atgcgtctca cttttcagtg acccacaacc ccactgtctg gaagattctg ggagccacgc   3660
acgacttttt caacggagca tcgtacctgg tgtggatgta ccaacatatg ctcggccatc   3720
acccctacac caacattgct ggagcagatc ccgacgtgtc gacgtctgag cccgatgttc   3780
gtcgtatcaa gcccaaccaa aagtggtttg tcaaccacat caaccagcac atgtttgttc   3840
ctttcctgta cggactgctg gcgttcaagg tgcgcattca ggacatcaac attttgtact   3900
ttgtcaagac caatgacgct attcgtgtca atcccatctc gacatggcac actgtgatgt   3960
tctggggcgg caaggctttc tttgtctggt atcgcctgat tgttcccctg cagtatctgc   4020
ccctgggcaa ggtgctgctc ttgttcacgg tcgcggacat ggtgtcgtct tactggctgg   4080
cgctgacctt ccaggcgaac cacgttgttg aggaagttca gtggccgttg cctgacgaga   4140
acgggatcat ccaaaaggac tgggcagcta tgcaggtcga gactacgcag gattacgcac   4200
acgattcgca cctctggacc agcatcactg gcagcttgaa ctaccaggct gtgcaccatc   4260
tgttccccaa cgtgtcgcag caccattatc ccgatattct ggccatcatc aagaacacct   4320
gcagcgagta caaggttcca taccttgtca aggatacgtt ttggcaagca tttgcttcac   4380
```

```
atttggagca cttgcgtgtt cttggactcc gtcccaagga agagtaggca gctaagcggc   4440
cgcaagtgtg gatggggaag tgagtgcccg gttctgtgtg cacaattggc aatccaagat   4500
ggatggattc aacacaggga tatagcgagc tacgtggtgg tgcgaggata tagcaacgga   4560
tatttatgtt tgacacttga gaatgtacga tacaagcact gtccaagtac aatactaaac   4620
atactgtaca tactcatact cgtacccggg caacggtttc acttgagtgc agtggctagt   4680
gctcttactc gtacagtgtg caatactgcg tatcatagtc tttgatgtat atcgtattca   4740
ttcatgttag ttgcgtacgc caccattctg tctgccgcca tgatgctcaa gttctctctt   4800
aacatgaagc ccgccggtga cgctgttgag gctgccgtca aggagtccgt cgaggctggt   4860
atcactaccg ccgatatcgg aggctcttcc tccacctccg aggtcggaga cttgttgcca   4920
acaaggtcaa ggagctgctc aagaaggagt aagtcgtttc tacgacgcat tgatggaagg   4980
agcaaactga cgcgcctgcg ggttggtcta ccggcagggt ccgctagtgt ataagactct   5040
ataaaaaggg ccctgccctg ctaatgaaat gatgatttat aatttaccgg tgtagcaacc   5100
ttgactagaa gaagcagatt gggtgtgttt gtagtggagg acagtggtac gttttggaaa   5160
cagtcttctt gaaagtgtct tgtctacagt atattcactc ataacctcaa tagccaaggg   5220
tgtagtcggt ttattaaagg aagggagttg tggctgatgt ggatagatat ctttaagctg   5280
gcgactgcac ccaacgagtg tggtggtagc ttgttactgt atattcggta agatatattt   5340
tgtggggttt tagtggtgtt tggtaggtta gtgcttggta tatgagttgt aggcatgaca   5400
atttggaaag gggtggactt tgggaatatt gtgggatttc aataccttag tttgtacagg   5460
gtaattgtta caaatgatac aaagaactgt atttcttttc atttgtttta attggttgta   5520
tatcaagtcc gttagacgag ctcagtgggc gcgccagctg cattaatgaa tcggccaacg   5580
cgcggggaga ggcggtttgc gtattgggcg ctcttccgct tcctcgctca ctgactcgct   5640
gcgctcggtc gttcggctgc ggcgagcggt atcagctcac tcaaaggcgg taatacggtt   5700
atccacagaa tcaggggata acgcaggaaa gaacatgtga gcaaaaggcc agcaaaaggc   5760
caggaaccgt aaaaaggccg cgttgctggc gtttttccat aggctccgcc cccctgacga   5820
gcatcacaaa aatcgacgct caagtcagag gtggcgaaac ccgacaggac tataaagata   5880
ccaggcgttt ccccctggaa gctccctcgt gcgctctcct gttccgaccc tgccgcttac   5940
cggatacctg tccgcctttc tcccttcggg aagcgtggcg ctttctcata gctcacgctg   6000
taggtatctc agttcggtgt aggtcgttcg ctccaagctg ggctgtgtgc acgaaccccc   6060
cgttcagccc gaccgctgcg ccttatccgg taactatcgt cttgagtcca acccggtaag   6120
acacgactta tcgccactgg cagcagccac tggtaacagg attagcagag cgaggtatgt   6180
aggcggtgct acagagttct tgaagtggtg gcctaactac ggctacacta gaagaacagt   6240
atttggtatc tgcgctctgc tgaagccagt taccttcgga aaaagagttg gtagctcttg   6300
atccggcaaa caaaccaccg ctggtagcgg tggttttttt gtttgcaagc agcagattac   6360
gcgcagaaaa aaaggatctc aagaagatcc tttgatcttt tctacggggt ctgacgctca   6420
gtggaacgaa aactcacgtt aagggatttt ggtcatgaga ttatcaaaaa ggatcttcac   6480
ctagatcctt ttaaattaaa aatgaagttt taaatcaatc taaagtatat atgagtaaac   6540
ttggtctgac agttaccaat gcttaatcag tgaggcacct atctcagcga tctgtctatt   6600
tcgttcatcc atagttgcct gactccccgt cgtgtagata actacgatac gggagggctt   6660
accatctggc cccagtgctg caatgatacc gcgagaccca cgctcaccgg ctccagattt   6720
```

-continued

```
atcagcaata aaccagccag ccggaagggc cgagcgcaga agtggtcctg caactttatc   6780
cgcctccatc cagtctatta attgttgccg ggaagctaga gtaagtagtt cgccagttaa   6840
tagtttgcgc aacgttgttg ccattgctac aggcatcgtg gtgtcacgct cgtcgtttgg   6900
tatggcttca ttcagctccg gttcccaacg atcaaggcga gttacatgat cccccatgtt   6960
gtgcaaaaaa gcggttagct ccttcggtcc tccgatcgtt gtcagaagta agttggccgc   7020
agtgttatca ctcatggtta tggcagcact gcataattct cttactgtca tgccatccgt   7080
aagatgcttt tctgtgactg gtgagtactc aaccaagtca ttctgagaat agtgtatgcg   7140
gcgaccgagt tgctcttgcc cggcgtcaat acgggataat accgcgccac atagcagaac   7200
tttaaaagtg ctcatcattg gaaaacgttc ttcggggcga aaactctcaa ggatcttacc   7260
gctgttgaga tccagttcga tgtaacccac tcgtgcaccc aactgatctt cagcatcttt   7320
tactttcacc agcgtttctg ggtgagcaaa aacaggaagg caaaatgccg caaaaaaggg   7380
aataagggcg acacggaaat gttgaatact catactcttc ctttttcaat attattgaag   7440
catttatcag ggttattgtc tcatgagcgg atacatattt gaatgtattt agaaaaataa   7500
acaaataggg gttccgcgca catttccccg aaaagtgcca cctgatgcgg tgtgaaatac   7560
cgcacagatg cgtaaggaga aaataccgca tcaggaaatt gtaagcgtta atattttgtt   7620
aaaattcgcg ttaaattttt gttaaatcag ctcatttttt aaccaatagg ccgaaatcgg   7680
caaaatccct tataaatcaa aagaatagac cgagataggg ttgagtgttg ttccagtttg   7740
gaacaagagt ccactattaa agaacgtgga ctccaacgtc aaagggcgaa aaaccgtcta   7800
tcagggcgat ggcccactac gtgaaccatc accctaatca agttttttgg ggtcgaggtg   7860
ccgtaaagca ctaaatcgga accctaaagg gagcccccga tttagagctt gacggggaaa   7920
gccggcgaac gtggcgagaa aggaagggaa gaaagcgaaa ggagcgggcg ctagggcgct   7980
ggcaagtgta gcggtcacgc tgcgcgtaac caccacaccc gccgcgctta atgcgccgct   8040
acagggcgcg tccattcgcc attcaggctg cgcaactgtt gggaagggcg atcggtgcgg   8100
gcctcttcgc tattacgcca gctggcgaaa gggggatgtg ctgcaaggcg attaagttgg   8160
gtaacgccag ggttttccca gtcacgacgt tgtaaaacga cggccagtga attgtaatac   8220
gactcactat agggcgaatt gggcccgacg tcgcatgcta tcggcatcga caaggtttgg   8280
gtccctagcc gataccgcac tacctgagtc acaatcttcg gaggtttagt cttccacata   8340
gcacgggcaa aagtgcgtat atatacaaga gcgtttgcca gccacagatt ttcactccac   8400
acaccacatc acacatacaa ccacacacat ccacaatgga acccgaaact aagaagacca   8460
agactgactc caagaagatt gttcttctcg gcggcgactt ctgtggcccc gaggtgattg   8520
ccgaggccgt caaggtgctc aagtctgttg ctgaggcctc cggcaccgag tttgtgtttg   8580
aggaccgact cattggagga gctgccattg agaaggaggg cgagcccatc accgacgcta   8640
ctctcgacat ctgccgaaag gctgactcta ttatgctcgg tgctgtcgga ggcgctgcca   8700
acaccgtatg gaccactccc gacggacgaa ccgacgtgcg acccgagcag ggtctcctca   8760
agctgcgaaa ggacctgaac ctgtacgcca acctgcgacc ctgccagctg ctgtcgccca   8820
agctcgccga tctctccccc atccgaaacg ttgagggcac cgacttcatc attgtccgag   8880
agctcgtcgg aggtatctac tttggagagc gaaaggagga tgacggatct ggcgtcgctt   8940
ccgacaccga gacctactcc gttaattaat ttgaatcgaa tcgatgagcc taaaatgaac   9000
ccgagtatat ctcataaaat tctcggtgag aggtctgtga ctgtcagtac aaggtgcctt   9060
cattatgccc tcaaccttac catacctcac tgaatgtagt gtacctctaa aatgaaata    9120
```

```
cagtgccaaa agccaaggca ctgagctcgt ctaacggact tgatatacaa ccaattaaaa   9180
caaatgaaaa gaaatacagt tctttgtatc atttgtaaca attaccctgt acaaactaag   9240
gtattgaaat cccacaatat tcccaaagtc cacccctttc caaattgtca tgcctacaac   9300
tcatatacca agcactaacc taccgtttaa acagtgtacg cagatctggt gtagtggtag   9360
tgcagtggtg gtattgtgac tggggatgta gttgagaata agtcatacac aagtcagctt   9420
tcttcgagcc tcatataagt ataagtagtt caacgtatta gcactgtacc cagcatctcc   9480
gtatcgagaa acacaacaac atgccccatt ggacagatca tgcggataca caggttgtgc   9540
agtatcatac atactcgatc agacaggtcg tctgaccatc atacaagctg aacaagcgct   9600
ccatacttgc acgctctcta tatacacagt taaattacat atccatagtc taacctctaa   9660
cagttaatct tctggtaagc ctcccagcca gccttctggt atcgcttggc ctcctcaata   9720
ggatctcggt tctggccgta cagacctcgg ccgacaatta tgatatccgt tccggtagac   9780
atgacatcct caacagttcg gtactgctgt ccgagagcgt ctcccttgtc gtcaagaccc   9840
accccggggg tcagaataag ccagtcctca gagtcgccct taggtcggtt ctgggcaatg   9900
aagccaacca caaactcggg gtcggatcgg gcaagctcaa tggtctgctt ggagtactcg   9960
ccagtggcca gagagccctt gcaagacagc tcggccagca tgagcagacc tctggccagc  10020
ttctcgttgg gagaggggac taggaactcc ttgtactggg agttctcgta gtcagagacg  10080
tcctccttct tctgttcaga gacagtttcc tcggcaccag ctcgcaggcc agcaatgatt  10140
ccggttccgg gtacaccgtg ggcgttggtg atatcggacc actcggcgat tcggtgacac  10200
cggtactggt gcttgacagt gttgccaata tctgcgaact ttctgtcctc gaacaggaag  10260
aaaccgtgct taagagcaag ttccttgagg gggagcacag tgccggcgta ggtgaagtcg  10320
tcaatgatgt cgatatgggt tttgatcatg cacacataag gtccgacctt atcggcaagc  10380
tcaatgagct ccttggtggt ggtaacatcc agagaagcac acaggttggt tttcttggct  10440
gccacgagct tgagcactcg agcggcaaag gcggacttgt ggacgttagc tcgagcttcg  10500
taggagggca ttttggtggt gaagaggaga ctgaaataaa tttagtctgc agaacttttt  10560
atcggaacct tatctggggc agtgaagtat atgttatggt aatagttacg agttagttga  10620
acttatagat agactggact atacggctat cggtccaaat tagaaagaac gtcaatggct  10680
ctctgggcgt cgcctttgcc gacaaaaatg tgatcatgat gaaagccagc aatgacgttg  10740
cagctgatat tgttgtcggc caaccgcgcc gaaaacgcag ctgtcagacc cacagcctcc  10800
aacgaagaat gtatcgtcaa agtgatccaa gcacactcat agttggagtc gtactccaaa  10860
ggcggcaatg acgagtcaga cagatactcg tcgacctttt ccttgggaac caccaccgtc  10920
agcccttctg actcacgtat tgtag                                        10945
```

<210> SEQ ID NO 24
<211> LENGTH: 1341
<212> TYPE: DNA
<213> ORGANISM: Mortierella alpina AF067654
<220> FEATURE:
<221> NAME/KEY: misc_feature
<223> OTHER INFORMATION: delta-5 desaturase

<400> SEQUENCE: 24

```
atgggaacgg accaaggaaa aaccttcacc tgggaagagc tggcggccca taacaccaag     60
gacgacctac tcttggccat ccgcggcagg gtgtacgatg tcacaaagtt cttgagccgc    120
catcctggtg gagtggacac tctcctgctc ggagctggcc gagatgttac tccggtcttt    180
```

-continued

```
gagatgtatc acgcgtttgg ggctgcagat gccattatga agaagtacta tgtcggtaca    240
ctggtctcga atgagctgcc catcttcccg gagccaacgg tgttccacaa aaccatcaag    300
acgagagtcg agggctactt tacggatcgg aacattgatc ccaagaatag accagagatc    360
tggggacgat acgctcttat ctttggatcc ttgatcgctt cctactacgc gcagctcttt    420
gtgcctttcg ttgtcgaacg cacatggctt caggtggtgt ttgcaatcat catgggattt    480
gcgtgcgcac aagtcggact caaccctctt catgatgcgt ctcacttttc agtgacccac    540
aaccccactg tctggaagat tctgggagcc acgcacgact tttttcaacgg agcatcgtac    600
ctggtgtgga tgtaccaaca tatgctcggc catcacccct acaccaacat tgctggagca    660
gatcccgacg tgtcgacgtc tgagcccgat gttcgtcgta tcaagcccaa ccaaaagtgg    720
tttgtcaacc acatcaacca gcacatgttt gttcctttcc tgtacggact gctggcgttc    780
aaggtgcgca ttcaggacat caacattttg tactttgtca agaccaatga cgctattcgt    840
gtcaatccca tctcgacatg gcacactgtg atgttctggg gcggcaaggc tttctttgtc    900
tggtatcgcc tgattgttcc cctgcagtat ctgcccctgg gcaaggtgct gctcttgttc    960
acggtcgcgg acatggtgtc gtcttactgg ctggcgctga ccttccaggc gaaccacgtt   1020
gttgaggaag ttcagtggcc gttgcctgac gagaacggga tcatccaaaa ggactgggca   1080
gctatgcagg tcgagactac gcaggattac gcacacgatt cgcacctctg gaccagcatc   1140
actggcagct tgaactacca ggctgtgcac catctgttcc ccaacgtgtc gcagcaccat   1200
tatcccgata ttctggccat catcaagaac acctgcagcg agtacaaggt tccatacctt   1260
gtcaaggata cgttttggca agcatttgct tcacatttgg agcacttgcg tgttcttgga   1320
ctccgtccca aggaagagta g                                              1341
```

<210> SEQ ID NO 25
<211> LENGTH: 446
<212> TYPE: PRT
<213> ORGANISM: Mortierella alpina AF067654

<400> SEQUENCE: 25

```
Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160
```

-continued

```
Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
    370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
            420                 425                 430

Leu Glu His Leu Arg Val Leu Gly Leu Arg Pro Lys Glu Glu
        435                 440                 445
```

<210> SEQ ID NO 26
<211> LENGTH: 12690
<212> TYPE: DNA
<213> ORGANISM: Artificial Sequence
<220> FEATURE:
<223> OTHER INFORMATION: Plasmid pZP3L37

<400> SEQUENCE: 26

```
aaataccagt tggccacaaa cccttgacga tctcgtatgt cccctccgac atactcccgg     60

ccggctgggg tacgttcgat agcgctatcg gcatcgacaa ggtttgggtc cctagccgat    120

accgcactac ctgagtcaca atcttcggag gtttagtctt ccacatagca cgggcaaaag    180

tgcgtatata tacaagagcg tttgccagcc acagattttc actccacaca ccacatcaca    240

catacaacca cacacatcca caatggaacc cgaaactaag aagaccaaga ctgactccaa    300

gaagattgtt cttctcggcg gcgacttctg tggccccgag gtgattgccg aggccgtcaa    360

ggtgctcaag tctgttgctg aggcctccgg caccgagttt gtgtttgagg accgactcat    420

tggaggagct gccattgaga aggagggcga gcccatcacc gacgctactc tcgacatctg    480
```

-continued

```
ccgaaaggct gactctatta tgctcggtgc tgtcggaggc gctgccaaca ccgtatggac    540
cactcccgac ggacgaaccg acgtgcgacc cgagcagggt ctcctcaagc tgcgaaagga    600
cctgaacctg tacgccaacc tgcgaccctg ccagctgctg tcgcccaagc tcgccgatct    660
ctcccccatc cgaaacgttg agggcaccga cttcatcatt gtccgagagc tcgtcggagg    720
tatctacttt ggagagcgaa aggaggatga cggatctggc gtcgcttccg acaccgagac    780
ctactccgtt cctgaggttg agcgaattgc ccgaatggcc gccttcctgg cccttcagca    840
caaccccccct cttcccgtgt ggtctcttga caaggccaac gtgctggcct cctctcgact    900
ttggcgaaag actgtcactc gagtcctcaa ggacgaattc ccccagctcg agctcaacca    960
ccagctgatc gactcggccg ccatgatcct catcaagcag ccctccaaga tgaatggtat   1020
catcatcacc accaacatgt ttggcgatat catctccgac gaggcctccg tcatccccgg   1080
ttctctgggt ctgctgccct ccgcctctct ggcttctctg cccgacacca acgaggcgtt   1140
cggtctgtac gagccctgtc acggatctgc ccccgatctc ggcaagcaga aggtcaaccc   1200
cattgccacc attctgtctg ccgccatgat gctcaagttc tctcttaaca tgaagcccgc   1260
cggtgacgct gttgaggctg ccgtcaagga gtccgtcgag gctggtatca ctaccgccga   1320
tatcggaggc tcttcctcca cctccgaggt cggagacttg ttgccaacaa ggtcaaggag   1380
ctgctcaaga aggagtaagt cgtttctacg acgcattgat ggaaggagca aactgacgcg   1440
cctgcgggtt ggtctaccgg cagggtccgc tagtgtataa gactctataa aaagggccct   1500
gccctgctaa tgaaatgatg atttataatt taccggtgta gcaaccttga ctagaagaag   1560
cagattgggt gtgtttgtag tggaggacag tggtacgttt tggaaacagt cttcttgaaa   1620
gtgtcttgtc tacagtatat tcactcataa cctcaatagc caagggtgta gtcggtttat   1680
taaaggaagg gagttgtggc tgatgtggat agatatcttt aagctggcga ctgcacccaa   1740
cgagtgtggt ggtagcttgt tagatctgta tattcggtaa gatatatttt gtggggtttt   1800
agtggtgttt aaacagtgta cgcagtacta tagaggaaca attgccccgg agaagacggc   1860
caggccgcct agatgacaaa ttcaacaact cacagctgac tttctgccat tgccactagg   1920
ggggggcctt tttatatggc caagccaagc tctccacgtc ggttgggctg cacccaacaa   1980
taaatgggta gggttgcacc aacaaaggga tgggatgggg ggtagaagat acgaggataa   2040
cggggctcaa tggcacaaat aagaacgaat actgccatta agactcgtga tccagcgact   2100
gacaccattg catcatctaa gggcctcaaa actacctcgg aactgctgcg ctgatctgga   2160
caccacagag gttccgagca ctttaggttg caccaaatgt cccaccaggt gcaggcagaa   2220
aacgctggaa cagcgtgtac agtttgtctt aacaaaaagt gagggcgctg aggtcgagca   2280
gggtggtgtg acttgttata gcctttagag ctgcgaaagc gcgtatggat ttggctcatc   2340
aggccagatt gagggtctgt ggacacatgt catgttagtg tacttcaatc gccccctgga   2400
tatagccccg acaataggcc gtggcctcat ttttttgcct tccgcacatt tccattgctc   2460
ggtacccaca ccttgcttct cctgcacttg ccaaccttaa tactggttta cattgaccaa   2520
catcttacaa gcgggggct tgtctagggt atatataaac agtggctctc ccaatcggtt   2580
gccagtctct tttttccttt ctttccccac agattcgaaa tctaaactac acatcacaca   2640
atgcctgtta ctgacgtcct taagcgaaag tccggtgtca tcgtcggcga cgatgtccga   2700
gccgtgagta tccacgacaa gatcagtgtc gagacgacgc gttttgtgta atgacacaat   2760
ccgaaagtcg ctagcaacac acactctcta cacaaactaa cccagctctc catggctgag   2820
```

-continued

```
gataagacca aggtcgagtt ccctaccctg actgagctga agcactctat ccctaacgct   2880
tgctttgagt ccaacctcgg actctcgctc tactacactg cccgagcgat cttcaacgca   2940
tctgcctctg ctgctctgct ctacgctgcc cgatctactc ccttcattgc cgataacgtt   3000
ctgctccacg ctctggtttg cgccacctac atctacgtgc agggtgtcat cttctggggt   3060
ttctttaccg tcggtcacga ctgtggtcac tctgccttct cccgatacca ctccgtcaac   3120
ttcatcattg gctgcatcat gcactctgcc attctgactc ccttcgagtc ctggcgagtg   3180
acccaccgac accatcacaa gaacactggc aacattgata aggacgagat cttctaccct   3240
catcggtccg tcaaggacct ccaggacgtg cgacaatggg tctacaccct cggaggtgct   3300
tggtttgtct acctgaaggt cggatatgct cctcgaacca tgtcccactt tgacccctgg   3360
gaccctctcc tgcttcgacg agcctccgct gtcatcgtgt ccctcggagt ctgggctgcc   3420
ttcttcgctg cctacgccta cctcacatac tcgctcggct ttgccgtcat gggcctctac   3480
tactatgctc ctctctttgt ctttgcttcg ttcctcgtca ttactacctt cttgcatcac   3540
aacgacgaag ctactccctg gtacggtgac tcggagtgga cctacgtcaa gggcaacctg   3600
agctccgtcg accgatcgta cggagctttc gtggacaacc tgtctcacca cattggcacc   3660
caccaggtcc atcacttgtt ccctatcatt ccccactaca agctcaacga agccaccaag   3720
cactttgctg ccgcttaccc tcacctcgtg agacgtaacg acgagcccat cattactgcc   3780
ttcttcaaga ccgctcacct ctttgtcaac tacggagctg tgcccgagac tgctcagatt   3840
ttcaccctca aagagtctgc cgctgcagcc aaggccaaga gcgactaagc ggccgctatt   3900
tatcactctt tacaacttct acctcaacta tctactttaa taaatgaata tcgtttattc   3960
tctatgatta ctgtatatgc gttcctctaa gacaaatcga aaccagcatg tgatcgaatg   4020
gcatacaaaa gtttcttccg aagttgatca atgtcctgat agtcaggcag cttgagaaga   4080
ttgacacagg tggaggccgt agggaaccga tcaacctgtc taccagcgtt acgaatggca   4140
aatgacgggt tcaaagcctt gaatccttgc aatggtgcct tggatactga tgtcacaaac   4200
ttaagaagca gccgcttgtc ctcttcctcg atcgatcagg agagaccggg ttggcggcgt   4260
atttgtgtcc caaaaaacag ccccaattgc cccaattgac cccaaattga cccagtagcg   4320
ggcccaaccc cggcgagagc ccccttcacc ccacatatca aacctccccc ggttcccaca   4380
cttgccgtta agggcgtagg gtactgcagt ctggaatcta cgcttgttca gactttgtac   4440
tagtttcttt gtctggccat ccgggtaacc catgccggac gcaaaataga ctactgaaaa   4500
tttttttgct ttgtggttgg gactttagcc aagggtataa aagaccaccg tccccgaatt   4560
acctttcctc ttcttttctc tctctccttg tcaactcaca cccgaaatcg ttaagcattt   4620
ccttctgagt ataagaatca ttcaccatgg ctgaggataa gaccaaggtc gagttcccta   4680
ccctgactga gctgaagcac tctatcccta acgcttgctt tgagtccaac ctcggactct   4740
cgctctacta cactgcccga gcgatcttca acgcatctgc ctctgctgct ctgctctacg   4800
ctgcccgatc tactcccttc attgccgata acgttctgct ccacgctctg gtttgcgcca   4860
cctacatcta cgtgcagggt gtcatcttct ggggtttctt taccgtcggt cacgactgtg   4920
gtcactctgc cttctcccga taccactccg tcaacttcat cattggctgc atcatgcact   4980
ctgccattct gactcccttc gagtcctggc gagtgaccca ccgacaccat cacaagaaca   5040
ctggcaacat tgataaggac gagatcttct accctcatcg gtccgtcaag gacctccagg   5100
acgtgcgaca atgggtctac accctcggag gtgcttggtt tgtctacctg aaggtcggat   5160
atgctcctcg aaccatgtcc cactttgacc cctgggaccc tctcctgctt cgacgagcct   5220
```

-continued

```
ccgctgtcat cgtgtccctc ggagtctggg ctgccttctt cgctgcctac gcctacctca   5280
catactcgct cggctttgcc gtcatgggcc tctactacta tgctcctctc tttgtctttg   5340
cttcgttcct cgtcattact accttcttgc atcacaacga cgaagctact ccctggtacg   5400
gtgactcgga gtggacctac gtcaagggca acctgagctc cgtcgaccga tcgtacggag   5460
ctttcgtgga caacctgtct caccacattg gcacccacca ggtccatcac ttgttcccta   5520
tcattcccca ctacaagctc aacgaagcca ccaagcactt tgctgccgct taccctcacc   5580
tcgtgagacg taacgacgag cccatcatta ctgccttctt caagaccgct cacctctttg   5640
tcaactacgg agctgtgccc gagactgctc agattttcac cctcaaagag tctgccgctg   5700
cagccaaggc caagagcgac taagcggccg caagtgtgga tggggaagtg agtgcccggt   5760
tctgtgtgca caattggcaa tccaagatgg atggattcaa cacagggata tagcgagcta   5820
cgtggtggtg cgaggatata gcaacggata tttatgtttg acacttgaga atgtacgata   5880
caagcactgt ccaagtacaa tactaaacat actgtacata ctcatactcg tacccgggca   5940
acggtttcac ttgagtgcag tggctagtgc tcttactcgt acagtgtgca atactgcgta   6000
tcatagtctt tgatgtatat cgtattcatt catgttagtt gcgtacggtg tgtatcgtag   6060
aggtagtgac gtgttgtcca cagggcgact gtgtccgtgt atatatatat tcctcggccc   6120
gagcttattt gtgtggggtt gaggaaatca aaccaaatcg gtagtcagag aaataaaaca   6180
aaaagaaata aaaagaaata gaggacgcac aacgccatca ccgtcggaga gacaggagaa   6240
gggaaaatgg gcaaaaatgc ccttatcaca cccgcccgct ttgtgctctc attcggctcc   6300
cacaagagcc tcttgtcctg gttccccccc cccacatttt aacaccccac acgacgttgc   6360
tgcacgtgga attttcggcc gaaaacctgt ggggtactta cttttggcac tggagagaag   6420
catctgggat tttgggaacc taggcagaag atgaggaaaa aaataagagg aaccgttgtg   6480
agcttgctta tcagtgtcat atactccccc ctccttgcgt tttgcgtctt tttcccccta   6540
tttttcaaat tttgcgattt tttttctctt tttttccgct tttttccgct ttttttttgg   6600
ccggctttta tccatttctc caagccgagg atcacatcta tgcagcccag tccgttggag   6660
catatctgcg gtagagtttc ggaacggcgt taagcactgt gtccgggtcg gtctggaacg   6720
agattgagcg ggaaattcgg gggaataaga ccaccgttgg actccccgca atgaggagat   6780
caagatgtgc ttttcagaat tctgattggt ggcgcgccag ctgcattaat gaatcggcca   6840
acgcgcgggg agaggcggtt tgcgtattgg gcgctcttcc gcttcctcgc tcactgactc   6900
gctgcgctcg gtcgttcggc tgcggcgagc ggtatcagct cactcaaagg cggtaatacg   6960
gttatccaca gaatcagggg ataacgcagg aaagaacatg tgagcaaaag gccagcaaaa   7020
ggccaggaac cgtaaaaagg ccgcgttgct ggcgtttttc cataggctcc gcccccctga   7080
cgagcatcac aaaaatcgac gctcaagtca gaggtggcga aacccgacag gactataaag   7140
ataccaggcg tttccccctg gaagctccct cgtgcgctct cctgttccga ccctgccgct   7200
taccggatac ctgtccgcct ttctcccttc gggaagcgtg gcgctttctc atagctcacg   7260
ctgtaggtat ctcagttcgg tgtaggtcgt tcgctccaag ctgggctgtg tgcacgaacc   7320
ccccgttcag cccgaccgct gcgccttatc cggtaactat cgtcttgagt ccaacccggt   7380
aagacacgac ttatcgccac tggcagcagc cactggtaac aggattagca gagcgaggta   7440
tgtaggcggt gctacagagt tcttgaagtg gtggcctaac tacggctaca ctagaagaac   7500
agtatttggt atctgcgctc tgctgaagcc agttaccttc ggaaaaagag ttggtagctc   7560
```

-continued

```
ttgatccggc aaacaaacca ccgctggtag cggtggtttt tttgtttgca agcagcagat   7620
tacgcgcaga aaaaaaggat ctcaagaaga tcctttgatc ttttctacgg ggtctgacgc   7680
tcagtggaac gaaaactcac gttaagggat tttggtcatg agattatcaa aaaggatctt   7740
cacctagatc cttttaaatt aaaaatgaag ttttaaatca atctaaagta tatatgagta   7800
aacttggtct gacagttacc aatgcttaat cagtgaggca cctatctcag cgatctgtct   7860
atttcgttca tccatagttg cctgactccc cgtcgtgtag ataactacga tacgggaggg   7920
cttaccatct ggccccagtg ctgcaatgat accgcgagac ccacgctcac cggctccaga   7980
tttatcagca ataaaccagc cagccggaag ggccgagcgc agaagtggtc ctgcaacttt   8040
atccgcctcc atccagtcta ttaattgttg ccgggaagct agagtaagta gttcgccagt   8100
taatagtttg cgcaacgttg ttgccattgc tacaggcatc gtggtgtcac gctcgtcgtt   8160
tggtatggct tcattcagct ccggttccca acgatcaagg cgagttacat gatcccccat   8220
gttgtgcaaa aaagcggtta gctccttcgg tcctccgatc gttgtcagaa gtaagttggc   8280
cgcagtgtta tcactcatgg ttatggcagc actgcataat tctcttactg tcatgccatc   8340
cgtaagatgc ttttctgtga ctggtgagta ctcaaccaag tcattctgag aatagtgtat   8400
gcggcgaccg agttgctctt gcccggcgtc aatacgggat aataccgcgc cacatagcag   8460
aactttaaaa gtgctcatca ttggaaaacg ttcttcgggg cgaaaactct caaggatctt   8520
accgctgttg agatccagtt cgatgtaacc cactcgtgca cccaactgat cttcagcatc   8580
ttttactttc accagcgttt ctgggtgagc aaaaacagga aggcaaaatg ccgcaaaaaa   8640
gggaataagg gcgacacgga aatgttgaat actcatactc ttcctttttc aatattattg   8700
aagcatttat cagggttatt gtctcatgag cggatacata tttgaatgta tttagaaaaa   8760
taaacaaata ggggttccgc gcacatttcc ccgaaaagtg ccacctgatg cggtgtgaaa   8820
taccgcacag atgcgtaagg agaaaatacc gcatcaggaa attgtaagcg ttaatatttt   8880
gttaaaattc gcgttaaatt tttgttaaat cagctcattt tttaaccaat aggccgaaat   8940
cggcaaaatc ccttataaat caaaagaata gaccgagata gggttgagtg ttgttccagt   9000
ttggaacaag agtccactat taaagaacgt ggactccaac gtcaaagggc gaaaaaccgt   9060
ctatcagggc gatggcccac tacgtgaacc atcaccctaa tcaagttttt tggggtcgag   9120
gtgccgtaaa gcactaaatc ggaaccctaa agggagcccc cgatttagag cttgacgggg   9180
aaagccggcg aacgtggcga gaaaggaagg gaagaaagcg aaaggagcgg gcgctagggc   9240
gctggcaagt gtagcggtca cgctgcgcgt aaccaccaca cccgccgcgc ttaatgcgcc   9300
gctacagggc gcgtccattc gccattcagg ctgcgcaact gttgggaagg gcgatcggtg   9360
cgggcctctt cgctattacg ccagctggcg aaagggggat gtgctgcaag gcgattaagt   9420
tgggtaacgc cagggttttc ccagtcacga cgttgtaaaa cgacggccag tgaattgtaa   9480
tacgactcac tatagggcga attgggcccg acgtcgcatg cgtcgagata tcgacattgt   9540
tccatctcca gtttaacccc aacttatcga gagtatttgt gagacacgca ataaatgaat   9600
ttataccaat caaatccata ttctacgctg tctacatata gatacttttt gtcatctctt   9660
gccctactat ttcgtcgata tatgaaggat acgccaaccg aacccatact ccacgctaca   9720
cacgcgcctt ttcacgcatt tctggggaaa atagacaccc ttggtgtcac ctgaagaata   9780
tgaaagaaga tattcattgt attgagctgt agatctgtgt atttcttgac ctcatcaatg   9840
acttctgggc tctttacctc gaatcatggt ggtactgtac cacatctcaa caccttgtag   9900
cacacctatg ggaaaattga gactatgaat ggattcccgt gcccgtatta ctctactaat   9960
```

```
ttgatcttgg aacgcgaaaa tacgtttcta ggactccaaa gaatctcaac tcttgtcctt  10020
actaaatata ctacccatag ttgatggttt acttgaacag agaggacatg ttcacttgac  10080
ccaaagtttc tcgcatctct tggatatttg aacaacggcg tccactgacc gtcagttatc  10140
cagtcacaaa acccccacat tcatacattc ccatgtacgt ttacaaagtt ctcaattcca  10200
tcgtgcaaat caaaatcaca tctattcatt catcatatat aaacccatca tgtctactaa  10260
cactcacaac tccatagaaa acatcgactc agaacacacg ctccatctat tcctcgtcca  10320
gctcgcaaat gtcgtcatct taattaaaag gcgttgaaac agaatgagcc agacagcaag  10380
gacaaggtgg ccaacagcaa ggagtccaaa aagccctcta ttgacgagat ccacgatgtt  10440
attgctcatg aggtttccga gctcgatgct gggaagaaga agtgatttgt atataagaaa  10500
taaatgagat atagtaaagg agtgcaagag aatggcaagg tggtcaaatt ctatattact  10560
tgcagtcact ggttcctcgt tgacatgaat gaagttaccg ttggcatagc tgatttaata  10620
tataactgtc caactaactc tcacctagat ataacccatg tgtgtgtttc caatcatcaa  10680
tgcggccgct tagtcgctct tggccttggc tgcagcggca gactctttga gggtgaaaat  10740
ctgagcagtc tcgggcacag ctccgtagtt gacaaagagg tgagcggtct tgaagaaggc  10800
agtaatgatg ggctcgtcgt tacgtctcac gaggtgaggg taagcggcag caaagtgctt  10860
ggtggcttcg ttgagcttgt agtggggaat gatagggaac aagtgatgga cctggtgggt  10920
gccaatgtgg tgagacaggt tgtccacgaa agctccgtac gatcggtcga cggagctcag  10980
gttgcccttg acgtaggtcc actccgagtc accgtaccag ggagtagctt cgtcgttgtg  11040
atgcaagaag gtagtaatga cgaggaacga agcaaagaca aagagaggag catagtagta  11100
gaggcccatg acggcaaagc cgagcgagta tgtgaggtag gcgtaggcag cgaagaaggc  11160
agcccagact ccgagggaca cgatgacagc ggaggctcgt cgaagcagga gagggtccca  11220
ggggtcaaag tgggacatgg ttcgaggagc atatccgacc ttcaggtaga caaaccaagc  11280
acctccgagg gtgtagaccc attgtcgcac gtcctggagg tccttgacgg accgatgagg  11340
gtagaagatc tcgtccttat caatgttgcc agtgttcttg tgatggtgtc ggtgggtcac  11400
tcgccaggac tcgaagggag tcagaatggc agagtgcatg atgcagccaa tgatgaagtt  11460
gacggagtgg tatcgggaga aggcagagtg accacagtcg tgaccgacgg taaagaaacc  11520
ccagaagatg acaccctgca cgtagatgta ggtggcgcaa accagagcgt ggagcagaac  11580
gttatcggca atgaagggag tagatcgggc agcgtagagc agagcagcag aggcagatgc  11640
gttgaagatc gctcgggcag tgtagtagag cgagagtccg aggttggact caaagcaagc  11700
gttagggata gagtgcttca gctcagtcag ggtagggaac tcgaccttgg tcttatcctc  11760
agccatggta ccagagctgg gttagtttgt gtagagagtg tgtgttgcta gcgactttcg  11820
gattgtgtca ttacacaaaa cgcgtcgtct cgacactgat cttgtcgtgg atactcacgg  11880
ctcggaattc tgtgatgtgt agtttagatt tcgaatctgt ggggaaagaa aggaaaaaag  11940
agactggcaa ccgattggga gagccactgt ttatatatac cctagacaag ccccccgctt  12000
gtaagatgtt ggtcaatgta aaccagtatt aaggttggca agtgcaggag aagcaaggtg  12060
tgggtaccga gcaatggaaa tgtgcggaag gcaaaaaaat gaggccacgg cctattgtcg  12120
gggctatatc caggggggcga ttgaagtaca ctaacatgac atgtgtccac agaccctcaa  12180
tctggcctga tgagccaaat ccatacgcgc tttcgcagct ctaaaggcta taacaagtca  12240
caccaccctg ctcgacctca gcgccctcac tttttgttaa gacaaactgt acacgctgtt  12300
```

-continued

```
ccagcgtttt ctgcctgcac ctggtgggac atttggtgca acctaaagtg ctcggaacct  12360

ctgtggtgtc cagatcagcg cagcagttcc gaggtagttt tgaggccctt agatgatgca  12420

atggtgtcag tcgctggatc acgagtctta atggcagtat tcgttcttat ttgtgccatt  12480

gagccccgtt atcctcgtat cttctacccc ccatcccatc cctttgttgg tgcaacccta  12540

cccatttatt gttgggtgca gcccaaccga cgtggagagc ttggcttggc catataaaaa  12600

ggcccccccc tagtggcaat ggcagaaagt cagctgtgag ttgttgaatt tgtcatctag  12660

gcggcctggc cgtcttctcc ggggcaattt                                   12690
```

```
<210> SEQ ID NO 27
<211> LENGTH: 1077
<212> TYPE: DNA
<213> ORGANISM: Saprolegnia diclina
<220> FEATURE:
<221> NAME/KEY: misc_feature
<223> OTHER INFORMATION: synthetic delta-17 desaturase (codon-optimized)

<400> SEQUENCE: 27

atggctgagg ataagaccaa ggtcgagttc cctaccctga ctgagctgaa gcactctatc     60

cctaacgctt gctttgagtc caacctcgga ctctcgctct actacactgc ccgagcgatc    120

ttcaacgcat ctgcctctgc tgctctgctc tacgctgccc gatctactcc cttcattgcc    180

gataacgttc tgctccacgc tctggtttgc gccacctaca tctacgtgca gggtgtcatc    240

ttctggggtt tctttaccgt cggtcacgac tgtggtcact ctgccttctc ccgataccac    300

tccgtcaact tcatcattgg ctgcatcatg cactctgcca ttctgactcc cttcgagtcc    360

tggcgagtga cccaccgaca ccatcacaag aacactggca acattgataa ggacgagatc    420

ttctaccctc atcggtccgt caaggacctc caggacgtgc gacaatgggt ctacaccctc    480

ggaggtgctt ggtttgtcta cctgaaggtc ggatatgctc ctcgaaccat gtcccacttt    540

gacccctggg accctctcct gcttcgacga gcctccgctg tcatcgtgtc cctcggagtc    600

tgggctgcct tcttcgctgc ctacgcctac ctcacatact cgctcggctt tgccgtcatg    660

ggcctctact actatgctcc tctctttgtc tttgcttcgt tcctcgtcat tactaccttc    720

ttgcatcaca acgacgaagc tactccctgg tacggtgact cggagtggac ctacgtcaag    780

ggcaacctga gctccgtcga ccgatcgtac ggagctttcg tggacaacct gtctcaccac    840

attggcaccc accaggtcca tcacttgttc cctatcattc cccactacaa gctcaacgaa    900

gccaccaagc actttgctgc cgcttaccct cacctcgtga gacgtaacga cgagcccatc    960

attactgcct tcttcaagac cgctcacctc tttgtcaact acggagctgt gcccgagact   1020

gctcagattt tcaccctcaa agagtctgcc gctgcagcca aggccaagag cgactaa      1077
```

```
<210> SEQ ID NO 28
<211> LENGTH: 358
<212> TYPE: PRT
<213> ORGANISM: Saprolegnia diclina (ATCC #56851)

<400> SEQUENCE: 28

Met Ala Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
        35                  40                  45

Leu Leu Tyr Ala Ala Arg Ser Thr Pro Phe Ile Ala Asp Asn Val Leu
```

-continued

```
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
        195                 200                 205

Ala Tyr Leu Thr Tyr Ser Leu Gly Phe Ala Val Met Gly Leu Tyr Tyr
    210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His His Ile Gly Thr His Gln Val His His
        275                 280                 285

Leu Phe Pro Ile Ile Pro His Tyr Lys Leu Asn Glu Ala Thr Lys His
    290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
            340                 345                 350

Ala Lys Ala Lys Ser Asp
        355


<210> SEQ ID NO 29
<211> LENGTH: 924
<212> TYPE: DNA
<213> ORGANISM: Yarrowia lipolytica
<220> FEATURE:
<221> NAME/KEY: misc_feature
<223> OTHER INFORMATION: Promoter FBAINm

<400> SEQUENCE: 29

aaattgcccc ggagaagacg gccaggccgc ctagatgaca aattcaacaa ctcacagctg     60

actttctgcc attgccacta gggggggcc tttttatatg gccaagccaa gctctccacg    120

tcggttgggc tgcacccaac aataaatggg tagggttgca ccaacaaagg gatgggatgg    180

ggggtagaag atacgaggat aacggggctc aatggcacaa ataagaacga atactgccat    240

taagactcgt gatccagcga ctgacaccat tgcatcatct aagggcctca aaactacctc    300
```

-continued

```
ggaactgctg cgctgatctg gacaccacag aggttccgag cactttaggt tgcaccaaat    360
gtcccaccag gtgcaggcag aaaacgctgg aacagcgtgt acagtttgtc ttaacaaaaa    420
gtgagggcgc tgaggtcgag cagggtggtg tgacttgtta tagcctttag agctgcgaaa    480
gcgcgtatgg atttggctca tcaggccaga ttgagggtct gtggacacat gtcatgttag    540
tgtacttcaa tcgccccctg gatatagccc cgacaatagg ccgtggcctc atttttttgc    600
cttccgcaca tttccattgc tcggtaccca caccttgctt ctcctgcact tgccaacctt    660
aatactggtt tacattgacc aacatcttac aagcgggggg cttgtctagg gtatatataa    720
acagtggctc tcccaatcgg ttgccagtct ctttttttcct ttctttcccc acagattcga    780
aatctaaact acacatcaca gaattccgag ccgtgagtat ccacgacaag atcagtgtcg    840
agacgacgcg ttttgtgtaa tgacacaatc cgaaagtcgc tagcaacaca cactctctac    900
acaaactaac ccagctctgg tacc                                          924
```

<210> SEQ ID NO 30
<211> LENGTH: 8194
<212> TYPE: DNA
<213> ORGANISM: Artificial Sequence
<220> FEATURE:
<223> OTHER INFORMATION: Plasmid pY37/F15

<400> SEQUENCE: 30

```
ggccgcacaa tggcgactcg acagcgaact gccaccactg ttgtggtcga ggaccttccc     60
aaggtcactc ttgaggccaa gtctgaacct gtgttccccg atatcaagac catcaaggat    120
gccattcccg cgcactgctt ccagccctcg ctcgtcacct cattctacta cgtcttccgc    180
gattttgcca tggtctctgc cctcgtctgg gctgctctca cctacatccc cagcatcccc    240
gaccagaccc tccgcgtcgc agcttggatg gtctacggct tcgtccaggg tctgttctgc    300
accggtgtct ggattctcgg ccatgagtgc ggccacggtg ctttctctct ccacggaaag    360
gtcaacaatg tgaccggctg gttcctccac tcgttcctcc tcgtccccta cttcagctgg    420
aagtactctc accaccgcca ccaccgcttc accggccaca tggatctcga catggctttc    480
gtccccaaga ctgagcccaa gccctccaag tcgctcatga ttgctggcat tgacgtcgcc    540
gagcttgttg aggacacccc cgctgctcag atggtcaagc tcatcttcca ccagcttttc    600
ggatggcagg cgtacctctt cttcaacgct agctctggca agggcagcaa gcagtgggag    660
cccaagactg gcctctccaa gtggttccga gtcagtcact tcgagcctac cagcgctgtc    720
ttccgcccca acgaggccat cttcatcctc atctccgata tcggtcttgc tctaatggga    780
actgctctgt actttgcttc caagcaagtt ggtgtttcga ccattctctt cctctacctt    840
gttccctacc tgtgggttca ccactggctc gttgccatta cctacctcca ccaccaccac    900
accgagctcc ctcactacac cgctgagggc tggacctacg tcaagggagc tctcgccact    960
gtcgaccgtg agtttggctt catcggaaag cacctcttcc acggtatcat tgagaagcac   1020
gttgttcacc atctcttccc taagatcccc ttctacaagg ctgacgaggc caccgaggcc   1080
atcaagcccg tcattggcga ccactactgc cacgacgacc gaagcttcct gggccagctg   1140
tggaccatct tcggcacgct caagtacgtc gagcacgacc ctgcccgacc cggtgccatg   1200
cgatggaaca aggactaggc taggcggccg ccaccgcggc ccgaattccg gcctcttcgg   1260
ccgccaagcg acccgggtgg acgtctagag gtacctagca attaacagat agtttgccgg   1320
tgataattct cttaacctcc cacactcctt tgacataacg atttatgtaa cgaaactgaa   1380
```

-continued

```
atttgaccag atattgtgtc cgcggtggag ctccagcttt tgttcccttt agtgagggtt   1440
aatttcgagc ttggcgtaat catggtcata gctgtttcct gtgtgaaatt gttatccgct   1500
cacaattcca cacaacgtac gagccggaag cataaagtgt aaagcctggg gtgcctaatg   1560
agtgagctaa ctcacattaa ttgcgttgcg ctcactgccc gctttccagt cgggaaacct   1620
gtcgtgccag ctgcattaat gaatcggcca acgcgcgggg agaggcggtt tgcgtattgg   1680
gcgctcttcc gcttcctcgc tcactgactc gctgcgctcg gtcgttcggc tgcggcgagc   1740
ggtatcagct cactcaaagg cggtaatacg gttatccaca gaatcagggg ataacgcagg   1800
aaagaacatg tgagcaaaag gccagcaaaa ggccaggaac cgtaaaaagg ccgcgttgct   1860
ggcgtttttc cataggctcc gcccccctga cgagcatcac aaaaatcgac gctcaagtca   1920
gaggtggcga aacccgacag gactataaag ataccaggcg tttccccctg gaagctccct   1980
cgtgcgctct cctgttccga ccctgccgct taccggatac ctgtccgcct ttctcccttc   2040
gggaagcgtg gcgctttctc atagctcacg ctgtaggtat ctcagttcgg tgtaggtcgt   2100
tcgctccaag ctgggctgtg tgcacgaacc ccccgttcag cccgaccgct gcgccttatc   2160
cggtaactat cgtcttgagt ccaacccggt aagacacgac ttatcgccac tggcagcagc   2220
cactggtaac aggattagca gagcgaggta tgtaggcggt gctacagagt tcttgaagtg   2280
gtggcctaac tacggctaca ctagaaggac agtatttggt atctgcgctc tgctgaagcc   2340
agttaccttc ggaaaaagag ttggtagctc ttgatccggc aaacaaacca ccgctggtag   2400
cggtggtttt tttgtttgca agcagcagat tacgcgcaga aaaaaaggat ctcaagaaga   2460
tcctttgatc ttttctacgg ggtctgacgc tcagtggaac gaaaactcac gttaagggat   2520
tttggtcatg agattatcaa aaaggatctt cacctagatc cttttaaatt aaaaatgaag   2580
ttttaaatca atctaaagta tatatgagta aacttggtct gacagttacc aatgcttaat   2640
cagtgaggca cctatctcag cgatctgtct atttcgttca tccatagttg cctgactccc   2700
cgtcgtgtag ataactacga tacgggaggg cttaccatct ggccccagtg ctgcaatgat   2760
accgcgagac ccacgctcac cggctccaga tttatcagca ataaaccagc cagccggaag   2820
ggccgagcgc agaagtggtc ctgcaacttt atccgcctcc atccagtcta ttaattgttg   2880
ccgggaagct agagtaagta gttcgccagt taatagtttg cgcaacgttg ttgccattgc   2940
tacaggcatc gtggtgtcac gctcgtcgtt tggtatggct tcattcagct ccggttccca   3000
acgatcaagg cgagttacat gatcccccat gttgtgcaaa aaagcggtta gctccttcgg   3060
tcctccgatc gttgtcagaa gtaagttggc cgcagtgtta tcactcatgg ttatggcagc   3120
actgcataat tctcttactg tcatgccatc cgtaagatgc ttttctgtga ctggtgagta   3180
ctcaaccaag tcattctgag aatagtgtat gcggcgaccg agttgctctt gcccggcgtc   3240
aatacgggat aataccgcgc cacatagcag aactttaaaa gtgctcatca ttggaaaacg   3300
ttcttcgggg cgaaaactct caaggatctt accgctgttg agatccagtt cgatgtaacc   3360
cactcgtgca cccaactgat cttcagcatc ttttactttc accagcgttt ctgggtgagc   3420
aaaaacagga aggcaaaatg ccgcaaaaaa gggaataagg gcgacacgga aatgttgaat   3480
actcatactc ttcctttttc aatattattg aagcatttat cagggttatt gtctcatgag   3540
cggatacata tttgaatgta tttagaaaaa taaacaaata ggggttccgc gcacatttcc   3600
ccgaaaagtg ccacctgacg cgccctgtag cggcgcatta agcgcggcgg gtgtggtggt   3660
tacgcgcagc gtgaccgcta cacttgccag cgccctagcg cccgctcctt tcgctttctt   3720
cccttccttt ctcgccacgt tcgccggctt tccccgtcaa gctctaaatc gggggctccc   3780
```

-continued

```
tttagggttc cgatttagtg ctttacggca cctcgacccc aaaaaacttg attagggtga   3840
tggttcacgt agtgggccat cgccctgata gacggttttt cgccctttga cgttggagtc   3900
cacgttcttt aatagtggac tcttgttcca aactggaaca acactcaacc ctatctcggt   3960
ctattctttt gatttataag ggattttgcc gatttcggcc tattggttaa aaaatgagct   4020
gatttaacaa aaatttaacg cgaattttaa caaaatatta acgcttacaa tttccattcg   4080
ccattcaggc tgcgcaactg ttgggaaggg cgatcggtgc gggcctcttc gctattacgc   4140
cagctggcga aagggggatg tgctgcaagg cgattaagtt gggtaacgcc agggttttcc   4200
cagtcacgac gttgtaaaac gacggccagt gaattgtaat acgactcact atagggcgaa   4260
ttgggtaccg ggccccccct cgaggtcgat ggtgtcgata agcttgatat cgaattcatg   4320
tcacacaaac cgatcttcgc ctcaaggaaa cctaattcta catccgagag actgccgaga   4380
tccagtctac actgattaat ttcgggccca ataatttaaa aaaatcgtgt tatataatat   4440
tatatgtatt atatatatac atcatgatga tactgacagt catgtcccat tgctaaatag   4500
acagactcca tctgccgcct ccaactgatg ttctcaatat ttaaggggtc atctcgcatt   4560
gtttaataat aaacagactc catctaccgc ctccaaatga tgttctcaaa atatattgta   4620
tgaacttatt tttattactt agtattatta gacaacttac ttgctttatg aaaaacactt   4680
cctatttagg aaacaattta taatggcagt tcgttcattt aacaatttat gtagaataaa   4740
tgttataaat gcgtatggga aatcttaaat atggatagca taaatgatat ctgcattgcc   4800
taattcgaaa tcaacagcaa cgaaaaaaat cccttgtaca acataaatag tcatcgagaa   4860
atatcaacta tcaaagaaca gctattcaca cgttactatt gagattatta ttggacgaga   4920
atcacacact caactgtctt tctctcttct agaaatacag gtacaagtat gtactattct   4980
cattgttcat acttctagtc atttcatccc acatattcct tggatttctc tccaatgaat   5040
gacattctat cttgcaaatt caacaattat aataagatat accaaagtag cggtatagtg   5100
gcaatcaaaa agcttctctg gtgtgcttct cgtatttatt tttattctaa tgatccatta   5160
aaggtatata tttatttctt gttatataat ccttttgttt attacatggg ctggatacat   5220
aaaggtattt tgatttaatt ttttgcttaa attcaatccc ccctcgttca gtgtcaactg   5280
taatggtagg aaattaccat acttttgaag aagcaaaaaa aatgaaagaa aaaaaaaatc   5340
gtatttccag gttagacgtt ccgcagaatc tagaatgcgg tatgcggtac attgttcttc   5400
gaacgtaaaa gttgcgctcc ctgagatatt gtacattttt gcttttacaa gtacaagtac   5460
atcgtacaac tatgtactac tgttgatgca tccacaacag tttgttttgt tttttttgt    5520
ttttttttt tctaatgatt cattaccgct atgtatacct acttgtactt gtagtaagcc    5580
gggttattgg cgttcaatta atcatagact tatgaatctg cacggtgtgc gctgcgagtt   5640
acttttagct tatgcatgct acttgggtgt aatattggga tctgttcgga aatcaacgga   5700
tgctcaaccg atttcgacag taattaatta agtcatacac aagtcagctt tcttcgagcc   5760
tcatataagt ataagtagtt caacgtatta gcactgtacc cagcatctcc gtatcgagaa   5820
acacaacaac atgccccatt ggacagatca tgcggataca caggttgtgc agtatcatac   5880
atactcgatc agacaggtcg tctgaccatc atacaagctg aacaagcgct ccatacttgc   5940
acgctctcta tatacacagt taaattacat atccatagtc taacctctaa cagttaatct   6000
tctggtaagc ctcccagcca gccttctggt atcgcttggc ctcctcaata ggatctcggt   6060
tctggccgta cagacctcgg ccgacaatta tgatatccgt tccggtagac atgacatcct   6120
```

-continued

```
caacagttcg gtactgctgt ccgagagcgt ctcccttgtc gtcaagaccc accccggggg   6180
tcagaataag ccagtcctca gagtcgccct taggtcggtt ctgggcaatg aagccaacca   6240
caaactcggg gtcggatcgg gcaagctcaa tggtctgctt ggagtactcg ccagtggcca   6300
gagagccctt gcaagacagc tcggccagca tgagcagacc tctggccagc ttctcgttgg   6360
gagaggggac taggaactcc ttgtactggg agttctcgta gtcagagacg tcctccttct   6420
tctgttcaga gacagtttcc tcggcaccag ctcgcaggcc agcaatgatt ccggttccgg   6480
gtacaccgtg ggcgttggtg atatcggacc actcggcgat tcggtgacac cggtactggt   6540
gcttgacagt gttgccaata tctgcgaact ttctgtcctc gaacaggaag aaaccgtgct   6600
taagagcaag ttccttgagg gggagcacag tgccggcgta ggtgaagtcg tcaatgatgt   6660
cgatatgggt tttgatcatg cacacataag gtccgacctt atcggcaagc tcaatgagct   6720
ccttggtggt ggtaacatcc agagaagcac acaggttggt tttcttggct gccacgagct   6780
tgagcactcg agcggcaaag gcggacttgt ggacgttagc tcgagcttcg taggagggca   6840
ttttggtggt gaagaggaga ctgaaataaa tttagtctgc agaacttttt atcggaacct   6900
tatctggggc agtgaagtat atgttatggt aatagttacg agttagttga acttatagat   6960
agactggact atacggctat cggtccaaat tagaaagaac gtcaatggct ctctgggcgt   7020
cgcctttgcc gacaaaaatg tgatcatgat gaaagccagc aatgacgttg cagctgatat   7080
tgttgtcggc caaccgcgcc gaaaacgcag ctgtcagacc cacagcctcc aacgaagaat   7140
gtatcgtcaa agtgatccaa gcacactcat agttggagtc gtactccaaa ggcggcaatg   7200
acgagtcaga cagatactcg tcgacgcagt aggatgtcct gcacgggtct ttttgtgggg   7260
tgtggagaaa ggggtgcttg gagatggaag ccggtagaac cgggctgctt gtgcttggag   7320
atggaagccg gtagaaccgg gctgcttggg gggatttggg gccgctgggc tccaaagagg   7380
ggtaggcatt tcgttggggt tacgtaattg cggcatttgg gtcctgcgcg catgtcccat   7440
tggtcagaat tagtccggat aggagactta tcagccaatc acagcgccgg atccacctgt   7500
aggttgggtt gggtgggagc acccctccac agagtagagt caaacagcag cagcaacatg   7560
atagttgggg gtgtgcgtgt taaaggaaaa aaaagaagct tgggttatat tcccgctcta   7620
tttagaggtt gcgggataga cgccgacgga gggcaatggc gccatggaac cttgcggata   7680
tcgatacgcc gcggcggact gcgtccgaac cagctccagc agcgtttttt ccgggccatt   7740
gagccgactg cgaccccgcc aacgtgtctt ggcccacgca ctcatgtcat gttggtgttg   7800
ggaggccact ttttaagtag cacaaggcac ctagctcgca gcaaggtgtc cgaaccaaag   7860
aagcggctgc agtggtgcaa acggggcgga aacggcggga aaaagccacg gggggcacgaa   7920
ttgaggcacg ccctcgaatt tgagacgagt cacggcccca ttcgcccgcg caatggctcg   7980
ccaacgcccg gtcttttgca ccacatcagg ttaccccaag ccaaaccttt gtgttaaaaa   8040
gcttaacata ttataccgaa cgtaggtttg ggcgggcttg ctccgtctgt ccaaggcaac   8100
atttatataa gggtctgcat cgccggctca attgaatctt ttttcttctt ctcttctcta   8160
tattcattct tgaattaaac acacatcaat ccgc                                8194
```

<210> SEQ ID NO 31
<211> LENGTH: 10838
<212> TYPE: DNA
<213> ORGANISM: Artificial Sequence
<220> FEATURE:
<223> OTHER INFORMATION: Plasmid pKO2UF2PE
<220> FEATURE:
<221> NAME/KEY: misc_feature -continued

```
<222> LOCATION: (1615)..(1618)
<223> OTHER INFORMATION: n is a, c, g, or t
<220> FEATURE:
<221> NAME/KEY: misc_feature
<222> LOCATION: (1623)..(1623)
<223> OTHER INFORMATION: n is a, c, g, or t

<400> SEQUENCE: 31

aaattgcccc ggagaagacg gccaggccgc ctagatgaca aattcaacaa ctcacagctg     60

actttctgcc attgccacta gggggggcc tttttatatg gccaagccaa gctctccacg     120

tcggttgggc tgcacccaac aataaatggg tagggttgca ccaacaaagg gatgggatgg    180

ggggtagaag atacgaggat aacggggctc aatggcacaa ataagaacga atactgccat    240

taagactcgt gatccagcga ctgacaccat tgcatcatct aagggcctca aaactacctc    300

ggaactgctg cgctgatctg gacaccacag aggttccgag cactttaggt tgcaccaaat    360

gtcccaccag gtgcaggcag aaaacgctgg aacagcgtgt acagtttgtc ttaacaaaaa    420

gtgagggcgc tgaggtcgag cagggtggtg tgacttgtta tagcctttag agctgcgaaa    480

gcgcgtatgg atttggctca tcaggccaga ttgagggtct gtggacacat gtcatgttag    540

tgtacttcaa tcgcccccctg gatatagccc cgacaatagg ccgtggcctc atttttttgc    600

cttccgcaca tttccattgc tcgataccca caccttgctt ctcctgcact tgccaacctt    660

aatactggtt tacattgacc aacatcttac aagcgggggg cttgtctagg gtatatataa    720

acagtggctc tcccaatcgg ttgccagtct cttttttcct ttctttcccc acagattcga    780

aatctaaact acacatcaca gaattccgag ccgtgagtat ccacgacaag atcagtgtcg    840

agacgacgcg ttttgtgtaa tgacacaatc cgaaagtcgc tagcaacaca cactctctac    900

acaaactaac ccagctctgg taccatggcg tccacttcgg ctctgcccaa gcagaaccct    960

gcgcttagac gcaccgtcac ctcaactact gtgacggatt ctgagtctgc cgccgtctct   1020

ccttcagact ctccccgcca ctcggcctct tccacatcgc tctcgtccat gtccgaggtt   1080

gatatcgcca agcccaagtc cgagtatggt gtcatgctcg acacctacgg caaccagttc   1140

gaggttcccg actttaccat caaggacatc tacaatgcca tccctaagca ctgcttcaag   1200

cgctccgctc tcaagggata cggttatatc ctccgcgaca ttgtcctcct gactaccact   1260

ttcagcatct ggtacaactt tgtgaccccc gaatatatcc cctccacccc cgcccgcgct   1320

ggtctgtggg ccgtgtacac cgttcttcag ggtcttttcg gtactggtct ctgggttatt   1380

gcccatgagt gcggtcacgg tgctttctcc gattctcgca tcatcaacga cattactggc   1440

tgggttcttc actcttccct ccttgtcccc tacttcagct ggcaaatctc ccaccgaaag   1500

caccacaagg ccactggcaa catggagcgt gacatggtct tcgttccccg aacccgcgag   1560

cagcaggcta ctcgtctcgg aaagatgacc cacgagctcg ctcatcttac tgagnnnntc   1620

gtnggctggc ccaactacct catcaccaat gttaccggcc acaactacca cgagcgccag   1680

cgtgagggtc gcggcaaggg caagcataac ggcctcggcg gtggtgttaa ccacttcgat   1740

ccccgcagcc ctctgtacga gaacagtgac gctaagctca tcgtcctcag cgatattggt   1800

atcggtctga tggccactgc tctgtacttc ctcgttcaga agttcggttt ctacaacatg   1860

gccatctggt actttgttcc ctacctctgg gttaaccact ggctcgttgc catcaccttc   1920

ctccagcaca ccgaccctac ccttccccac tacaccaacg acgagtggaa cttcgtccgt   1980

ggtgccgctg ctaccattga ccgtgagatg ggcttcatcg gccgccacct tctccacggc   2040

atcatcgaga ctcatgtcct ccaccactac gtcagcagca tccccttcta caacgcggac   2100
```

-continued

```
gaggccaccg aggccattaa gcccatcatg ggcaagcact accgggctga tgtccaggat   2160
ggtcctcgtg gcttcatccg cgccatgtac cgcagtgcgc gtatgtgcca gtgggttgag   2220
cccagcgctg gtgccgaggg tgctggtaag ggtgttctgt tcttccgcaa ccgcaacaac   2280
gtgggcaccc cccccgctgt tatcaagccc gttgcttaag taggcgcggc cgcaagtgtg   2340
gatggggaag tgagtgcccg gttctgtgtg cacaattggc aatccaagat ggatggattc   2400
aacacaggga tatagcgagc tacgtggtgg tgcgaggata tagcaacgga tatttatgtt   2460
tgacacttga gaatgtacga tacaagcact gtccaagtac aatactaaac atactgtaca   2520
tactcatact cgtacccggg caacggtttc acttgagtgc agtggctagt gctcttactc   2580
gtacagtgtg caatactgcg tatcatagtc tttgatgtat atcgtattca ttcatgttag   2640
ttgcgtacgg gtgaagcttc cactggtcgg cgtggtagtg ggcagagtg gggtcggtgt    2700
gctgcaggta ggtgatggcc acgagccagt ggttgaccca caggtagggg atcaggtagt   2760
agagggtgac ggaagccagg ccccatcggt tgatggagta tgcgatgacg gacatggtga   2820
taccaatacc gacgttagag atccagatgt tgaaccagtc cttcttctca aacagcgggg   2880
cgttggggtt gaagtggttg acagcccatt tgttgagctt ggggtacttc tgtccggtaa   2940
cgtaagacag cagatacaga ggccatccaa acacctgctg ggtgatgagg ccgtagaggg   3000
tcatgagggg agcgtcctca gcaagctcag accagtcatg ggcgcctcgg ttctccataa   3060
actcctttcg gtccttgggc acaaacacca tatcacgggt gaggtgacca gtggacttgt   3120
ggtgcatgga gtgggtcagc ttccaggcgt agtaagggac cagcatggag gagtgcagaa   3180
cccatccggt gacgttgttg acggtgttag agtcggagaa agcagagtgg ccacactcgt   3240
gggcaagaac ccacagaccg gtgccaaaca gaccctggac aatggagtac atggcccagg   3300
ccacagctcg gccggaagcc gagggaataa gaggcaggta cgcgtaggcc atgtaggcaa   3360
aaacggcgat aaagaagcag gcgcgccagc tgcattaatg aatcggccaa cgcgcgggga   3420
gaggcggttt gcgtattggg cgctcttccg cttcctcgct cactgactcg ctgcgctcgg   3480
tcgttcggct gcggcgagcg gtatcagctc actcaaaggc ggtaatacgg ttatccacag   3540
aatcagggga taacgcagga aagaacatgt gagcaaaagg ccagcaaaag gccaggaacc   3600
gtaaaaaggc cgcgttgctg gcgtttttcc ataggctccg cccccctgac gagcatcaca   3660
aaaatcgacg ctcaagtcag aggtggcgaa acccgacagg actataaaga taccaggcgt   3720
ttccccctgg aagctccctc gtgcgctctc ctgttccgac cctgccgctt accggatacc   3780
tgtccgcctt tctcccttcg ggaagcgtgg cgctttctca tagctcacgc tgtaggtatc   3840
tcagttcggt gtaggtcgtt cgctccaagc tgggctgtgt gcacgaaccc cccgttcagc   3900
ccgaccgctg cgccttatcc ggtaactatc gtcttgagtc caacccggta agacacgact   3960
tatcgccact ggcagcagcc actggtaaca ggattagcag agcgaggtat gtaggcggtg   4020
ctacagagtt cttgaagtgg tggcctaact acggctacac tagaagaaca gtatttggta   4080
tctgcgctct gctgaagcca gttaccttcg gaaaaagagt tggtagctct tgatccggca   4140
aacaaaccac cgctggtagc ggtggttttt ttgtttgcaa gcagcagatt acgcgcagaa   4200
aaaaaggatc tcaagaagat cctttgatct tttctacggg gtctgacgct cagtggaacg   4260
aaaactcacg ttaagggatt ttggtcatga gattatcaaa aaggatcttc acctagatcc   4320
ttttaaatta aaaatgaagt tttaaatcaa tctaaagtat atatgagtaa acttggtctg   4380
acagttacca atgcttaatc agtgaggcac ctatctcagc gatctgtcta tttcgttcat   4440
ccatagttgc ctgactcccc gtcgtgtaga taactacgat acgggagggc ttaccatctg   4500
```

-continued

```
gccccagtgc tgcaatgata ccgcgagacc cacgctcacc ggctccagat ttatcagcaa   4560
taaaccagcc agccggaagg gccgagcgca gaagtggtcc tgcaacttta tccgcctcca   4620
tccagtctat taattgttgc cgggaagcta gagtaagtag ttcgccagtt aatagtttgc   4680
gcaacgttgt tgccattgct acaggcatcg tggtgtcacg ctcgtcgttt ggtatggctt   4740
cattcagctc cggttcccaa cgatcaaggc gagttacatg atcccccatg ttgtgcaaaa   4800
aagcggttag ctccttcggt cctccgatcg ttgtcagaag taagttggcc gcagtgttat   4860
cactcatggt tatggcagca ctgcataatt ctcttactgt catgccatcc gtaagatgct   4920
tttctgtgac tggtgagtac tcaaccaagt cattctgaga atagtgtatg cggcgaccga   4980
gttgctcttg cccggcgtca atacgggata ataccgcgcc acatagcaga actttaaaag   5040
tgctcatcat tggaaaacgt tcttcggggc gaaaactctc aaggatctta ccgctgttga   5100
gatccagttc gatgtaaccc actcgtgcac ccaactgatc ttcagcatct tttactttca   5160
ccagcgtttc tgggtgagca aaaacaggaa ggcaaaatgc cgcaaaaaag ggaataaggg   5220
cgacacggaa atgttgaata ctcatactct tcctttttca atattattga agcatttatc   5280
agggttattg tctcatgagc ggatacatat ttgaatgtat ttagaaaaat aaacaaatag   5340
gggttccgcg cacatttccc cgaaaagtgc cacctgatgc ggtgtgaaat accgcacaga   5400
tgcgtaagga gaaaataccg catcaggaaa ttgtaagcgt taatattttg ttaaaattcg   5460
cgttaaattt ttgttaaatc agctcatttt ttaaccaata ggccgaaatc ggcaaaatcc   5520
cttataaatc aaaagaatag accgagatag ggttgagtgt tgttccagtt tggaacaaga   5580
gtccactatt aaagaacgtg gactccaacg tcaaagggcg aaaaaccgtc tatcagggcg   5640
atggcccact acgtgaacca tcaccctaat caagtttttt ggggtcgagg tgccgtaaag   5700
cactaaatcg gaaccctaaa gggagccccc gatttagagc ttgacgggga aagccggcga   5760
acgtggcgag aaaggaaggg aagaaagcga aaggagcggg cgctagggcg ctggcaagtg   5820
tagcggtcac gctgcgcgta accaccacac ccgccgcgct taatgcgccg ctacagggcg   5880
cgtccattcg ccattcaggc tgcgcaactg ttgggaaggg cgatcggtgc gggcctcttc   5940
gctattacgc cagctggcga aaggggggatg tgctgcaagg cgattaagtt gggtaacgcc   6000
agggttttcc cagtcacgac gttgtaaaac gacggccagt gaattgtaat acgactcact   6060
atagggcgaa ttgggcccga cgtcgcatgc ttgaatctac aagtaggagg gttggagtga   6120
ttaagtgaaa cttctttaac ggctctatgc cagttctatt gatatccgaa acatcagtat   6180
gaaggtctga taagggtgac ttcttcccac agattcgtat cagtacgagt acgagaccgg   6240
tacttgtaac agtattgata ctaaagggaa actacaacgg ttgtcagcgt aatgtgactt   6300
cgcccatgaa cgcagacacg cagtgccgag tgcggtgata tcgcctactc gttacgtcca   6360
tggactacac aacccctcgg cttcgcttgg cttagcctcg ggctcggtgc tgttcagtta   6420
aaacacaatc aaataacatt tctacttttt agaaggcagg ccgtcaggag caactccgac   6480
tccattgacg tttctaaaca tctgaatgcc ttccttacct tcaacaaact ggcaggttcg   6540
ggcgacagtg taaagagact tgatgaagtt ggtgtcgtcg tgtcggtagt gcttgcccat   6600
gaccttcttg atcttctcag tggcgattcg ggcgttgtag aagggaattc cgtcgtcgcc   6660
tgagtcgacg agtatctgtc tgactcgtca ttgccgcctt tggagtacga ctccaactat   6720
gagtgtgctt ggatcacttt gacgatacat tcttcgttgg aggctgtggg tctgacagct   6780
gcgttttcgg cgcggttggc cgacaacaat atcagctgca acgtcattgc tggctttcat   6840
```

-continued

```
catgatcaca tttttgtcgg caaaggcgac gcccagagag ccattgacgt tctttctaat   6900
ttggaccgat agccgtatag tccagtctat ctataagttc aactaactcg taactattac   6960
cataacatat acttcactgc cccagataag gttccgataa aaagttctgc agactaaatt   7020
tatttcagtc tcctcttcac caccaaaatg ccctcctacg aagctcgagc taacgtccac   7080
aagtccgcct ttgccgctcg agtgctcaag ctcgtggcag ccaagaaaac caacctgtgt   7140
gcttctctgg atgttaccac caccaaggag ctcattgagc ttgccgataa ggtcggacct   7200
tatgtgtgca tgatcaaaac ccatatcgac atcattgacg acttcaccta cgccggcact   7260
gtgctccccc tcaaggaact tgctcttaag cacggtttct tcctgttcga ggacagaaag   7320
ttcgcagata ttggcaacac tgtcaagcac cagtaccggt gtcaccgaat cgccgagtgg   7380
tccgatatca ccaacgccca cggtgtaccc ggaaccggaa tcattgctgg cctgcgagct   7440
ggtgccgagg aaactgtctc tgaacagaag aaggaggacg tctctgacta cgagaactcc   7500
cagtacaagg agttcctagt cccctctccc aacgagaagc tggccagagg tctgctcatg   7560
ctggccgagc tgtcttgcaa gggctctctg gccactggcg agtactccaa gcagaccatt   7620
gagcttgccc gatccgaccc cgagtttgtg gttggcttca ttgcccagaa ccgacctaag   7680
ggcgactctg aggactggct tattctgacc cccggggtgg gtcttgacga caagggagac   7740
gctctcggac agcagtaccg aactgttgag gatgtcatgt ctaccggaac ggatatcata   7800
attgtcggcc gaggtctgta cggccagaac cgagatccta ttgaggaggc caagcgatac   7860
cagaaggctg gctgggaggc ttaccagaag attaactgtt agaggttaga ctatggatat   7920
gtaatttaac tgtgtatata gagagcgtgc aagtatggag cgcttgttca gcttgtatga   7980
tggtcagacg acctgtctga tcgagtatgt atgatactgc acaacctgtg tatccgcatg   8040
atctgtccaa tggggcatgt tgttgtgttt ctcgatacgg agatgctggg tacagtgcta   8100
atacgttgaa ctacttatac ttatatgagg ctcgaagaaa gctgacttgt gtatgactta   8160
attaatttga atcgaatcga tgagcctaaa atgaacccga gtatatctca taaaattctc   8220
ggtgagaggt ctgtgactgt cagtacaagg tgccttcatt atgccctcaa ccttaccata   8280
cctcactgaa tgtagtgtac ctctaaaaat gaaatacagt gccaaaagcc aaggcactga   8340
gctcgtctaa cggacttgat atacaaccaa ttaaaacaaa tgaaaagaaa tacagttctt   8400
tgtatcattt gtaacaatta ccctgtacaa actaaggtat tgaaatccca caatattccc   8460
aaagtccacc cctttccaaa ttgtcatgcc tacaactcat ataccaagca ctaacctacc   8520
gtttaaacag tgtacgcaga tcccgtcaac agttttatat atcgtagtta caaccatcaa   8580
cactttttgg taagtgtacc attctatact ccaactggtc tgcaactgta caagtagaca   8640
tgttaatggt agttaataac atctacagca gaacctatgg taaagacatt gcatttttac   8700
aggaagtatc gtcctacacg ttgataaatc caaagatgcg gaacttcttc cacttttatc   8760
atcatcccct actcgtacac tcgtactctt tgttcgatcg cgattcattt ctataaataa   8820
tcttgtatgt acatgcggcc gcttactgga gctttctggc cttctccttg gcagcgtcag   8880
ccttggcctg cttggcgagc ttggcgttct ttcggtaaaa gttgtagaag agaccgagca   8940
tggtccacat gtagaaccag agcagagcgg tgatgaagaa ggggtatcca ggtcggccaa   9000
ggaccttcat ggcgtacatg tcccaggaag actggacaga catcatgcag aactgggtca   9060
tctgggatcg agtgatgtag aacttgatga acgacacctg cttgaagccc agggcagaca   9120
gaaagtagta gccgtacatg atgacgtgga tgaaggagtt cagggcagca gagaagtagg   9180
cttcaccgtt gggagcaacg aaggtgacca gccaccagat ggtgaagatg gaagagtggt   9240
```

```
ggtacacgtg cagaaaggaa atctgtcggt tgttcttctt gaggaccatg atcatggtgt   9300

cgacaaactc catgatcttg gagaagtaga agagccagat catcttagcc atagggagac   9360

ccttgaaggt gtgatcggca gcgttctcaa acagtccata gttggcctga taagcctcgt   9420

acaggatgcc accgcacatg taggcggaga tggagaccag acagaagttg tgcaggaggg   9480

agaaggtctt gacctcgaat cgttcaaagt tcttcatgat ctgcataccc acaaacacgg   9540

tgaccaggta ggcgagcacg atcaggagca cgtggaaggg gttcatcaga ggcagctctc   9600

gagccagggg agactccacg gcaaccagga agcctcgagt gtgatggaca atggtgggaa   9660

tgtacttctc ggcctgggca accagggcag cctccagggg atcgacgtag ggagcagctc   9720

ggacaccgat agcgctggcg aggtccatga acaggtcctg aggcatcttg gagggcagga   9780

agggagcaat ggactccatg gttagcgtgt cgtgtttttg ttgtgctgga agaaccaaag   9840

ggtggcgcaa tgtgtgtaga tatatatgtc gtgacccaca agtcacacaa acaagtatcg   9900

ggaggagtgg tgcacctcta tgcggagaaa ccttataccg ctgtagacca actggggcag   9960

aggtgtgagt tgaagtcagc tggaggagat gtgtgacaga agcacaagaa gtgagattgt  10020

gagatgtatg tctagggggg gaagttttgt gtcaaatata tgggaattat tatcagcacc  10080

acgaaattat acgcctcata tgacccattt aggtggatag atcatggaca ctgttgacag  10140

ctgcgaagaa aaagcgtatt ggggatgatc cgaaattagt ccggtaccga ggcgcaaata  10200

cgtaagacag ccgatwaaat atatgcgaga aacaccaaag agactctaga tgtttgtttg  10260

gcacagtttt gacttctgcg aaggccttac accaccttgt tgacccttgt cgcgggtcgg  10320

gcaatatcgg ctgacagagt tttacttgct caataagata cgagctgcat agagttgaac  10380

tacaggacaa tattggggct ggccacatga agggcattgt ttggaggtgt attgatggtg  10440

aaaacacgat atgaaatgac aacgccccct gttttattat tattcttatt attttgggtg  10500

cttctctatc catacaagca cctcctaaca tgcttcataa gtgacctcct catcacaagg  10560

cctgaggtct catttatcca gtggcgccaa gctaaactaa aactggtccg agtagactaa  10620

ggcgaagaga gaaggagaga agacagtttt tttgtggccg cctgtgaaca atgaaaacga  10680

tgagggtgag atggagcaaa ccatatggac agtcagagga gtacacgctg cttacataat  10740

ggcgcaacga ccacatgtcc cacagatacg cattatgcct gtacatattc cgggggaggt  10800

atgtaccagt agttcgcctg ctaccgttag ctacattt                          10838
```

```
<210> SEQ ID NO 32
<211> LENGTH: 1936
<212> TYPE: DNA
<213> ORGANISM: Yarrowia lipolytica
<220> FEATURE:
<221> NAME/KEY: CDS
<222> LOCATION: (283)..(1539)
<223> OTHER INFORMATION: delta-12 desaturase

<400> SEQUENCE: 32

cgtagttata tacaagaggt agatgcgtgc tggtgttaga ggggctctca ggattaggag     60

gaaaatttga cattggccct caacatataa cctcgggtgt gcctctgttt accctcagct    120

tttgcttgtc cccaagtcag tcacgccagg ccaaaaaggt tggtggattg acagggagaa    180

aaaaaaaagc ctagtgggtt taaactcgag gtaagacatt gaaatatata ccggtcggca    240

tcctgagtcc ctttctcgta ttccaacaga ccgaccatag aa atg gat tcg acc       294
                                               Met Asp Ser Thr
                                               1
```

-continued

```
acg cag acc aac acc ggc acc ggc aag gtg gcc gtg cag ccc ccc acg      342
Thr Gln Thr Asn Thr Gly Thr Gly Lys Val Ala Val Gln Pro Pro Thr
5                   10                  15                  20

gcc ttc att aag ccc att gag aag gtg tcc gag ccc gtc tac gac acc      390
Ala Phe Ile Lys Pro Ile Glu Lys Val Ser Glu Pro Val Tyr Asp Thr
                25                  30                  35

ttt ggc aac gag ttc act cct cca gac tac tct atc aag gat att ctg      438
Phe Gly Asn Glu Phe Thr Pro Pro Asp Tyr Ser Ile Lys Asp Ile Leu
            40                  45                  50

gat gcc att ccc cag gag tgc tac aag cgg tcc tac gtt aag tcc tac      486
Asp Ala Ile Pro Gln Glu Cys Tyr Lys Arg Ser Tyr Val Lys Ser Tyr
        55                  60                  65

tcg tac gtg gcc cga gac tgc ttc ttt atc gcc gtt ttt gcc tac atg      534
Ser Tyr Val Ala Arg Asp Cys Phe Phe Ile Ala Val Phe Ala Tyr Met
    70                  75                  80

gcc tac gcg tac ctg cct ctt att ccc tcg gct tcc ggc cga gct gtg      582
Ala Tyr Ala Tyr Leu Pro Leu Ile Pro Ser Ala Ser Gly Arg Ala Val
85                  90                  95                  100

gcc tgg gcc atg tac tcc att gtc cag ggt ctg ttt ggc acc ggt ctg      630
Ala Trp Ala Met Tyr Ser Ile Val Gln Gly Leu Phe Gly Thr Gly Leu
                105                 110                 115

tgg gtt ctt gcc cac gag tgt ggc cac tct gct ttc tcc gac tct aac      678
Trp Val Leu Ala His Glu Cys Gly His Ser Ala Phe Ser Asp Ser Asn
            120                 125                 130

acc gtc aac aac gtc acc gga tgg gtt ctg cac tcc tcc atg ctg gtc      726
Thr Val Asn Asn Val Thr Gly Trp Val Leu His Ser Ser Met Leu Val
        135                 140                 145

cct tac tac gcc tgg aag ctg acc cac tcc atg cac cac aag tcc act      774
Pro Tyr Tyr Ala Trp Lys Leu Thr His Ser Met His His Lys Ser Thr
    150                 155                 160

ggt cac ctc acc cgt gat atg gtg ttt gtg ccc aag gac cga aag gag      822
Gly His Leu Thr Arg Asp Met Val Phe Val Pro Lys Asp Arg Lys Glu
165                 170                 175                 180

ttt atg gag aac cga ggc gcc cat gac tgg tct gag ctt gct gag gac      870
Phe Met Glu Asn Arg Gly Ala His Asp Trp Ser Glu Leu Ala Glu Asp
                185                 190                 195

gct ccc ctc atg acc ctc tac ggc ctc atc acc cag cag gtg ttt gga      918
Ala Pro Leu Met Thr Leu Tyr Gly Leu Ile Thr Gln Gln Val Phe Gly
            200                 205                 210

tgg cct ctg tat ctg ctg tct tac gtt acc gga cag aag tac ccc aag      966
Trp Pro Leu Tyr Leu Leu Ser Tyr Val Thr Gly Gln Lys Tyr Pro Lys
        215                 220                 225

ctc aac aaa tgg gct gtc aac cac ttc aac ccc aac gcc ccg ctg ttt     1014
Leu Asn Lys Trp Ala Val Asn His Phe Asn Pro Asn Ala Pro Leu Phe
    230                 235                 240

gag aag aag gac tgg ttc aac atc tgg atc tct aac gtc ggt att ggt     1062
Glu Lys Lys Asp Trp Phe Asn Ile Trp Ile Ser Asn Val Gly Ile Gly
245                 250                 255                 260

atc acc atg tcc gtc atc gca tac tcc atc aac cga tgg ggc ctg gct     1110
Ile Thr Met Ser Val Ile Ala Tyr Ser Ile Asn Arg Trp Gly Leu Ala
                265                 270                 275

tcc gtc acc ctc tac tac ctg atc ccc tac ctg tgg gtc aac cac tgg     1158
Ser Val Thr Leu Tyr Tyr Leu Ile Pro Tyr Leu Trp Val Asn His Trp
            280                 285                 290

ctc gtg gcc atc acc tac ctg cag cac acc gac ccc act ctg ccc cac     1206
Leu Val Ala Ile Thr Tyr Leu Gln His Thr Asp Pro Thr Leu Pro His
        295                 300                 305

tac cac gcc gac cag tgg aac ttc acc cga gga gcc gcc gcc acc atc     1254
Tyr His Ala Asp Gln Trp Asn Phe Thr Arg Gly Ala Ala Ala Thr Ile
    310                 315                 320
```

-continued

```
gac cga gag ttt ggc ttc atc ggc tcc ttc tgc ttc cat gac atc atc     1302
Asp Arg Glu Phe Gly Phe Ile Gly Ser Phe Cys Phe His Asp Ile Ile
325                 330                 335                 340

gag acc cac gtt ctg cac cac tac gtg tct cga att ccc ttc tac aac     1350
Glu Thr His Val Leu His His Tyr Val Ser Arg Ile Pro Phe Tyr Asn
                345                 350                 355

gcc cga atc gcc act gag aag atc aag aag gtc atg ggc aag cac tac     1398
Ala Arg Ile Ala Thr Glu Lys Ile Lys Lys Val Met Gly Lys His Tyr
            360                 365                 370

cga cac gac gac acc aac ttc atc aag tct ctt tac act gtc gcc cga     1446
Arg His Asp Asp Thr Asn Phe Ile Lys Ser Leu Tyr Thr Val Ala Arg
        375                 380                 385

acc tgc cag ttt gtt gaa ggt aag gaa ggc att cag atg ttt aga aac     1494
Thr Cys Gln Phe Val Glu Gly Lys Glu Gly Ile Gln Met Phe Arg Asn
    390                 395                 400

gtc aat gga gtc gga gtt gct cct gac ggc ctg cct tct aaa aag         1539
Val Asn Gly Val Gly Val Ala Pro Asp Gly Leu Pro Ser Lys Lys
405                 410                 415

tagagctaga aatgttattt gattgtgttt taactgaaca gcaccgagcc cgaggctaag   1599

ccaagcgaag ccgaggggtt gtgtagtcca tggacgtaac gagtaggcga tatcaccgca   1659

ctcggcactg cgtgtctgcg ttcatgggcg aagtcacatt acgctgacaa ccgttgtagt   1719

ttccctttag tatcaatact gttacaagta ccggtctcgt actcgtactg atacgaatct   1779

gtgggaagaa gtcaccctta tcagaccttc atactgatgt ttcggatatc aatagaactg   1839

gcatagagcc gttaaagaag tttcacttaa tcactccaac cctcctactt gtagattcaa   1899

gcagatcgat aagatggatt tgatggtcag tgctagc                             1936


<210> SEQ ID NO 33
<211> LENGTH: 419
<212> TYPE: PRT
<213> ORGANISM: Yarrowia lipolytica

<400> SEQUENCE: 33

Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
    50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
            100                 105                 110

Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
    130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175
```

```
Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys
```

<210> SEQ ID NO 34
<211> LENGTH: 1130
<212> TYPE: DNA
<213> ORGANISM: Yarrowia lipolytica
<220> FEATURE:
<221> NAME/KEY: misc_feature
<223> OTHER INFORMATION: GPAT promoter

<400> SEQUENCE: 34

```
caacttttct tgtcgacctg agataccgag gttgcgcagg ggatcaactt ttgtgtctca      60

gagggaccca agtgcgtacg gagagtacag tacatactgt agctaacggt agcaggcgaa     120

ctactggtac atacctcccc cggaatatgt acaggcataa tgcgtatctg tgggacatgt     180

ggtcgttgcg ccattatgta agcagcgtgt actcctctga ctgtccatat ggtttgctcc     240

atctcaccct catcgttttc attgttcaca ggcggccaca aaaaaactgt cttctctcct     300

tctctcttcg ccttagtcta ctcggaccag ttttagttta gcttggcgcc actggataaa     360

tgagacctca ggccttgtga tgaggaggtc acttatgaag catgttagga ggtgcttgta     420

tggatagaga agcacccaaa ataataagaa taataataaa acagggggcg ttgtcatttc     480

atatcgtgtt ttcaccatca atacacctcc aaacaatgcc cttcatgtgg ccagccccaa     540

tattgtcctg tagttcaact ctatgcagct cgtatcttat tgagcaagta aaactctgtc     600
```

-continued

```
agccgatatt gcccgacccg cgacaagggt caacaaggtg gtgtaaggcc ttcgcagaag    660

tcaaaactgt gccaaacaaa catctagagt ctctttggtg tttctcgcat atatttaatc    720

ggctgtctta cgtatttggc ctcggtaccg gactaatttc ggatcatccc caatacgctt    780

tttcttcgca gctgtcaaca gtgtccatga tctatccacc taaatgggtc atatgaggcg    840

tataatttcg tggtgctgat aataattccc atatatttga cacaaaactt cccccccctag    900

acatacatct cacaatctca cttcttgtgc ttctgtcaca catctcctcc agctgacttc    960

aactcacacc tctgccccag ttggtctaca gcggtataag gtttctccgc atagaggtgc   1020

accactcctc ccgatacttg tttgtgtgac ttgtgggtca cgacatatat atctacacac   1080

attgcgccac cctttggttc ttccagcaca acaaaaacac gacacgctaa              1130
```

<210> SEQ ID NO 35
<211> LENGTH: 5833
<212> TYPE: DNA
<213> ORGANISM: Artificial Sequence
<220> FEATURE:
<223> OTHER INFORMATION: Plasmid pZKUT16

<400> SEQUENCE: 35

```
gtacgaggaa actgtctctg aacagaagaa ggaggacgtc tctgactacg agaactccca     60

gtacaaggag ttcctagtcc cctctcccaa cgagaagctg gccagaggtc tgctcatgct    120

ggccgagctg tcttgcaagg gctctctggc cactggcgag tactccaagc agaccattga    180

gcttgcccga tccgaccccg agtttgtggt tggcttcatt gcccagaacc gacctaaggg    240

cgactctgag gactggctta ttctgacccc cggggtgggt cttgacgaca agggagacgc    300

tctcggacag cagtaccgaa ctgttgagga tgtcatgtct accggaacgg atatcataat    360

tgtcggccga ggtctgtacg gccagaaccg agatcctatt gaggaggcca agcgatacca    420

gaaggctggc tgggaggctt accagaagat taactgttag aggttagact atggatatgt    480

aatttaactg tgtatataga gagcgtgcaa gtatggagcg cttgttcagc ttgtatgatg    540

gtcagacgac ctgtctgatc gagtatgtat gatactgcac aacctgtgta tccgcatgat    600

ctgtccaatg gggcatgttg ttgtgtttct cgatacggag atgctgggta cagtgctaat    660

acgttgaact acttatactt atatgaggct cgaagaaagc tgacttgtgt atgacttaat    720

taatcgagct tggcgtaatc atggtcatag ctgtttcctg tgtgaaattg ttatccgctc    780

acaattccac acaacatacg agccggaagc ataaagtgta aagcctgggg tgcctaatga    840

gtgagctaac tcacattaat tgcgttgcgc tcactgcccg ctttccagtc gggaaacctg    900

tcgtgccagc tgcattaatg aatcggccaa cgcgcgggga gaggcggttt gcgtattggg    960

cgctcttccg cttcctcgct cactgactcg ctgcgctcgg tcgttcggct gcggcgagcg   1020

gtatcagctc actcaaaggc ggtaatacgg ttatccacag aatcagggga taacgcagga   1080

aagaacatgt gagcaaaagg ccagcaaaag gccaggaacc gtaaaaaggc cgcgttgctg   1140

gcgtttttcc ataggctccg cccccctgac gagcatcaca aaaatcgacg ctcaagtcag   1200

aggtggcgaa acccgacagg actataaaga taccaggcgt ttccccctgg aagctccctc   1260

gtgcgctctc ctgttccgac cctgccgctt accggatacc tgtccgcctt tctcccttcg   1320

ggaagcgtgg cgctttctca tagctcacgc tgtaggtatc tcagttcggt gtaggtcgtt   1380

cgctccaagc tgggctgtgt gcacgaaccc cccgttcagc ccgaccgctg cgccttatcc   1440

ggtaactatc gtcttgagtc caacccggta agacacgact tatcgccact ggcagcagcc   1500

actggtaaca ggattagcag agcgaggtat gtaggcggtg ctacagagtt cttgaagtgg   1560
```

-continued

```
tggcctaact acggctacac tagaaggaca gtatttggta tctgcgctct gctgaagcca   1620
gttaccttcg gaaaaagagt tggtagctct tgatccggca aacaaaccac cgctggtagc   1680
ggtggttttt ttgtttgcaa gcagcagatt acgcgcagaa aaaaaggatc tcaagaagat   1740
cctttgatct tttctacggg gtctgacgct cagtggaacg aaaactcacg ttaagggatt   1800
ttggtcatga gattatcaaa aaggatcttc acctagatcc ttttaaatta aaaatgaagt   1860
tttaaatcaa tctaaagtat atatgagtaa acttggtctg acagttacca atgcttaatc   1920
agtgaggcac ctatctcagc gatctgtcta tttcgttcat ccatagttgc ctgactcccc   1980
gtcgtgtaga taactacgat acgggagggc ttaccatctg gccccagtgc tgcaatgata   2040
ccgcgagacc cacgctcacc ggctccagat ttatcagcaa taaaccagcc agccggaagg   2100
gccgagcgca gaagtggtcc tgcaacttta tccgcctcca tccagtctat taattgttgc   2160
cgggaagcta gagtaagtag ttcgccagtt aatagtttgc gcaacgttgt tgccattgct   2220
acaggcatcg tggtgtcacg ctcgtcgttt ggtatggctt cattcagctc cggttcccaa   2280
cgatcaaggc gagttacatg atcccccatg ttgtgcaaaa aagcggttag ctccttcggt   2340
cctccgatcg ttgtcagaag taagttggcc gcagtgttat cactcatggt tatggcagca   2400
ctgcataatt ctcttactgt catgccatcc gtaagatgct tttctgtgac tggtgagtac   2460
tcaaccaagt cattctgaga atagtgtatg cggcgaccga gttgctcttg cccggcgtca   2520
atacgggata ataccgcgcc acatagcaga actttaaaag tgctcatcat tggaaaacgt   2580
tcttcggggc gaaaactctc aaggatctta ccgctgttga gatccagttc gatgtaaccc   2640
actcgtgcac ccaactgatc ttcagcatct tttactttca ccagcgtttc tgggtgagca   2700
aaaacaggaa ggcaaaatgc cgcaaaaaag ggaataaggg cgacacggaa atgttgaata   2760
ctcatactct tcctttttca atattattga agcatttatc agggttattg tctcatgagc   2820
ggatacatat ttgaatgtat ttagaaaaat aaacaaatag gggttccgcg cacatttccc   2880
cgaaaagtgc cacctgacgc gccctgtagc ggcgcattaa gcgcggcggg tgtggtggtt   2940
acgcgcagcg tgaccgctac acttgccagc gccctagcgc ccgctccttt cgctttcttc   3000
ccttcctttc tcgccacgtt cgccggcttt ccccgtcaag ctctaaatcg ggggctccct   3060
ttagggttcc gatttagtgc tttacggcac ctcgacccca aaaaacttga ttagggtgat   3120
ggttcacgta gtgggccatc gccctgatag acggtttttc gccctttgac gttggagtcc   3180
acgttcttta atagtggact cttgttccaa actggaacaa cactcaaccc tatctcggtc   3240
tattcttttg atttataagg gattttgccg atttcggcct attggttaaa aaatgagctg   3300
atttaacaaa aatttaacgc gaattttaac aaaatattaa cgcttacaat ttccattcgc   3360
cattcaggct gcgcaactgt tgggaagggc gatcggtgcg ggcctcttcg ctattacgcc   3420
agctggcgaa agggggatgt gctgcaaggc gattaagttg ggtaacgcca gggttttccc   3480
agtcacgacg ttgtaaaacg acggccagtg aattgtaata cgactcacta tagggcgaat   3540
tgggtaccgg gccccccctc gaggtcgacg agtatctgtc tgactcgtca ttgccgcctt   3600
tggagtacga ctccaactat gagtgtgctt ggatcacttt gacgatacat tcttcgttgg   3660
aggctgtggg tctgacagct gcgttttcgg cgcggttggc cgacaacaat atcagctgca   3720
acgtcattgc tggctttcat catgatcaca tttttgtcgg caaaggcgac gcccagagag   3780
ccattgacgt tctttctaat ttggaccgat agccgtatag tccagtctat ctataagttc   3840
aactaactcg taactattac cataacatat acttcactgc cccagataag gttccgataa   3900
```

-continued

```
aaagttctgc agactaaatt tatttcagtc tcctcttcac caccaaaatg ccctcctacg   3960
aagctcgagt gctcaagctc gtggcagcca agaaaaccaa cctgtgtgct tctctggatg   4020
ttaccaccac caaggagctc attgagcttg ccgataaggt cggaccttat gtgtgcatga   4080
tcaaaaccca tatcgacatc attgacgact tcacctacgc cggcactgtg ctcccccctca   4140
aggaacttgc tcttaagcac ggtttcttcc tgttcgagga cagaaagttc gcagatattg   4200
gcaacactgt caagcaccag taccggtgtc accgaatcgc cgagtggtcc gatatcacca   4260
acgcccacgg tgtacccgga accggaatcg atgcagaatt caggagagac cgggttggcg   4320
gcgtatttgt gtcccaaaaa acagccccaa ttgccccaat tgaccccaaa ttgacccagt   4380
agcgggccca accccggcga gagccccctt caccccacat atcaaacctc ccccggttcc   4440
cacacttgcc gttaagggcg tagggtactg cagtctggaa tctacgcttg ttcagacttt   4500
gtactagttt ctttgtctgg ccatccgggt aacccatgcc ggacgcaaaa tagactactg   4560
aaaatttttt tgctttgtgg ttgggacttt agccaagggt ataaaagacc accgtccccg   4620
aattaccttt cctcttcttt tctctctctc cttgtcaact cacacccgaa atcgttaagc   4680
atttccttct gagtataaga atcattcacc atggacatgt ccgtcctgac tctccaagag   4740
tacgagttcg agaagcagtt caacgagaat gaagccatcc aatggatgca ggaaaactgg   4800
aagaaatcct tcctgttttc tgccctctac gctgccttta tctttggtgg acgacatctg   4860
atgaacaagc gagccaagtt tgagctgcga aaacctctcg tgctctggtc cctgaccctc   4920
gctgtcttct ctatcttcgg tgctctgcga actggagcct acatgctcta catcctgatg   4980
accaaaggcc tgaaacagtc tgtttgtgac cagtcctttt acaacggacc cgtctcgaaa   5040
ttctgggctt acgcctttgt gctctccaaa gctcccgaac ttggcgatac catcttcatc   5100
attctgcgaa agcagaaact catcttcctg cactggtatc accacatcac cgtcctcctg   5160
tactcttggt actcctacaa ggacatggtg gctggaggtg gctggttcat gactatgaac   5220
tacggtgtcc acgccgtgat gtactcctac tacgccctcc gagctgccgg tttccgagtc   5280
tctcgaaagt ttgccatgtt catcaccctg tcgcagatca ctcagatgct catgggctgt   5340
gtcattaact acctggtctt caactggatg cagcatgaca atgaccagtg ctactcccac   5400
tttcagaaca tcttctggtc ctctctcatg tacctctcct accttctgct cttctgccat   5460
ttcttctttg aggcctacat tggcaaagtg aagaaagcca ccaaggctga gtaagcggcc   5520
gcaagtgtgg atggggaagt gagtgcccgg ttctgtgtgc acaattggca atccaagatg   5580
gatggattca acacagggat atagcgagct acgtggtggt gcgaggatat agcaacggat   5640
atttatgttt gacacttgag aatgtacgat acaagcactg tccaagtaca atactaaaca   5700
tactgtacat actcatactc gtacccgggc aacggtttca cttgagtgca gtggctagtg   5760
ctcttactcg tacagtgtgc aatactgcgt atcatagtct ttgatgtata tcgtattcat   5820
tcatgttagt tgc                                                       5833
```

<210> SEQ ID NO 36
<211> LENGTH: 804
<212> TYPE: DNA
<213> ORGANISM: Rattus norvegicus
<220> FEATURE:
<221> NAME/KEY: misc_feature
<223> OTHER INFORMATION: synthetic C16 elongase (codon-optimized)

<400> SEQUENCE: 36

```
atggacatgt ccgtcctgac tctccaagag tacgagttcg agaagcagtt caacgagaat     60
```

-continued

```
gaagccatcc aatggatgca ggaaaactgg aagaaatcct tcctgttttc tgccctctac    120

gctgccttta tctttggtgg acgacatctg atgaacaagc gagccaagtt tgagctgcga    180

aaacctctcg tgctctggtc cctgaccctc gctgtcttct ctatcttcgg tgctctgcga    240

actggagcct acatgctcta catcctgatg accaaaggcc tgaaacagtc tgtttgtgac    300

cagtcctttt acaacggacc cgtctcgaaa ttctgggctt acgcctttgt gctctccaaa    360

gctcccgaac ttggcgatac catcttcatc attctgcgaa agcagaaact catcttcctg    420

cactggtatc accacatcac cgtcctcctg tactcttggt actcctacaa ggacatggtg    480

gctggaggtg gctggttcat gactatgaac tacggtgtcc acgccgtgat gtactcctac    540

tacgccctcc gagctgccgg tttccgagtc tctcgaaagt ttgccatgtt catcaccctg    600

tcgcagatca ctcagatgct catgggctgt gtcattaact acctggtctt caactggatg    660

cagcatgaca atgaccagtg ctactcccac tttcagaaca tcttctggtc ctctctcatg    720

tacctctcct accttctgct cttctgccat ttcttctttg aggcctacat tggcaaagtg    780

aagaaagcca ccaaggctga gtaa                                           804
```

```
<210> SEQ ID NO 37
<211> LENGTH: 267
<212> TYPE: PRT
<213> ORGANISM: Rattus norvegicus (GenBank Accession No. AB071986)

<400> SEQUENCE: 37

Met Asn Met Ser Val Leu Thr Leu Gln Glu Tyr Glu Phe Glu Lys Gln
1               5                   10                  15

Phe Asn Glu Asn Glu Ala Ile Gln Trp Met Gln Glu Asn Trp Lys Lys
            20                  25                  30

Ser Phe Leu Phe Ser Ala Leu Tyr Ala Ala Phe Ile Phe Gly Gly Arg
        35                  40                  45

His Leu Met Asn Lys Arg Ala Lys Phe Glu Leu Arg Lys Pro Leu Val
    50                  55                  60

Leu Trp Ser Leu Thr Leu Ala Val Phe Ser Ile Phe Gly Ala Leu Arg
65                  70                  75                  80

Thr Gly Ala Tyr Met Leu Tyr Ile Leu Met Thr Lys Gly Leu Lys Gln
                85                  90                  95

Ser Val Cys Asp Gln Ser Phe Tyr Asn Gly Pro Val Ser Lys Phe Trp
            100                 105                 110

Ala Tyr Ala Phe Val Leu Ser Lys Ala Pro Glu Leu Gly Asp Thr Ile
        115                 120                 125

Phe Ile Ile Leu Arg Lys Gln Lys Leu Ile Phe Leu His Trp Tyr His
    130                 135                 140

His Ile Thr Val Leu Leu Tyr Ser Trp Tyr Ser Tyr Lys Asp Met Val
145                 150                 155                 160

Ala Gly Gly Gly Trp Phe Met Thr Met Asn Tyr Gly Val His Ala Val
                165                 170                 175

Met Tyr Ser Tyr Tyr Ala Leu Arg Ala Ala Gly Phe Arg Val Ser Arg
            180                 185                 190

Lys Phe Ala Met Phe Ile Thr Leu Ser Gln Ile Thr Gln Met Leu Met
        195                 200                 205

Gly Cys Val Ile Asn Tyr Leu Val Phe Asn Trp Met Gln His Asp Asn
    210                 215                 220

Asp Gln Cys Tyr Ser His Phe Gln Asn Ile Phe Trp Ser Ser Leu Met
225                 230                 235                 240
```

-continued

```
Tyr Leu Ser Tyr Leu Leu Leu Phe Cys His Phe Phe Phe Glu Ala Tyr
                245                 250                 255

Ile Gly Lys Val Lys Lys Ala Thr Lys Ala Glu
            260                 265
```

<210> SEQ ID NO 38
<211> LENGTH: 33
<212> TYPE: DNA
<213> ORGANISM: Artificial Sequence
<220> FEATURE:
<223> OTHER INFORMATION: Primer MLPAT-F

<400> SEQUENCE: 38

```
gatcccatgg tcgggtccgt cacccgaccc aca                                 33
```

<210> SEQ ID NO 39
<211> LENGTH: 34
<212> TYPE: DNA
<213> ORGANISM: Artificial Sequence
<220> FEATURE:
<223> OTHER INFORMATION: Primer MLPAT-R

<400> SEQUENCE: 39

```
gatcgcggcc gctcacatcc agttctctga ccac                                34
```

<210> SEQ ID NO 40
<211> LENGTH: 8165
<212> TYPE: DNA
<213> ORGANISM: Artificial Sequence
<220> FEATURE:
<223> OTHER INFORMATION: Plasmid pZUF17

<400> SEQUENCE: 40

```
gtacgagccg gaagcataaa gtgtaaagcc tggggtgcct aatgagtgag ctaactcaca     60

ttaattgcgt tgcgctcact gcccgctttc cagtcgggaa acctgtcgtg ccagctgcat    120

taatgaatcg gccaacgcgc ggggagaggc ggtttgcgta ttgggcgctc ttccgcttcc    180

tcgctcactg actcgctgcg ctcggtcgtt cggctgcggc gagcggtatc agctcactca    240

aaggcggtaa tacggttatc cacagaatca ggggataacg caggaaagaa catgtgagca    300

aaaggccagc aaaaggccag gaaccgtaaa aaggccgcgt tgctggcgtt tttccatagg    360

ctccgccccc ctgacgagca tcacaaaaat cgacgctcaa gtcagaggtg gcgaaacccg    420

acaggactat aaagatacca ggcgtttccc cctggaagct ccctcgtgcg ctctcctgtt    480

ccgaccctgc cgcttaccgg atacctgtcc gcctttctcc cttcgggaag cgtggcgctt    540

tctcatagct cacgctgtag gtatctcagt tcggtgtagg tcgttcgctc caagctgggc    600

tgtgtgcacg aaccccccgt tcagcccgac cgctgcgcct tatccggtaa ctatcgtctt    660

gagtccaacc cggtaagaca cgacttatcg ccactggcag cagccactgg taacaggatt    720

agcagagcga ggtatgtagg cggtgctaca gagttcttga agtggtggcc taactacggc    780

tacactagaa ggacagtatt tggtatctgc gctctgctga agccagttac cttcggaaaa    840

agagttggta gctcttgatc cggcaaacaa accaccgctg gtagcggtgg tttttttgtt    900

tgcaagcagc agattacgcg cagaaaaaaa ggatctcaag aagatccttt gatcttttct    960

acggggtctg acgctcagtg gaacgaaaac tcacgttaag ggattttggt catgagatta   1020

tcaaaaagga tcttcaccta gatcctttta aattaaaaat gaagttttaa atcaatctaa   1080

agtatatatg agtaaacttg gtctgacagt taccaatgct taatcagtga ggcacctatc   1140

tcagcgatct gtctatttcg ttcatccata gttgcctgac tccccgtcgt gtagataact   1200
```

-continued

```
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
```

-continued

```
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttgc ttaaattcaa tccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg gggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg ggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggcctttt tatatggcca agccaagctc tccacgtcgg ttgggctgca cccaacaata   5940
```

-continued

```
aatgggtagg gttgcaccaa caaagggatg ggatgggggg tagaagatac gaggataacg   6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
cgctggaaca gcgtgtacag tttgtcttaa caaaaagtga gggcgctgag gtcgagcagg   6240
gtggtgtgac ttgttatagc ctttagagct gcgaaagcgc gtatggattt ggctcatcag   6300
gccagattga gggtctgtgg acacatgtca tgttagtgta cttcaatcgc cccctggata   6360
tagccccgac aataggccgt ggcctcattt ttttgccttc cgcacatttc cattgctcgg   6420
tacccacacc ttgcttctcc tgcacttgcc aaccttaata ctggtttaca ttgaccaaca   6480
tcttacaagc ggggggcttg tctagggtat atataaacag tggctctccc aatcggttgc   6540
cagtctcttt tttcctttct ttccccacag attcgaaatc taaactacac atcacacaat   6600
gcctgttact gacgtcctta agcgaaagtc cggtgtcatc gtcggcgacg atgtccgagc   6660
cgtgagtatc cacgacaaga tcagtgtcga gacgacgcgt tttgtgtaat gacacaatcc   6720
gaaagtcgct agcaacacac actctctaca caaactaacc cagctctcca tggctgagga   6780
taagaccaag gtcgagttcc ctaccctgac tgagctgaag cactctatcc ctaacgcttg   6840
ctttgagtcc aacctcggac tctcgctcta ctacactgcc cgagcgatct tcaacgcatc   6900
tgcctctgct gctctgctct acgctgcccg atctactccc ttcattgccg ataacgttct   6960
gctccacgct ctggtttgcg ccacctacat ctacgtgcag ggtgtcatct tctggggttt   7020
ctttaccgtc ggtcacgact gtggtcactc tgccttctcc cgataccact ccgtcaactt   7080
catcattggc tgcatcatgc actctgccat tctgactccc ttcgagtcct ggcgagtgac   7140
ccaccgacac catcacaaga acactggcaa cattgataag gacgagatct tctaccctca   7200
tcggtccgtc aaggacctcc aggacgtgcg acaatgggtc tacaccctcg gaggtgcttg   7260
gtttgtctac ctgaaggtcg gatatgctcc tcgaaccatg tcccactttg accccctggga   7320
ccctctcctg cttcgacgag cctccgctgt catcgtgtcc ctcggagtct gggctgcctt   7380
cttcgctgcc tacgcctacc tcacatactc gctcggcttt gccgtcatgg gcctctacta   7440
ctatgctcct ctctttgtct ttgcttcgtt cctcgtcatt actaccttct tgcatcacaa   7500
cgacgaagct actccctggt acggtgactc ggagtggacc tacgtcaagg gcaacctgag   7560
ctccgtcgac cgatcgtacg gagctttcgt ggacaacctg tctcaccaca ttggcaccca   7620
ccaggtccat cacttgttcc ctatcattcc ccactacaag ctcaacgaag ccaccaagca   7680
ctttgctgcc gcttaccctc acctcgtgag acgtaacgac gagcccatca ttactgcctt   7740
cttcaagacc gctcacctct ttgtcaacta cggagctgtg cccgagactg ctcagatttt   7800
caccctcaaa gagtctgccg ctgcagccaa ggccaagagc gactaagcgg ccgcaagtgt   7860
ggatggggaa gtgagtgccc ggttctgtgt gcacaattgg caatccaaga tggatggatt   7920
caacacaggg atatagcgag ctacgtggtg gtgcgaggat atagcaacgg atatttatgt   7980
ttgacacttg agaatgtacg atacaagcac tgtccaagta caatactaaa catactgtac   8040
atactcatac tcgtacccgg gcaacggttt cacttgagtg cagtggctag tgctcttact   8100
cgtacagtgt gcaatactgc gtatcatagt ctttgatgta tatcgtattc attcatgtta   8160
gttgc                                                               8165
```

<210> SEQ ID NO 41

-continued

<211> LENGTH: 8015
<212> TYPE: DNA
<213> ORGANISM: Artificial Sequence
<220> FEATURE:
<223> OTHER INFORMATION: Plasmid pMLPAT-17

<400> SEQUENCE: 41

```
ctccatggtc gggtccgtca cccgacccac aaaggccctg ctctatggat cagccctctt     60
cagtttctgc tcattgctca atgtggtcca ggtgttctcc atactcctgc agccgttctc    120
gaagcgtctc ttctttgaag tgaacgctcg cgtggccggc tccatgtgga aggttatgca    180
gctgattatg gagaaaaagc acaaggccgc catcaccttc tcaggagaca agatccctca    240
ccacgagagt gccatcgtct ttggcaacca ccggtccttt gtcgactttt acatgtttca    300
caccgttgct gctcggagag gcatgctcaa ctatatgaag tactttgcca aggactctct    360
gaaatacatt ccattctatg gatggggcat gtggatcatg ggaatgctat tcatcaatcg    420
caactggcag caggatcagc tcaagatcaa caagatgttt gcacggatat tggacatcca    480
agcgcccgtt tgggtcgcca gtttcttgga gggctctcgg ttgacgccca gcaaactggc    540
tgcctctcaa aagttcatgc tgggacgcgg attgcctctg ctgtcaaacg tcatgatgcc    600
caggaccaag ggattcattg cctgtgtcaa caaattccgg ggaactcatg tgaaatgtgt    660
ttatgatttc acgttcgcct actaccacaa gaccaagggc tttggagtgc ctccagatct    720
ggtccgtgtt cacactggcc agctcagccc cgagtacaaa ttccatgttc atgtgagacg    780
ctatcagctc gacgatctgc ccacggatga ggagaagctg agcgagtggg tggtccaaaa    840
gtatgtggag aaggacgcct tttggagca gatgaaggag aattggacag atggtattga    900
tgggggtgtg tggtcagaga actggatgtg agcggccgca agtgtggatg gggaagtgag    960
tgcccggttc tgtgtgcaca attggcaatc caagatggat ggattcaaca cagggatata   1020
gcgagctacg tggtggtgcg aggatatagc aacggatatt tatgtttgac acttgagaat   1080
gtacgataca agcactgtcc aagtacaata ctaaacatac tgtacatact catactcgta   1140
cccgggcaac ggtttcactt gagtgcagtg gctagtgctc ttactcgtac agtgtgcaat   1200
actgcgtatc atagtctttg atgtatatcg tattcattca tgttagttgc gtacgagccg   1260
gaagcataaa gtgtaaagcc tggggtgcct aatgagtgag ctaactcaca ttaattgcgt   1320
tgcgctcact gcccgctttc cagtcgggaa acctgtcgtg ccagctgcat taatgaatcg   1380
gccaacgcgc ggggagaggc ggtttgcgta ttgggcgctc ttccgcttcc tcgctcactg   1440
actcgctgcg ctcggtcgtt cggctgcggc gagcggtatc agctcactca aaggcggtaa   1500
tacggttatc cacagaatca ggggataacg caggaaagaa catgtgagca aaaggccagc   1560
aaaaggccag gaaccgtaaa aaggccgcgt tgctggcgtt tttccatagg ctccgccccc   1620
ctgacgagca tcacaaaaat cgacgctcaa gtcagaggtg gcgaaacccg acaggactat   1680
aaagatacca ggcgtttccc cctggaagct ccctcgtgcg ctctcctgtt ccgaccctgc   1740
cgcttaccgg atacctgtcc gcctttctcc cttcgggaag cgtggcgctt tctcatagct   1800
cacgctgtag gtatctcagt tcggtgtagg tcgttcgctc caagctgggc tgtgtgcacg   1860
aaccccccgt tcagcccgac cgctgcgcct tatccggtaa ctatcgtctt gagtccaacc   1920
cggtaagaca cgacttatcg ccactggcag cagccactgg taacaggatt agcagagcga   1980
ggtatgtagg cggtgctaca gagttcttga agtggtggcc taactacggc tacactagaa   2040
ggacagtatt tggtatctgc gctctgctga agccagttac cttcggaaaa agagttggta   2100
gctcttgatc cggcaaacaa accaccgctg gtagcggtgg tttttttgtt tgcaagcagc   2160
```

-continued

```
agattacgcg cagaaaaaaa ggatctcaag aagatccttt gatcttttct acggggtctg   2220
acgctcagtg gaacgaaaac tcacgttaag ggattttggt catgagatta tcaaaaagga   2280
tcttcaccta gatcctttta aattaaaaat gaagttttaa atcaatctaa agtatatatg   2340
agtaaacttg gtctgacagt taccaatgct taatcagtga ggcacctatc tcagcgatct   2400
gtctatttcg ttcatccata gttgcctgac tccccgtcgt gtagataact acgatacggg   2460
agggcttacc atctggcccc agtgctgcaa tgataccgcg agacccacgc tcaccggctc   2520
cagatttatc agcaataaac cagccagccg gaagggccga gcgcagaagt ggtcctgcaa   2580
ctttatccgc ctccatccag tctattaatt gttgccggga agctagagta agtagttcgc   2640
cagttaatag tttgcgcaac gttgttgcca ttgctacagg catcgtggtg tcacgctcgt   2700
cgtttggtat ggcttcattc agctccggtt cccaacgatc aaggcgagtt acatgatccc   2760
ccatgttgtg caaaaaagcg gttagctcct tcggtcctcc gatcgttgtc agaagtaagt   2820
tggccgcagt gttatcactc atggttatgg cagcactgca taattctctt actgtcatgc   2880
catccgtaag atgcttttct gtgactggtg agtactcaac caagtcattc tgagaatagt   2940
gtatgcggcg accgagttgc tcttgcccgg cgtcaatacg ggataatacc gcgccacata   3000
gcagaacttt aaaagtgctc atcattggaa aacgttcttc ggggcgaaaa ctctcaagga   3060
tcttaccgct gttgagatcc agttcgatgt aacccactcg tgcacccaac tgatcttcag   3120
catcttttac tttcaccagc gtttctgggt gagcaaaaac aggaaggcaa aatgccgcaa   3180
aaaagggaat aagggcgaca cggaaatgtt gaatactcat actcttcctt tttcaatatt   3240
attgaagcat ttatcagggt tattgtctca tgagcggata catatttgaa tgtatttaga   3300
aaaataaaca aataggggtt ccgcgcacat ttccccgaaa agtgccacct gacgcgccct   3360
gtagcggcgc attaagcgcg gcgggtgtgg tggttacgcg cagcgtgacc gctacacttg   3420
ccagcgccct agcgcccgct cctttcgctt tcttcccttc ctttctcgcc acgttcgccg   3480
gctttccccg tcaagctcta aatcgggggc tccctttagg gttccgattt agtgctttac   3540
ggcacctcga ccccaaaaaa cttgattagg gtgatggttc acgtagtggg ccatcgccct   3600
gatagacggt ttttcgccct ttgacgttgg agtccacgtt ctttaatagt ggactcttgt   3660
tccaaactgg aacaacactc aaccctatct cggtctattc ttttgattta taagggattt   3720
tgccgatttc ggcctattgg ttaaaaaatg agctgattta acaaaaattt aacgcgaatt   3780
ttaacaaaat attaacgctt acaatttcca ttcgccattc aggctgcgca actgttggga   3840
agggcgatcg gtgcgggcct cttcgctatt acgccagctg gcgaaagggg gatgtgctgc   3900
aaggcgatta agttgggtaa cgccagggtt ttcccagtca cgacgttgta aaacgacggc   3960
cagtgaattg taatacgact cactataggg cgaattgggt accgggcccc ccctcgaggt   4020
cgatggtgtc gataagcttg atatcgaatt catgtcacac aaaccgatct tcgcctcaag   4080
gaaacctaat tctacatccg agagactgcc gagatccagt ctacactgat taattttcgg   4140
gccaataatt taaaaaaatc gtgttatata atattatatg tattatatat atacatcatg   4200
atgatactga cagtcatgtc ccattgctaa atagacagac tccatctgcc gcctccaact   4260
gatgttctca atatttaagg ggtcatctcg cattgtttaa taataaacag actccatcta   4320
ccgcctccaa atgatgttct caaaatatat tgtatgaact tatttttatt acttagtatt   4380
attagacaac ttacttgctt tatgaaaaac acttcctatt taggaaacaa tttataatgg   4440
cagttcgttc atttaacaat ttatgtagaa taaatgttat aaatgcgtat gggaaatctt   4500
```

-continued

```
aaatatggat agcataaatg atatctgcat tgcctaattc gaaatcaaca gcaacgaaaa   4560
aaatcccttg tacaacataa atagtcatcg agaaatatca actatcaaag aacagctatt   4620
cacacgttac tattgagatt attattggac gagaatcaca cactcaactg tctttctctc   4680
ttctagaaat acaggtacaa gtatgtacta ttctcattgt tcatacttct agtcatttca   4740
tcccacatat tccttggatt tctctccaat gaatgacatt ctatcttgca aattcaacaa   4800
ttataataag atataccaaa gtagcggtat agtggcaatc aaaaagcttc tctggtgtgc   4860
ttctcgtatt tatttttatt ctaatgatcc attaaaggta tatatttatt tcttgttata   4920
taatcctttt gtttattaca tgggctggat acataaaggt attttgattt aattttttgc   4980
ttaaattcaa tccccccctcg ttcagtgtca actgtaatgg taggaaatta ccatactttt   5040
gaagaagcaa aaaaaatgaa agaaaaaaaa aatcgtattt ccaggttaga cgttccgcag   5100
aatctagaat gcggtatgcg gtacattgtt cttcgaacgt aaaagttgcg ctccctgaga   5160
tattgtacat ttttgctttt acaagtacaa gtacatcgta caactatgta ctactgttga   5220
tgcatccaca acagtttgtt ttgttttttt ttgttttttt tttttctaat gattcattac   5280
cgctatgtat acctacttgt acttgtagta agccgggtta ttggcgttca attaatcata   5340
gacttatgaa tctgcacggt gtgcgctgcg agttactttt agcttatgca tgctacttgg   5400
gtgtaatatt gggatctgtt cggaaatcaa cggatgctca atcgatttcg acagtaatta   5460
attaagtcat acacaagtca gctttcttcg agcctcatat aagtataagt agttcaacgt   5520
attagcactg tacccagcat ctccgtatcg agaaacacaa caacatgccc cattggacag   5580
atcatgcgga tacacaggtt gtgcagtatc atacatactc gatcagacag gtcgtctgac   5640
catcatacaa gctgaacaag cgctccatac ttgcacgctc tctatataca cagttaaatt   5700
acatatccat agtctaacct ctaacagtta atcttctggt aagcctccca gccagccttc   5760
tggtatcgct tggcctcctc aataggatct cggttctggc cgtacagacc tcggccgaca   5820
attatgatat ccgttccggt agacatgaca tcctcaacag ttcggtactg ctgtccgaga   5880
gcgtctccct tgtcgtcaag acccaccccg ggggtcagaa taagccagtc ctcagagtcg   5940
cccttaggtc ggttctgggc aatgaagcca accacaaact cggggtcgga tcgggcaagc   6000
tcaatggtct gcttggagta ctcgccagtg gccagagagc ccttgcaaga cagctcggcc   6060
agcatgagca gacctctggc cagcttctcg ttgggagagg ggactaggaa ctccttgtac   6120
tgggagttct cgtagtcaga gacgtcctcc ttcttctgtt cagagacagt ttcctcggca   6180
ccagctcgca ggccagcaat gattccggtt ccgggtacac cgtgggcgtt ggtgatatcg   6240
gaccactcgg cgattcggtg acaccggtac tggtgcttga cagtgttgcc aatatctgcg   6300
aactttctgt cctcgaacag gaagaaaccg tgcttaagag caagttcctt gagggggagc   6360
acagtgccgg cgtaggtgaa gtcgtcaatg atgtcgatat gggttttgat catgcacaca   6420
taaggtccga ccttatcggc aagctcaatg agctccttgg tggtggtaac atccagagaa   6480
gcacacaggt tggttttctt ggctgccacg agcttgagca ctcgagcggc aaaggcggac   6540
ttgtggacgt tagctcgagc ttcgtaggag ggcattttgg tggtgaagag gagactgaaa   6600
taaatttagt ctgcagaact tttatcggaa accttatctg gggcagtgaa gtatatgtta   6660
tggtaatagt tacgagttag ttgaacttat agatagactg gactatacgg ctatcggtcc   6720
aaattagaaa gaacgtcaat ggctctctgg gcgtcgcctt tgccgacaaa aatgtgatca   6780
tgatgaaagc cagcaatgac gttgcagctg atattgttgt cggccaaccg cgccgaaaac   6840
gcagctgtca gacccacagc ctccaacgaa gaatgtatcg tcaaagtgat ccaagcacac   6900
```

```
tcatagttgg agtcgtactc caaaggcggc aatgacgagt cagacagata ctcgtcgact   6960

caggcgacga cggaattcct gcagcccatc tgcagaattc aggagagacc gggttggcgg   7020

cgtatttgtg tcccaaaaaa cagccccaat tgccccggag aagacggcca ggccgcctag   7080

atgacaaatt caacaactca cagctgactt tctgccattg ccactagggg ggggcctttt   7140

tatatggcca agccaagctc tccacgtcgg ttgggctgca cccaacaata aatgggtagg   7200

gttgcaccaa caaagggatg ggatgggggg tagaagatac gaggataacg gggctcaatg   7260

gcacaaataa gaacgaatac tgccattaag actcgtgatc cagcgactga caccattgca   7320

tcatctaagg gcctcaaaac tacctcggaa ctgctgcgct gatctggaca ccacagaggt   7380

tccgagcact ttaggttgca ccaaatgtcc caccaggtgc aggcagaaaa cgctggaaca   7440

gcgtgtacag tttgtcttaa caaaaagtga gggcgctgag gtcgagcagg gtggtgtgac   7500

ttgttatagc ctttagagct gcgaaagcgc gtatggattt ggctcatcag gccagattga   7560

gggtctgtgg acacatgtca tgttagtgta cttcaatcgc cccctggata tagccccgac   7620

aataggccgt ggcctcattt ttttgccttc cgcacatttc cattgctcgg tacccacacc   7680

ttgcttctcc tgcacttgcc aaccttaata ctggtttaca ttgaccaaca tcttacaagc   7740

ggggggcttg tctagggtat atataaacag tggctctccc aatcggttgc cagtctcttt   7800

tttcctttct ttccccacag attcgaaatc taaactacac atcacacaat gcctgttact   7860

gacgtcctta agcgaaagtc cggtgtcatc gtcggcgacg atgtccgagc cgtgagtatc   7920

cacgacaaga tcagtgtcga gacgacgcgt tttgtgtaat gacacaatcc gaaagtcgct   7980

agcaacacac actctctaca caaactaacc cagct                              8015
```

<210> SEQ ID NO 42
<211> LENGTH: 32
<212> TYPE: DNA
<213> ORGANISM: Artificial Sequence
<220> FEATURE:
<223> OTHER INFORMATION: Primer LPAT-Re-5-1

<400> SEQUENCE: 42

```
gatcgagctc gacattgagc attgatctat tt                                   32
```

<210> SEQ ID NO 43
<211> LENGTH: 41
<212> TYPE: DNA
<213> ORGANISM: Artificial Sequence
<220> FEATURE:
<223> OTHER INFORMATION: Primer LPAT-Re-5-2

<400> SEQUENCE: 43

```
gactatcgat accatggtcg ggcaatgaga acggcagcaa g                         41
```

<210> SEQ ID NO 44
<211> LENGTH: 1129
<212> TYPE: DNA
<213> ORGANISM: Yarrowia lipolytica

<400> SEQUENCE: 44

```
gatcgagctc gacattgagc attgatctat ttgtttagtt tagtacgtac gtagagtagt     60

tggttattgt atactggata ctggtcggat agtcgtgtac aagtacagta tatacttgta    120

gtttggaaca ctagtcacaa gtatagttaa taacagtata gtatatactt ctactgtaca    180

tatagttaca aaacagtaca gtatatactt ctactgtaca tactgtagtt tcatggttga    240
```

-continued

```
tataggtgaa aatgacatgg tatcccgctt cccaatgact gatacgagca acaaacaatt    300

ctctctaata gatgttcatt ataaccacac tgtacggtaa ttatatcgta gacagtgtac    360

agtattagaa cgtgtttttg atcccaagtt ggtggaaatg ttgagttgag atgagatgat    420

aatgttatca gcatgagggg tggatgtata cagtaggaga aggagtatgg gcagttgtgc    480

ggtagcagcg tctctgaatc acacaaagcc gggcttacag cagaggcaag aatggcgcca    540

tgtgcctgcg caatcaaggg cgtgaaccac ggcttgattc cacggcttga tgccacagct    600

taatgccaca tgccacagca taataccacg gcatgacccc gctgactcca accttcattt    660

cggcacgtgt aggtgcacaa gggacttcaa gaggggccaa tttcatgcgg acacatggcg    720

caaaaaacgc ccgactttga ttacacagac acgtaataac gacgaagccg agatgagcac    780

acgtggccaa gtctgccaat ggccccctgg accccccctga caaagtttcc caacaagccc    840

agccgtgcat ggtgtgtttt tgtgcggaga cacacgccaa ttaggctcat ttgagggtat    900

gcagcgaaaa aaaattagtg tgggtagttt gtttgcagga atcaagtggg tggttgaaaa    960

acaagaaaga gcgacgacaa gagagagaga aaaagagaga gagactccat aaagcgtgca   1020

tcaaaattaa ggtgtgtgac tatccgaaaa ccaaacatga acagttggat atatgtcgct   1080

gtgattgcag ttgctgccgt tctcattgcc cgaccatgga tcgatgatc               1129
```

<210> SEQ ID NO 45
<211> LENGTH: 849
<212> TYPE: DNA
<213> ORGANISM: Yarrowia lipolytica
<220> FEATURE:
<221> NAME/KEY: misc_feature
<223> OTHER INFORMATION: LPAAT1
<220> FEATURE:
<221> NAME/KEY: CDS
<222> LOCATION: (1)..(849)

<400> SEQUENCE: 45

```
atg tcc gtt gca tcc aag ctc gtc ttc tac gtc cgc gcc gcc atc gcc       48
Met Ser Val Ala Ser Lys Leu Val Phe Tyr Val Arg Ala Ala Ile Ala
1               5                   10                  15

gtg gtc atc ttt gcc gcc tgt gcc acc tac ggc gtg ctg gcg tcc acc       96
Val Val Ile Phe Ala Ala Cys Ala Thr Tyr Gly Val Leu Ala Ser Thr
            20                  25                  30

att ctc acc gcc atc ggc aag cag ggc ctg gcc caa tgg acc gtt gcc      144
Ile Leu Thr Ala Ile Gly Lys Gln Gly Leu Ala Gln Trp Thr Val Ala
        35                  40                  45

aga gcc ttc tac tac tcg gtg cgc atc ttc ctg ggt atc agc atc aag      192
Arg Ala Phe Tyr Tyr Ser Val Arg Ile Phe Leu Gly Ile Ser Ile Lys
    50                  55                  60

ctg cgt agc cgg cag gtg acc gga acc gcc ggt ctg gat gcc tcc aag      240
Leu Arg Ser Arg Gln Val Thr Gly Thr Ala Gly Leu Asp Ala Ser Lys
65                  70                  75                  80

atc cag gtc gcc aac acc acc aag ccc att gac gac atc acc aaa cac      288
Ile Gln Val Ala Asn Thr Thr Lys Pro Ile Asp Asp Ile Thr Lys His
                85                  90                  95

ctg ccc cga cca tgc att ctg att tcc aac cac cag aac gaa atg gac      336
Leu Pro Arg Pro Cys Ile Leu Ile Ser Asn His Gln Asn Glu Met Asp
            100                 105                 110

att ctg gtg ctc ggt cgc atc ttc ccc cag tac tgc tcc gtc acc gcc      384
Ile Leu Val Leu Gly Arg Ile Phe Pro Gln Tyr Cys Ser Val Thr Ala
        115                 120                 125

aaa aag gcc ctc aag tgg tac cct ctg ctg ggc cag ttc atg gcg ctg      432
Lys Lys Ala Leu Lys Trp Tyr Pro Leu Leu Gly Gln Phe Met Ala Leu
    130                 135                 140
```

```
tcc ggc acc atc ttc ctg gac cga aag gac cga acc aag tcc gtg cag      480
Ser Gly Thr Ile Phe Leu Asp Arg Lys Asp Arg Thr Lys Ser Val Gln
145                 150                 155                 160

acc ctc ggc ggc gcc gtc aag acc atc cag agc ggc aac gga ggc aag      528
Thr Leu Gly Gly Ala Val Lys Thr Ile Gln Ser Gly Asn Gly Gly Lys
                165                 170                 175

ggc cag agc gtc ttc atg ttc ccc gag gga acc cga tcc tac tcc aag      576
Gly Gln Ser Val Phe Met Phe Pro Glu Gly Thr Arg Ser Tyr Ser Lys
            180                 185                 190

gac gtc ggc atc atg ccc ttc aag aag ggc tgt ttc cac ctg gcg gtc      624
Asp Val Gly Ile Met Pro Phe Lys Lys Gly Cys Phe His Leu Ala Val
        195                 200                 205

cag tcg ggc gct ccc att gtc ccc gtg gtg gtc cag aac acc tcc cga      672
Gln Ser Gly Ala Pro Ile Val Pro Val Val Val Gln Asn Thr Ser Arg
    210                 215                 220

atg ttt tct ttc ggc cga ggc aag ctg gac gcc gga gag atc ctt gtc      720
Met Phe Ser Phe Gly Arg Gly Lys Leu Asp Ala Gly Glu Ile Leu Val
225                 230                 235                 240

gac gtc ctg agc ccc att gag acc aag ggt ctg gac gcc agc aac gtc      768
Asp Val Leu Ser Pro Ile Glu Thr Lys Gly Leu Asp Ala Ser Asn Val
                245                 250                 255

gac gct ctc atg gcc acc act tat aag gcc atg tgc gag act gcc gac      816
Asp Ala Leu Met Ala Thr Thr Tyr Lys Ala Met Cys Glu Thr Ala Asp
            260                 265                 270

cag att ggc tac gct ggc cag aag act cag tag                          849
Gln Ile Gly Tyr Ala Gly Gln Lys Thr Gln
        275                 280


<210> SEQ ID NO 46
<211> LENGTH: 282
<212> TYPE: PRT
<213> ORGANISM: Yarrowia lipolytica

<400> SEQUENCE: 46

Met Ser Val Ala Ser Lys Leu Val Phe Tyr Val Arg Ala Ala Ile Ala
1               5                   10                  15

Val Val Ile Phe Ala Ala Cys Ala Thr Tyr Gly Val Leu Ala Ser Thr
            20                  25                  30

Ile Leu Thr Ala Ile Gly Lys Gln Gly Leu Ala Gln Trp Thr Val Ala
        35                  40                  45

Arg Ala Phe Tyr Tyr Ser Val Arg Ile Phe Leu Gly Ile Ser Ile Lys
    50                  55                  60

Leu Arg Ser Arg Gln Val Thr Gly Thr Ala Gly Leu Asp Ala Ser Lys
65                  70                  75                  80

Ile Gln Val Ala Asn Thr Thr Lys Pro Ile Asp Asp Ile Thr Lys His
                85                  90                  95

Leu Pro Arg Pro Cys Ile Leu Ile Ser Asn His Gln Asn Glu Met Asp
            100                 105                 110

Ile Leu Val Leu Gly Arg Ile Phe Pro Gln Tyr Cys Ser Val Thr Ala
        115                 120                 125

Lys Lys Ala Leu Lys Trp Tyr Pro Leu Leu Gly Gln Phe Met Ala Leu
    130                 135                 140

Ser Gly Thr Ile Phe Leu Asp Arg Lys Asp Arg Thr Lys Ser Val Gln
145                 150                 155                 160

Thr Leu Gly Gly Ala Val Lys Thr Ile Gln Ser Gly Asn Gly Gly Lys
                165                 170                 175

Gly Gln Ser Val Phe Met Phe Pro Glu Gly Thr Arg Ser Tyr Ser Lys
```

```
            180                 185                 190

Asp Val Gly Ile Met Pro Phe Lys Lys Gly Cys Phe His Leu Ala Val
        195                 200                 205

Gln Ser Gly Ala Pro Ile Val Pro Val Val Val Gln Asn Thr Ser Arg
    210                 215                 220

Met Phe Ser Phe Gly Arg Gly Lys Leu Asp Ala Gly Glu Ile Leu Val
225                 230                 235                 240

Asp Val Leu Ser Pro Ile Glu Thr Lys Gly Leu Asp Ala Ser Asn Val
                245                 250                 255

Asp Ala Leu Met Ala Thr Thr Tyr Lys Ala Met Cys Glu Thr Ala Asp
            260                 265                 270

Gln Ile Gly Tyr Ala Gly Gln Lys Thr Gln
        275                 280


<210> SEQ ID NO 47
<211> LENGTH: 672
<212> TYPE: DNA
<213> ORGANISM: Yarrowia lipolytica
<220> FEATURE:
<221> NAME/KEY: misc_feature
<223> OTHER INFORMATION: LPAAT2
<220> FEATURE:
<221> NAME/KEY: CDS
<222> LOCATION: (1)..(672)

<400> SEQUENCE: 47

atg gtg gtc gtg gac gat gtt ctc ggt aat cat cta tca aga tac gac       48
Met Val Val Val Asp Asp Val Leu Gly Asn His Leu Ser Arg Tyr Asp
1               5                   10                  15

tat atg atc tac gca cta atc aac aac cag cat tgc gcc aag tcg cac       96
Tyr Met Ile Tyr Ala Leu Ile Asn Asn Gln His Cys Ala Lys Ser His
            20                  25                  30

ctt gca ttc ctg tcc tgg aaa cac atc ttt tct ctc ttt agc ctc agc      144
Leu Ala Phe Leu Ser Trp Lys His Ile Phe Ser Leu Phe Ser Leu Ser
        35                  40                  45

aag att ctg ccc ttc tac cga ctt gac gaa aac tgg atg ttc gaa tca      192
Lys Ile Leu Pro Phe Tyr Arg Leu Asp Glu Asn Trp Met Phe Glu Ser
    50                  55                  60

gca gcc gac ctt gag aaa gaa cta gcc aag cta atc aac cct tac tgt      240
Ala Ala Asp Leu Glu Lys Glu Leu Ala Lys Leu Ile Asn Pro Tyr Cys
65                  70                  75                  80

ctg gtg ctg ttc cca gaa gtc tcg gtg gca acc cca caa ctt atc aga      288
Leu Val Leu Phe Pro Glu Val Ser Val Ala Thr Pro Gln Leu Ile Arg
                85                  90                  95

cga cat aga gag ctc tgc aga gcg tgt ttt gca cct gaa ctc act cat      336
Arg His Arg Glu Leu Cys Arg Ala Cys Phe Ala Pro Glu Leu Thr His
            100                 105                 110

gta ctc tac cct cgc cac agc agc ttt gca gac ttc ata ttg gga ctg      384
Val Leu Tyr Pro Arg His Ser Ser Phe Ala Asp Phe Ile Leu Gly Leu
        115                 120                 125

aat aag ggc cag gct ctt agt tac atc tac gac gcc acc atc tcg tat      432
Asn Lys Gly Gln Ala Leu Ser Tyr Ile Tyr Asp Ala Thr Ile Ser Tyr
    130                 135                 140

act gac aag aaa gat aag att cta tgt aat cct gga aac ata gat act      480
Thr Asp Lys Lys Asp Lys Ile Leu Cys Asn Pro Gly Asn Ile Asp Thr
145                 150                 155                 160

ctg ttg act caa gtg gaa acg gtt cat gtt cac ata cac cga gaa cag      528
Leu Leu Thr Gln Val Glu Thr Val His Val His Ile His Arg Glu Gln
                165                 170                 175

tat cgt cgg ctg ccg cgc cac aga cgt ggt att cag aag tgg ctg gaa      576
```

-continued

```
Tyr Arg Arg Leu Pro Arg His Arg Arg Gly Ile Gln Lys Trp Leu Glu
            180                 185                 190

aac aca tgg gtc cac aag gat aag agt atc aga aag gcc tac aag cag      624
Asn Thr Trp Val His Lys Asp Lys Ser Ile Arg Lys Ala Tyr Lys Gln
        195                 200                 205

tct gga tca atc atg gat gat ggc aag ctc aag gag aag gat aag tga      672
Ser Gly Ser Ile Met Asp Asp Gly Lys Leu Lys Glu Lys Asp Lys
    210                 215                 220


<210> SEQ ID NO 48
<211> LENGTH: 223
<212> TYPE: PRT
<213> ORGANISM: Yarrowia lipolytica

<400> SEQUENCE: 48

Met Val Val Val Asp Asp Val Leu Gly Asn His Leu Ser Arg Tyr Asp
1               5                   10                  15

Tyr Met Ile Tyr Ala Leu Ile Asn Asn Gln His Cys Ala Lys Ser His
            20                  25                  30

Leu Ala Phe Leu Ser Trp Lys His Ile Phe Ser Leu Phe Ser Leu Ser
        35                  40                  45

Lys Ile Leu Pro Phe Tyr Arg Leu Asp Glu Asn Trp Met Phe Glu Ser
    50                  55                  60

Ala Ala Asp Leu Glu Lys Glu Leu Ala Lys Leu Ile Asn Pro Tyr Cys
65                  70                  75                  80

Leu Val Leu Phe Pro Glu Val Ser Val Ala Thr Pro Gln Leu Ile Arg
                85                  90                  95

Arg His Arg Glu Leu Cys Arg Ala Cys Phe Ala Pro Glu Leu Thr His
            100                 105                 110

Val Leu Tyr Pro Arg His Ser Ser Phe Ala Asp Phe Ile Leu Gly Leu
        115                 120                 125

Asn Lys Gly Gln Ala Leu Ser Tyr Ile Tyr Asp Ala Thr Ile Ser Tyr
    130                 135                 140

Thr Asp Lys Lys Asp Lys Ile Leu Cys Asn Pro Gly Asn Ile Asp Thr
145                 150                 155                 160

Leu Leu Thr Gln Val Glu Thr Val His Val His Ile His Arg Glu Gln
                165                 170                 175

Tyr Arg Arg Leu Pro Arg His Arg Arg Gly Ile Gln Lys Trp Leu Glu
            180                 185                 190

Asn Thr Trp Val His Lys Asp Lys Ser Ile Arg Lys Ala Tyr Lys Gln
        195                 200                 205

Ser Gly Ser Ile Met Asp Asp Gly Lys Leu Lys Glu Lys Asp Lys
    210                 215                 220


<210> SEQ ID NO 49
<211> LENGTH: 40
<212> TYPE: DNA
<213> ORGANISM: Artificial Sequence
<220> FEATURE:
<223> OTHER INFORMATION: Primer LPAT-Re-3-1

<400> SEQUENCE: 49

gactatcgat gcggccgcag actgcagcac aagaagtgct                           40


<210> SEQ ID NO 50
<211> LENGTH: 40
<212> TYPE: DNA
<213> ORGANISM: Artificial Sequence
<220> FEATURE:
```

-continued

<223> OTHER INFORMATION: Primer LPAT-Re-3-2

<400> SEQUENCE: 50
gatcctcgag tctagagcag ggtgttggag gggatggaga 40

<210> SEQ ID NO 51
<211> LENGTH: 938
<212> TYPE: DNA
<213> ORGANISM: Yarrowia lipolytica

<400> SEQUENCE: 51
gactatcgat gcggccgcag actgcagcac aagaagtgct tgtagctact ttaggagaga 60
gataggtaat atgaaacatt tttcagatcg acacccacgg cgaaccattg gctgtggagc 120
tatgggtgaa tggattaata tagcaacgaa atctacctcg attaccaacg caaaacgagc 180
ccactttctc tgtactgtgc tatatcgtgt ataccccagt tctcttagat cagtcgtacc 240
cgcccgtact gtcatggact attcaaactg ttggttttta gtctactcct acttgtacca 300
tgcttatgct cgatgtacca gctacttcgt ccgcggacgt gtctctataa taaccctgaa 360
agctgctcat tcctctaaaa gtcgtgacac cacctagtct tactcatcga gattgtatta 420
ctcatcgaga ttgtattact catcgagatt gtattactca tcttgatttt ctctcgtacg 480
atgttgttag taatcatggc cttccagccg aactctaccg accgaggtaa cttcacaagg 540
tttagacaga gtccaattat tcgaggagcc cataagtcta cctttaccta ctctactgta 600
gtgtgaagat gatcatgaga ggcatagatt ggattggaca gttggacggg tgacgaggga 660
gcagacaagt gcgagattgg cgttgttata tggactccag ggaccgtgaa ttgctcttaa 720
actggccgat attagcggct ggaaagatcc ttgtcccact ctcttctttg tctatcctgg 780
tgatccattt ttttgacagc taaaattaac tcgccgaaac acgtcggcat accgagatta 840
aattacaaaa gaagattaaa acgcgaccag caaaccgcaa cttccgcttt actcaacctc 900
tccatcccct ccaacaccct gctctagact cgaggatc 938

<210> SEQ ID NO 52
<211> LENGTH: 8411
<212> TYPE: DNA
<213> ORGANISM: Artificial Sequence
<220> FEATURE:
<223> OTHER INFORMATION: Plasmid pMLPAT2-Int

<400> SEQUENCE: 52
atttcgacag taattaatta agtcatacac aagtcagctt tcttcgagcc tcatataagt 60
ataagtagtt caacgtatta gcactgtacc cagcatctcc gtatcgagaa acacaacaac 120
atgccccatt ggacagatca tgcggataca caggttgtgc agtatcatac atactcgatc 180
agacaggtcg tctgaccatc atacaagctg aacaagcgct ccatacttgc acgctctcta 240
tatacacagt taaattacat atccatagtc taacctctaa cagttaatct tctggtaagc 300
ctcccagcca gccttctggt atcgcttggc ctcctcaata ggatctcggt tctggccgta 360
cagacctcgg ccgacaatta tgatatccgt tccggtagac atgacatcct caacagttcg 420
gtactgctgt ccgagagcgt ctcccttgtc gtcaagaccc accccggggg tcagaataag 480
ccagtcctca gagtcgccct taggtcggtt ctgggcaatg aagccaacca caaactcggg 540
gtcggatcgg gcaagctcaa tggtctgctt ggagtactcg ccagtggcca gagagccctt 600
gcaagacagc tcggccagca tgagcagacc tctggccagc ttctcgttgg gagaggggac 660
taggaactcc ttgtactggg agttctcgta gtcagagacg tcctccttct tctgttcaga 720

-continued

```
gacagtttcc tcggcaccag ctcgcaggcc agcaatgatt ccggttccgg gtacaccgtg    780
ggcgttggtg atatcggacc actcggcgat tcggtgacac cggtactggt gcttgacagt    840
gttgccaata tctgcgaact ttctgtcctc gaacaggaag aaaccgtgct taagagcaag    900
ttccttgagg gggagcacag tgccggcgta ggtgaagtcg tcaatgatgt cgatatgggt    960
tttgatcatg cacacataag gtccgacctt atcggcaagc tcaatgagct ccttggtggt   1020
ggtaacatcc agagaagcac acaggttggt tttcttggct gccacgagct tgagcactcg   1080
agcggcaaag gcggacttgt ggacgttagc tcgagcttcg taggagggca ttttggtggt   1140
gaagaggaga ctgaaataaa tttagtctgc agaacttttt atcggaacct tatctggggc   1200
agtgaagtat atgttatggt aatagttacg agttagttga acttatagat agactggact   1260
atacggctat cggtccaaat tagaaagaac gtcaatggct ctctgggcgt cgcctttgcc   1320
gacaaaaatg tgatcatgat gaaagccagc aatgacgttg cagctgatat tgttgtcggc   1380
caaccgcgcc gaaaacgcag ctgtcagacc cacagcctcc aacgaagaat gtatcgtcaa   1440
agtgatccaa gcacactcat agttggagtc gtactccaaa ggcggcaatg acgagtcaga   1500
cagatactcg tcgactcagg cgacgacgga attcctgcag cccatctgca gaattcagga   1560
gagaccgggt tggcggcgta tttgtgtccc aaaaaacagc cccaattgcc ccggagaaga   1620
cggccaggcc gcctagatga caaattcaac aactcacagc tgactttctg ccattgccac   1680
taggggggggg cctttttata tggccaagcc aagctctcca cgtcggttgg gctgcaccca   1740
acaataaatg ggtagggttg caccaacaaa gggatgggat gggggtaga agatacgagg   1800
ataacggggc tcaatggcac aaataagaac gaatactgcc attaagactc gtgatccagc   1860
gactgacacc attgcatcat ctaagggcct caaaactacc tcggaactgc tgcgctgatc   1920
tggacaccac agaggttccg agcactttag gttgcaccaa atgtcccacc aggtgcaggc   1980
agaaaacgct ggaacagcgt gtacagtttg tcttaacaaa aagtgagggc gctgaggtcg   2040
agcagggtgg tgtgacttgt tatagccttt agagctgcga aagcgcgtat ggatttggct   2100
catcaggcca gattgagggt ctgtggacac atgtcatgtt agtgtacttc aatcgccccc   2160
tggatatagc cccgacaata ggccgtggcc tcattttttt gccttccgca catttccatt   2220
gctcggtacc cacaccttgc ttctcctgca cttgccaacc ttaatactgg tttacattga   2280
ccaacatctt acaagcgggg ggcttgtcta gggtatatat aaacagtggc tctcccaatc   2340
ggttgccagt ctcttttttc ctttctttcc ccacagattc gaaatctaaa ctacacatca   2400
cacaatgcct gttactgacg tccttaagcg aaagtccggt gtcatcgtcg gcgacgatgt   2460
ccgagccgtg agtatccacg acaagatcag tgtcgagacg acgcgttttg tgtaatgaca   2520
caatccgaaa gtcgctagca acacacactc tctacacaaa ctaacccagc tctccatggt   2580
cgggtccgtc acccgaccca caaaggccct gctctatgga tcagccctct tcagtttctg   2640
ctcattgctc aatgtggtcc aggtgttctc catactcctg cagccgttct cgaagcgtct   2700
cttctttgaa gtgaacgctc gcgtggccgg ctccatgtgg aaggttatgc agctgattat   2760
ggagaaaaag cacaaggccg ccatcacctt ctcaggagac aagatccctc accacgagag   2820
tgccatcgtc tttggcaacc accggtcctt tgtcgacttt tacatgtttc acaccgttgc   2880
tgctcggaga ggcatgctca actatatgaa gtactttgcc aaggactctc tgaaatacat   2940
tccattctat ggatggggca tgtggatcat gggaatgcta ttcatcaatc gcaactggca   3000
gcaggatcag ctcaagatca acaagatgtt tgcacggata ttggacatcc aagcgcccgt   3060
```

-continued

```
ttgggtcgcc agtttcttgg agggctctcg gttgacgccc agcaaactgg ctgcctctca   3120

aaagttcatg ctgggacgcg gattgcctct gctgtcaaac gtcatgatgc ccaggaccaa   3180

gggattcatt gcctgtgtca acaaattccg ggaactcat gtgaaatgtg tttatgattt   3240

cacgttcgcc tactaccaca agaccaaggg ctttggagtg cctccagatc tggtccgtgt   3300

tcacactggc cagctcagcc ccgagtacaa attccatgtt catgtgagac gctatcagct   3360

cgacgatctg cccacggatg aggagaagct gagcgagtgg gtggtccaaa agtatgtgga   3420

gaaggacgcc tttttggagc agatgaagga gaattggaca gatggtattg atgggggtgt   3480

gtggtcagag aactggatgt gagcggccgc agactgcagc acaagaagtg cttgtagcta   3540

ctttaggaga gagataggta atatgaaaca tttttcagat cgacacccac ggcgaaccat   3600

tggctgtgga gctatgggtg aatggattaa tatagcaacg aaatctacct cgattaccaa   3660

cgcaaaacga gcccactttc tctgtactgt gctatatcgt gtataccca gttctcttag   3720

atcagtcgta cccgcccgta ctgtcatgga ctattcaaac tgttggtttt tagtctactc   3780

ctacttgtac catgcttatg ctcgatgtac cagctacttc gtccgcggac gtgtctctat   3840

aataaccctg aaagctgctc attcctctaa aagtcgtgac accacctagt cttactcatc   3900

gagattgtat tactcatcga gattgtatta ctcatcgaga ttgtattact catcttgatt   3960

ttctctcgta cgatgttgtt agtaatcatg gccttccagc cgaactctac cgaccgaggt   4020

aacttcacaa ggtttagaca gagtccaatt attcgaggag cccataagtc tacctttacc   4080

tactctactg tagtgtgaag atgatcatga gaggcataga ttggattgga cagttggacg   4140

ggtgacgagg gagcagacaa gtgcgagatt ggcgttgtta tatggactcc agggaccgtg   4200

aattgctctt aaactggccg atattagcgg ctggaaagat ccttgtccca ctctcttctt   4260

tgtctatcct ggtgatccat ttttttgaca gctaaaatta actcgccgaa acacgtcggc   4320

ataccgagat taaattacaa aagaagatta aaacgcgacc agcaaaccgc aacttccgct   4380

ttactcaacc tctccatccc ctccaacacc ctgctctaga ctcgaggggg ggcccggtac   4440

ccaattcgcc ctatagtgag tcgtattaca attcactggc cgtcgtttta caacgtcgtg   4500

actgggaaaa ccctggcgtt acccaactta atcgccttgc agcacatccc cctttcgcca   4560

gctggcgtaa tagcgaagag gcccgcaccg atcgcccttc ccaacagttg cgcagcctga   4620

atggcgaatg gaaattgtaa gcgttaatat tttgttaaaa ttcgcgttaa atttttgtta   4680

aatcagctca ttttttaacc aataggccga aatcggcaaa atcccttata aatcaaaaga   4740

atagaccgag atagggttga gtgttgttcc agtttggaac aagagtccac tattaaagaa   4800

cgtggactcc aacgtcaaag ggcgaaaaac cgtctatcag ggcgatggcc cactacgtga   4860

accatcaccc taatcaagtt ttttggggtc gaggtgccgt aaagcactaa atcggaaccc   4920

taaagggagc ccccgattta gagcttgacg gggaaagccg gcgaacgtgg cgagaaagga   4980

agggaagaaa gcgaaaggag cgggcgctag ggcgctggca agtgtagcgg tcacgctgcg   5040

cgtaaccacc acacccgccg cgcttaatgc gccgctacag ggcgcgtcag gtggcacttt   5100

tcggggaaat gtgcgcggaa cccctatttg tttatttttc taaatacatt caaatatgta   5160

tccgctcatg agacaataac cctgataaat gcttcaataa tattgaaaaa ggaagagtat   5220

gagtattcaa catttccgtg tcgcccttat tccctttttt gcggcatttt gccttcctgt   5280

ttttgctcac ccagaaacgc tggtgaaagt aaaagatgct gaagatcagt tgggtgcacg   5340

agtgggttac atcgaactgg atctcaacag cggtaagatc cttgagagtt ttcgccccga   5400

agaacgtttt ccaatgatga gcacttttaa agttctgcta tgtggcgcgg tattatcccg   5460
```

-continued

```
tattgacgcc gggcaagagc aactcggtcg ccgcatacac tattctcaga atgacttggt   5520
tgagtactca ccagtcacag aaaagcatct tacggatggc atgacagtaa gagaattatg   5580
cagtgctgcc ataaccatga gtgataacac tgcggccaac ttacttctga caacgatcgg   5640
aggaccgaag gagctaaccg cttttttgca caacatgggg gatcatgtaa ctcgccttga   5700
tcgttgggaa ccggagctga atgaagccat accaaacgac gagcgtgaca ccacgatgcc   5760
tgtagcaatg gcaacaacgt tgcgcaaact attaactggc gaactactta ctctagcttc   5820
ccggcaacaa ttaatagact ggatggaggc ggataaagtt gcaggaccac ttctgcgctc   5880
ggcccttccg gctggctggt ttattgctga taaatctgga gccggtgagc gtgggtctcg   5940
cggtatcatt gcagcactgg ggccagatgg taagccctcc cgtatcgtag ttatctacac   6000
gacggggagt caggcaacta tggatgaacg aaatagacag atcgctgaga taggtgcctc   6060
actgattaag cattggtaac tgtcagacca agtttactca tatatacttt agattgattt   6120
aaaacttcat ttttaattta aaaggatcta ggtgaagatc ctttttgata atctcatgac   6180
caaaatccct taacgtgagt tttcgttcca ctgagcgtca gaccccgtag aaaagatcaa   6240
aggatcttct tgagatcctt tttttctgcg cgtaatctgc tgcttgcaaa caaaaaaacc   6300
accgctacca gcggtggttt gtttgccgga tcaagagcta ccaactcttt ttccgaaggt   6360
aactggcttc agcagagcgc agataccaaa tactgtcctt ctagtgtagc cgtagttagg   6420
ccaccacttc aagaactctg tagcaccgcc tacatacctc gctctgctaa tcctgttacc   6480
agtggctgct gccagtggcg ataagtcgtg tcttaccggg ttggactcaa gacgatagtt   6540
accggataag gcgcagcggt cgggctgaac ggggggttcg tgcacacagc ccagcttgga   6600
gcgaacgacc tacaccgaac tgagatacct acagcgtgag ctatgagaaa gcgccacgct   6660
tcccgaaggg agaaaggcgg acaggtatcc ggtaagcggc agggtcggaa caggagagcg   6720
cacgagggag cttccagggg gaaacgcctg gtatctttat agtcctgtcg ggtttcgcca   6780
cctctgactt gagcgtcgat ttttgtgatg ctcgtcaggg gggcggagcc tatggaaaaa   6840
cgccagcaac gcggcctttt tacggttcct ggccttttgc tggccttttg ctcacatgtt   6900
ctttcctgcg ttatcccctg attctgtgga taaccgtatt accgcctttg agtgagctga   6960
taccgctcgc cgcagccgaa cgaccgagcg cagcgagtca gtgagcgagg aagcggaaga   7020
gcgcccaata cgcaaaccgc ctctccccgc gcgttggccg attcattaat gcagctggca   7080
cgacaggttt cccgactgga aagcgggcag tgagcgcaac gcaattaatg tgagttagct   7140
cactcattag gcaccccagg ctttacactt tatgcttccg gctcgtatgt tgtgtggaat   7200
tgtgagcgga taacaatttc acacaggaaa cagctatgac catgattacg ccaagctcga   7260
aattaaccct cactaaaggg aacaaaagct ggagctcgac attgagcatt gatctatttg   7320
tttagtttag tacgtacgta gagtagttgg ttattgtata ctggatactg gtcggatagt   7380
cgtgtacaag tacagtatat acttgtagtt tggaacacta gtcacaagta tagttaataa   7440
cagtatagta tatacttcta ctgtacatat agttacaaaa cagtacagta tatacttcta   7500
ctgtacatac tgtagtttca tggttgatat aggtgaaaat gacatggtat cccgcttccc   7560
aatgactgat acgagcaaca aacaattctc tctaatagat gttcattata accacactgt   7620
acggtaatta tatcgtagac agtgtacagt attagaacgt gtttttgatc ccaagttggt   7680
ggaaatgttg agttgagatg agatgataat gttatcagca tgaggggtgg atgtatacag   7740
taggagaagg agtatgggca gttgtgcggt agcagcgtct ctgaatcaca caaagccggg   7800
```

-continued

```
cttacagcag aggcaagaat ggcgccatgt gcctgcgcaa tcaagggcgt gaaccacggc   7860
ttgattccac ggcttgatgc cacagcttaa tgccacatgc cacagcataa taccacggca   7920
tgaccccgct gactccaacc ttcatttcgg cacgtgtagg tgcacaaggg acttcaagag   7980
gggccaattt catgcggaca catggcgcaa aaaacgcccg actttgatta cacagacacg   8040
taataacgac gaagccgaga tgagcacacg tggccaagtc tgccaatggc cccctggacc   8100
cccctgacaa agtttcccaa caagcccagc cgtgcatggt gtgtttttgt gcggagacac   8160
acgccaatta ggctcatttg agggtatgca gcgaaaaaaa attagtgtgg gtagtttgtt   8220
tgcaggaatc aagtgggtgg ttgaaaaaca agaaagagcg acgacaagag agagagaaaa   8280
agagagagag actccataaa gcgtgcatca aaattaaggt gtgtgactat ccgaaaacca   8340
aacatgaaca gttggatata tgtcgctgtg attgcagttg ctgccgttct cattgcccga   8400
ccatggtatc g                                                         8411
```

<210> SEQ ID NO 53
<211> LENGTH: 7323
<212> TYPE: DNA
<213> ORGANISM: Artificial Sequence
<220> FEATURE:
<223> OTHER INFORMATION: Plasmid pZUF-MOD-1

<400> SEQUENCE: 53

```
gtacgagccg gaagcataaa gtgtaaagcc tggggtgcct aatgagtgag ctaactcaca     60
ttaattgcgt tgcgctcact gcccgctttc cagtcgggaa acctgtcgtg ccagctgcat    120
taatgaatcg gccaacgcgc ggggagaggc ggtttgcgta ttgggcgctc ttccgcttcc    180
tcgctcactg actcgctgcg ctcggtcgtt cggctgcggc gagcggtatc agctcactca    240
aaggcggtaa tacggttatc cacagaatca ggggataacg caggaaagaa catgtgagca    300
aaaggccagc aaaaggccag gaaccgtaaa aaggccgcgt tgctggcgtt tttccatagg    360
ctccgccccc ctgacgagca tcacaaaaat cgacgctcaa gtcagaggtg gcgaaacccg    420
acaggactat aaagatacca ggcgtttccc cctggaagct ccctcgtgcg ctctcctgtt    480
ccgaccctgc cgcttaccgg atacctgtcc gcctttctcc cttcgggaag cgtggcgctt    540
tctcatagct cacgctgtag gtatctcagt tcggtgtagg tcgttcgctc caagctgggc    600
tgtgtgcacg aaccccccgt tcagcccgac cgctgcgcct tatccggtaa ctatcgtctt    660
gagtccaacc cggtaagaca cgacttatcg ccactggcag cagccactgg taacaggatt    720
agcagagcga ggtatgtagg cggtgctaca gagttcttga agtggtggcc taactacggc    780
tacactagaa ggacagtatt tggtatctgc gctctgctga agccagttac cttcggaaaa    840
agagttggta gctcttgatc cggcaaacaa accaccgctg gtagcggtgg tttttttgtt    900
tgcaagcagc agattacgcg cagaaaaaaa ggatctcaag aagatccttt gatcttttct    960
acggggtctg acgctcagtg gaacgaaaac tcacgttaag ggattttggt catgagatta   1020
tcaaaaagga tcttcaccta gatcctttta aattaaaaat gaagttttaa atcaatctaa   1080
agtatatatg agtaaacttg gtctgacagt taccaatgct taatcagtga ggcacctatc   1140
tcagcgatct gtctatttcg ttcatccata gttgcctgac tccccgtcgt gtagataact   1200
acgatacggg agggcttacc atctggcccc agtgctgcaa tgataccgcg agacccacgc   1260
tcaccggctc cagatttatc agcaataaac cagccagccg gaagggccga gcgcagaagt   1320
ggtcctgcaa ctttatccgc ctccatccag tctattaatt gttgccggga agctagagta   1380
agtagttcgc cagttaatag tttgcgcaac gttgttgcca ttgctacagg catcgtggtg   1440
```

-continued

```
tcacgctcgt cgtttggtat ggcttcattc agctccggtt cccaacgatc aaggcgagtt   1500
acatgatccc ccatgttgtg caaaaaagcg gttagctcct tcggtcctcc gatcgttgtc   1560
agaagtaagt tggccgcagt gttatcactc atggttatgg cagcactgca taattctctt   1620
actgtcatgc catccgtaag atgcttttct gtgactggtg agtactcaac caagtcattc   1680
tgagaatagt gtatgcggcg accgagttgc tcttgcccgg cgtcaatacg ggataatacc   1740
gcgccacata gcagaacttt aaaagtgctc atcattggaa aacgttcttc ggggcgaaaa   1800
ctctcaagga tcttaccgct gttgagatcc agttcgatgt aacccactcg tgcacccaac   1860
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aatttttttgc ttaaattcaa tccccccctcg ttcagtgtca actgtaatgg taggaaatta   3780
```

-continued

```
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg ggggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact tttatcgga accttatctg gggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggcctttt tatatggcca agccaagctc tccacgtcgg ttgggctgca cccaacaata   5940
aatgggtagg gttgcaccaa caaagggatg ggatgggggg tagaagatac gaggataacg   6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
```

-continued

```
cgctggaaca gcgtgtacag tttgtcttaa caaaaagtga gggcgctgag gtcgagcagg   6240

gtggtgtgac ttgttatagc ctttagagct gcgaaagcgc gtatggattt ggctcatcag   6300

gccagattga gggtctgtgg acacatgtca tgttagtgta cttcaatcgc cccctggata   6360

tagccccgac aataggccgt ggcctcattt ttttgccttc cgcacatttc cattgctcgg   6420

tacccacacc ttgcttctcc tgcacttgcc aaccttaata ctggtttaca ttgaccaaca   6480

tcttacaagc ggggggcttg tctagggtat atataaacag tggctctccc aatcggttgc   6540

cagtctcttt tttcctttct ttccccacag attcgaaatc taaactacac atcacacaat   6600

gcctgttact gacgtcctta agcgaaagtc cggtgtcatc gtcggcgacg atgtccgagc   6660

cgtgagtatc cacgacaaga tcagtgtcga gacgacgcgt tttgtgtaat gacacaatcc   6720

gaaagtcgct agcaacacac actctctaca caaactaacc cagctctcca tggatccagg   6780

cctgttaacg gccattacgg cctgcaggat ccgaaaaaac ctcccacacc tccccctgaa   6840

cctgaaacat aaaatgaatg caattgttgt tgttaacttg tttattgcag cttataatgg   6900

ttacaaataa agcaatagca tcacaaattt cacaaataaa gcattttttt cactgcattc   6960

tagttgtggt ttgtccaaac tcatcaatgt atcttatcat gtctgcggcc gcaagtgtgg   7020

atggggaagt gagtgcccgg ttctgtgtgc acaattggca atccaagatg gatggattca   7080

acacagggat atagcgagct acgtggtggt gcgaggatat agcaacggat atttatgttt   7140

gacacttgag aatgtacgat acaagcactg tccaagtaca atactaaaca tactgtacat   7200

actcatactc gtacccgggc aacggtttca cttgagtgca gtggctagtg ctcttactcg   7260

tacagtgtgc aatactgcgt atcatagtct ttgatgtata tcgtattcat tcatgttagt   7320

tgc                                                                7323

<210> SEQ ID NO 54
<211> LENGTH: 28
<212> TYPE: DNA
<213> ORGANISM: Artificial Sequence
<220> FEATURE:
<223> OTHER INFORMATION: Primer PZUF-mod1

<400> SEQUENCE: 54

gatcccatgg atccaggcct gttaacgg                                       28


<210> SEQ ID NO 55
<211> LENGTH: 32
<212> TYPE: DNA
<213> ORGANISM: Artificial Sequence
<220> FEATURE:
<223> OTHER INFORMATION: Primer PZUF-mod2

<400> SEQUENCE: 55

gatcgcggcc gcagacatga taagatacat tg                                  32
```

*MORTIERELLA ALPINA* LYSOPHOSPHATIDIC ACID ACYLTRANSFERASE HOMOLOG FOR ALTERATION OF POLYUNSATURATED FATTY ACIDS AND OIL CONTENT IN OLEAGINOUS ORGANISMS

This application claims the benefit of U.S. patent application Ser. No. 60/689,031, filed Jun. 9, 2005 and 60/624,812, filed Nov. 4, 2004.

FIELD OF THE INVENTION

This invention is in the field of biotechnology. More specifically, this invention pertains to the identification of a nucleic acid fragment isolated from *Mortierella alpina* encoding a lysophosphatidic acid acyltransferase (LPAAT) homolog. This enzyme (identified herein as "LPAAT2") is useful for altering the quantity of oil in oleaginous organisms, such as oleaginous bacteria, yeast, algae and fungi.

BACKGROUND OF THE INVENTION

The present invention is in support of the development of an oleaginous yeast that accumulates oils enriched in long-chain ω-3 and/or ω-6 polyunsaturated fatty acids ("PUFAs"; e.g., 18:3, 18:4, 20:3, 20:4, 20:5, 22:6 fatty acids). Toward this end, the natural abilities of oleaginous yeast (mostly limited to 18:2 fatty acid production) have been enhanced by advances in genetic engineering, leading to the production of 20:4 (arachidonic acid or "ARA"), 20:5 (eicosapentaenoic acid or "EPA") and 22:6 (docosahexaenoic acid or "DHA") PUFAs in transformant *Yarrowia lipolytica*. These ω-3 and ω-6 fatty acids were produced by introducing and expressing heterologous genes encoding the ω-3/ω-6 biosynthetic pathway in the oleaginous host (see co-pending U.S. patent application Ser. Nos. 10/840,579 and No. 60/624,812, each entirely incorporated herein by reference). However, in addition to developing techniques to introduce the appropriate fatty acid desaturases and elongases into these particular host organisms, it is also necessary to increase the transfer of PUFAs into storage lipid pools following their synthesis.

As is well known in the art, the process of triacylglycerol (TAG) biosynthesis (wherein newly synthesized PUFAs are transferred into a host organism's storage lipid pools) requires the catalytic activity of various acyltransferases as most free fatty acids become esterified to coenzyme A (CoA) to yield acyl-CoAs. Specifically, a series of four reactions occur in the endoplasmic reticulum of the cell to form TAGs, as shown in the Table below.

TABLE 1

General Reactions Of de Novo Triacylglycerol Biosynthesis

| Reaction | Enzyme |
|---|---|
| sn-Glycerol-3-Phosphate → Lysophosphatidic Acid (1-acyl-sn-glycerol 3-phosphate or "LPA") | Glycerol-3-phosphate acyltransferase (GPAT); [E.C. 2.3.1.15]; esterifies 1st acyl-CoA to sn-1 position of sn-glycerol 3-phosphate |
| LPA → Phosphatidic Acid (1,2-diacylglycerol phosphate or "PA") | Lysophosphatidic acid acyltransferase (LPAAT) [E.C. 2.3.1.51]; esterifies 2nd acyl-CoA to sn-2 position of LPA |
| PA → 1,2-Diacylglycerol ("DAG") | Phosphatidic acid phosphatase [E.C. 3.1.3.4] removes a phosphate from PA |
| DAG → Triacylglycerol ("TAG") | Diacylglycerol acyltransferase (DGAT) [E.C. 2.3.1.20]; transfers acyl-CoA to the sn-3 position of DAG<br>Or<br>Phospholipid:diacylglycerol acyltransferase (PDAT) [E.C.2.3.1.158]; transfers fatty acyl-group from sn-2 positionof phosphatidylcholine to sn-3 position of DAG |

In addition to those acyltransferases above, acyl-CoA:cholesterol acyltransferases (ACATs), lecithin:cholesterol acyltransferases (LCATs) and lysophosphatidylcholine acyltransferases (LPCATs) are also intimately involved in the biosynthesis of TAGs. The role of each of these acyltransferases in regulating lipid acyl composition is largely mediated through their individual substrate specificities.

This application is concerned primarily with the second step in the synthesis of TAG (wherein LPA is converted to PA) limits the acyltransferase(s) of primary importance to LPAAT (also referred to as acyl-CoA:1-acyl-sn-glycerol-3-phosphate 2-O-acyltransferase, 1-acyl-sn-glycerol-3-phosphate acyltransferase, AGAT and/or 1-acylglycerolphosphate acyltransferase in the literature). By inspection of the LPAAT activities in isolated membranes from seed tissues, it has been shown that LPAAT specificities vary from species to species in accordance with the kinds of fatty acyl groups found in the sn-2 positions of the respective storage oils. Thus, the acyl-CoA specificity of LPAAT can dramatically affect the types of fatty acyl groups found in the sn-2 position of plant oils. Similarly, WO 2004/087902 (Example 6) compared the activity of LPAAT in microsomal membranes of the filamentous fungus *Mortierella alpina* to that of flax and sunflower. These results suggest that the *M. alpina* LPAAT displays a wide specificity for acyl-CoAs, which is in contrast to the LPAATs of flax and sunflower. Subsequently, two *Mortierella alpina* LPAATs (GenBank Accession Nos. CQ891250 and CQ891252, were isolated and expressed in *Saccharomyces cerevisiae*.

Although similar empirical data concerning the *Yarrowia lipolytica* LPAAT substrate specificity and its effect on final TAG composition is lacking, wildtype *Y. lipolytica's* inability to produce anything other than a 18:2 fatty acid suggests a need for a heterologus LPAAT gene.

Despite the identification and public disclosure of several genes coding for LPAAT from various bacteria, yeast and plants, few genes are available from those microorganisms that naturally produce long-chain PUFAs (e.g., *Mortierella, Pythium, Cyclotella, Nitzschia, Crypthecodinium* and *Thraustochytrium*, producing e.g., ARA, EPA and/or DHA). Although it is likely that many of these organisms possess genes encoding LPAATs that would be preferred for the incorporation of long-chain PUFAs (i.e., relative to a LPAAT that does not naturally interact with long-chain PUFAs), the only known disclosure providing genes encoding LPAATs from these types of organisms is that of WO 2004/087902. Thus, there is a need for the identification and isolation of a gene encoding LPAAT from an organism such as those suggested above, to permit its use in the production and accumulation of long-chain PUFAs in the storage lipid pools (i.e., TAG fraction) of transformant oleaginous yeast.

Surprisingly, the Applicants have isolated a novel gene from the filamentous fungus *Mortierella alpina* that is a LPAAT homolog. This gene is clearly differentiated from those *M. alpina* LPAAT sequences provided in the art. It is expected that the gene of the present invention ("LPAAT2") will be useful to enable one to modify the transfer of long-chain free fatty acids (e.g., ω-3 and/or ω-6 fatty acids) into the TAG pool in oleaginous yeast.

SUMMARY OF THE INVENTION

The invention relates to the discovery of a gene encoding a lysophosphatidic acid acyltransferase enzyme homolog from *Mortierella*. This gene and encoded enzyme are useful in manipulating the production of commercially useful oils in microorganisms, and particularly in oleaginous yeast. Accordingly the invention provides an isolated nucleic acid molecule encoding a lysophosphatidic acid acyltransferase enzyme homolog, selected from the group consisting of:

(a) an isolated nucleic acid molecule encoding the amino acid sequence as set forth in SEQ ID NO:2;

(b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or (c) an isolated nucleic acid molecule that is completely complementary to (a) or (b).

Similarly the invention provides a polypeptide encoded by the isolated nucleic acid molecule of the invention as well as genetic chimera-of these molecules and host cells comprising the same.

In one preferred embodiment the invention provides a method of increasing triacylglycerol content in a transformed host cell comprising:

(a) providing a transformed host cell comprising:
  (i) at least one gene encoding a lysophosphatidic acid acyltransferase enzyme homolog having the amino acid sequence as set forth in SEQ ID NO:2; and,
  (ii) a source of fatty acids;

(b) growing the cell of step (a) under conditions whereby the at least one gene encoding a lysophosphatidic acid acyltransferase enzyme homolog is expressed, resulting in the transfer of the fatty acids to triacylglycerol; and, (c) optionally recovering the triacylglycerol of step (b).

In an additional embodiment the invention provides a method of increasing the ω-3 or ω-6 fatty acid content of triacylglycerols in a transformed host cell comprising:

(a) providing a transformed host cell comprising:
  (i) at least one gene encoding at least one enzyme of the ω-3/ω-6 fatty acid biosynthetic pathway; and,
  (ii) at least one gene encoding a lysophosphatidic acid acyltransferase enzyme homolog having the amino acid sequence as set forth in SEQ ID NO:2;

(b) growing the cell of step (a) under conditions whereby the genes of (i) and (ii) are expressed, resulting in the production of at least one ω-3 or ω-6 fatty acid and its transfer to triacylglycerol; and, (c) optionally recovering the triacylglycerol of step (b).

Alternatively the invention provides a method of increasing triacylglycerol content in a transformed host cell comprising:

(a) providing a transformed host cell comprising:
  (i) at least one gene encoding a heterologous lysophosphatidic acid acyltransferase enzyme homolog having the amino acid sequence as set forth in SEQ ID NO:2; and,
  (ii) a source of fatty acids;
  wherein said transformed host has a disruption in the gene encoding the native lysophosphatidic acid acyltransferase enzyme;

(b) growing the cell of step (a) under conditions whereby the at least one gene encoding a lysophosphatidic acid acyltransferase enzyme homolog is expressed, resulting in the transfer of the fatty acids to triacylglycerol; and, (c) optionally recovering the triacylglycerol of step (b).

In similar fashion the method provides a method of increasing the ω-3 or ω-6 fatty acid content of triacylglycerols in a transformed host cell comprising:

(a) providing a transformed host cell comprising:
  (i) at least one gene encoding at least one enzyme of the ω-3/ω-6 fatty acid biosynthetic pathway; and,
  (ii) at least one gene encoding a lysophosphatidic acid acyltransferase enzyme homolog having the amino acid sequence as set forth in SEQ ID NO:2;
  wherein said transformed host has a disruption in the gene encoding the native lysophosphatidic acid acyltransferase enzyme;

(b) growing the cell of step (a) under conditions whereby the genes of (i) and (ii) are expressed, resulting in the production of at least one ω-3 or ω-6 fatty acid and its transfer to triacylglycerol; and, (c) optionally recovering the triacylglycerol of step (b).

BRIEF DESCRIPTION OF THE DRAWINGS AND SEQUENCE DESCRIPTIONS

FIG. 2 shows an alignment of lysophosphatidic acid acyltransferase (LPAAT) proteins and protein homologs from *Mortierella alpina*.

Figures 3D, 4A:
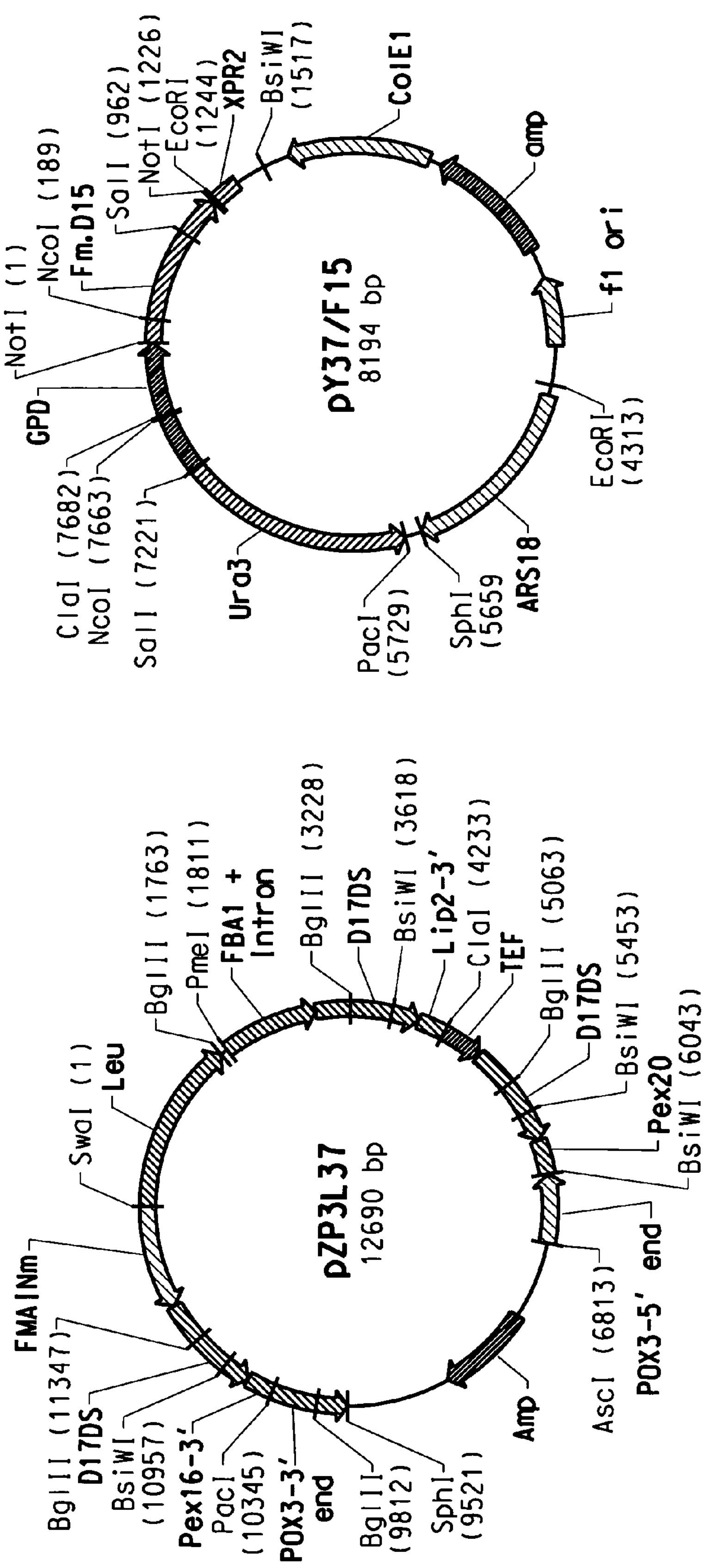

FIG. 3A diagrams the development of *Yarrowia lipolytica* strain Y2067U, producing up to 14% EPA in the total lipid fraction. FIG. 3B provides a plasmid map for pKUNF12T6E; FIG. 3C provides a plasmid map for pDMW232; and FIG. 3D provides a plasmid map for pZP3L37.

FIG. 4 provides plasmid maps for the following: (A) pY37/F15; (B) pKO2UF2PE; and (C) pZKUT16.

FIG. 5 provides plasmid maps for the following: (A) pZUF17; (B) pMLPAT-17; and (C) pZUF-Mod-1.

The invention can be more fully understood from the following detailed description and the accompanying sequence descriptions, which form a part of this application.

The following sequences comply with 37 C.F.R. § 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1–3, 8, 14–17, 19–22, 24, 25, 27, 28, 32, 33, 36, 37 and 45–48 are ORFs encoding genes or proteins (or portions thereof), as identified in Table 2.

TABLE 2

Summary of Gene and Protein SEQ ID Numbers

| Description and Abbreviation | Nucleic acid SEQ ID NO. | Protein SEQ ID NO. |
|---|---|---|
| *Mortierella alpina* lysophosphatidic acid acyltransferase homolog (LPAAT2)-complete cDNA | 1 (1086 bp) | 2 (308 AA) |
| *Mortierella alpina* LPAAT2 | 3 (927 bp) | — |
| *Mortierella alpina* LPAAT2 partial cDNA fragment | 8 (325 bp) | — |
| Synthetic elongase gene derived from *Mortierella alpina*, codon-optimized for expression in *Yarrowia lipolytica* | 14 (957 bp) | 15 (318 AA) |
| Synthetic Δ6 desaturase, derived from *Mortierella alpina*, codon-optimized for expression in *Yarrowia lipolytica* | 16 (1374 bp) | 17 (457 AA) |
| *Fusarium moniliforme* Δ12 desaturase | 19 (1434 bp) | 20 (477 AA) |
| Synthetic elongase gene derived from *Thraustochytrium aureum*, codon-optimized for expression in *Yarrowia lipolytica* | 21 (819 bp) | 22 (272 AA) |
| *Mortierella alpina* Δ5 desaturase | 24 (1341 bp) | 25 (446 AA) |
| Synthetic Δ17 desaturase gene derived from *Saprolegnia diclina*, codon-optimized for expression in *Yarrowia lipolytica* | 27 (1077 bp) | 28 (358 AA) |
| *Yarrowia lipolytica* Δ12 desaturase | 32 (1936 bp) | 33 (419 AA) |
| Synthetic $C_{16}$ elongase gene derived from *Rattus norvegicus*, codon-optimized for expression in *Yarrowia lipolytica* | 36 (804 bp) | 37 (267 AA) |
| *Yarrowia lipolytica* lysophosphatidic acid acyltransferase (LPAAT1) | 45 (849 bp) | 46 (282 AA) |
| *Yarrowia lipolytica* lysophosphatidic acid acyltransferase (LPAAT2) | 47 (672 bp) | 48 (223 AA) |

SEQ ID NOs:12, 23, 26, 30, 31, 35, 40, 41, 52 and 53 are plasmids as identified in Table 3.

TABLE 3

Summary of Plasmid SEQ ID Numbers

| Plasmid | Corresponding FIG. | SEQ ID NO |
|---|---|---|
| pKUNF12T6E | 3B | 12 (12,649 bp) |
| pDMW232 | 3C | 23 (10,945 bp) |
| pZP3L37 | 3D | 26 (12,690 bp) |
| pY37/F15 | 4A | 30 (8,194 bp) |
| pKO2UF2PE | 4B | 31 (10,838 bp) |
| pZKUT16 | 4C | 35 (5,833 bp) |
| pZUF17 | 5A | 40 (8,165 bp) |
| pMLPAT-17 | 5B | 41 (8,015 bp) |
| pMLPAT-Int | — | 52 (8,411 bp) |
| pZUF-MOD-1 | 5C | 53 (7,323 bp) |

SEQ ID NOs:4–6 correspond to BD-Clontech Creator Smart® cDNA library kit primers SMART IV oligonucleotide, CDSIII/3' PCR primer and 5'-PCR primer.

SEQ ID NO:7 corresponds to the M13 forward primer used for cDNA library sequencing.

SEQ ID NOs:9–11 correspond to primers MLPAT-RC-1, MLPAT-RC-2 and MLPAT-RC-3, respectively, used for 5'-end RACE.

SEQ ID NOs:13, 18, 29 and 34 correspond to the following *Yarrowia lipolytica* promoters, respectively: fructose-bisphosphate aldolase+intron (FBAIN; 973 bp); fructose-bisphosphate aldolase (FBA; 1001 bp); fructose-bisphosphate aldolase+modified intron (FBAINm; 924 bp); and, glycerol-3-phosphate acyltransferase (GPAT; 1130 bp).

SEQ ID NOs:38 and 39 correspond to primers MLPAT-F and MLPAT-R, respectively; SEQ ID NOs:42 and 43 correspond to primers LPAT-Re-5-1 and LPAT-Re-5-2, respectively; and SEQ ID NOs:49 and 50 correspond to primers LPAT-Re-3-1 and LPAT-Re-3-2, respectively. Each of these three primer sets was used for the construction of plasmids pMLPAT-17 and/or pMLPAT-Int.

SEQ ID NOs:44 and 51 correspond to a 5' (1129 bp) and 3' (938 bp) region of the *Y. lipolytica* LPAAT1 ORF, respectively.

SEQ ID NOs:54 and 55 correspond to primers pzuf-mod1 and pzuf-mod2, respectively, used for creating "control" plasmid pZUF-MOD-1.

DETAILED DESCRIPTION OF THE INVENTION

In accordance with the subject invention, Applicants have isolated a *Mortierella alpina* gene encoding a lysophosphatidic acid acyltransferase (LPAAT) enzyme homolog useful for transferring fatty acids into storage triacylglycerols (TAGs). This gene (identified herein as "LPAAT2") may be useful in altering the quantity of long-chain polyunsaturated fatty acids (PUFAs) produced in oleaginous yeast.

The importance of PUFAs are undisputed. For example, certain PUFAs are important biological components of healthy cells and are recognized as "essential" fatty acids that cannot be synthesized de novo in mammals and instead must be obtained either in the diet or derived by further desaturation and elongation of linoleic acid (LA) or α-linolenic acid (ALA). Additionally, a high intake of long-chain ω-3 PUFAs produces cardiovascular protective effects (Dyerberg, J. et al., *Amer. J. Clin Nutr.* 28:958–966 (1975); Dyerberg, J. et al., *Lancet* 2(8081):117–119 (Jul. 15, 1978); Shimokawa, H., *Wold Rev Nutr Diet,* 88:100–108 (2001); von Schacky, C., and Dyerberg, J., *World Rev Nutr Diet,* 88:90–99 (2001)). Numerous other studies document wide-ranging health benefits conferred by administration of ω-3 and/or ω-6 fatty acids against a variety of symptoms and diseases (e.g., asthma, psoriasis, eczema, diabetes, cancer).

As such, the subject invention finds many applications. PUFAs, or derivatives thereof, accumulated by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with ARA can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used.

The following definitions are provided.

"Open reading frame" is abbreviated ORF.

"Polymerase chain reaction" is abbreviated PCR.

"American Type Culture Collection" is abbreviated ATCC.

"Polyunsaturated fatty acid(s)" is abbreviated PUFA(s).

"Lysophosphatidic acid acyltransferase" is abbreviated LPAAT.

"Triacylglycerols" are abbreviated TAGs.

"Co-enzyme A" is abbreviated CoA.

The term "fatty acids" refers to long-chain aliphatic acids (alkanoic acids) of varying chain length, from about $C_{12}$ to $C_{22}$ (although both longer and shorter chain length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"PUFAs" can be classified into two major families (depending on the position (n) of the first double bond nearest the methyl end of the fatty acid carbon chain). Thus, the "omega-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "omega-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of the present disclosure, the omega-reference system will be used to indicate the number of carbons, the number of double bonds and the position of the double bond closest to the omega carbon, counting from the omega carbon (which is numbered 1 for this purpose). This nomenclature is shown below in Table 4, in the column titled "Shorthand Notation". The remainder of the Table summarizes the common names of ω-3 and ω-6 fatty acids, the abbreviations that will be used throughout the specification and each compounds' chemical name.

TABLE 4

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

"Microbial oils" or "single cell oils" are those oils naturally produced by microorganisms (e.g., algae, oleaginous yeast and filamentous fungi) during their lifespan. The term "oil" refers to a lipid substance that is liquid at 25° C. and usually polyunsaturated. In contrast, the term "fat" refers to a lipid substance that is solid at 25° C. and usually saturated.

"Lipid bodies" refer to lipid droplets that usually are bounded by specific proteins and a monolayer of phospholipid. These organelles are sites where most organisms transport/store neutral lipids. Lipid bodies are thought to arise from microdomains of the endoplasmic reticulum that contain TAG-biosynthesis enzymes; and, their synthesis and size appear to be controlled by specific protein components.

"Neutral lipids" refer to those lipids commonly found in cells in lipid bodies as storage fats and oils and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or TAG, respectively (or collectively, acylglycerols). A hydolysis reaction must occur to release free fatty acids from acylglycerols.

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long-chain PUFAs, as well as shorter saturated and unsaturated fatty acids and longer chain saturated fatty acids. Thus, "oil biosynthesis" generically refers to the synthesis of TAGs in the cell.

The term "LPAAT" refers to a lysophosphatidic acid acyltransferase enzyme (EC 2.3.1.51). This enzyme is responsible for the transfer of an acyl-CoA group onto 1-acyl-sn-glycerol 3-phosphate (lysophosphatidic acid) to produce CoA and 1,2-diacyl-snglycerol 3-phosphate (phosphatidic acid). The literature also refers to LPAAT as acyl-CoA:1-acyl-sn-glycerol-3-phosphate 2-O-acyltransferase, 1-acyl-sn-glycerol-3-phosphate acyltransferase and/or 1-acylglycerolphosphate acyltransferase (abbreviated as AGAT).

The term "LPAAT2", within the context of the *Mortierella alpina* sequence provided herein as SEQ ID NO:3, refers to a gene encoding a lysophosphatidic acid acyltransferase enzyme homolog. The LPAAT2 protein sequence is provided as SEQ ID NO:2.

Figure 1:
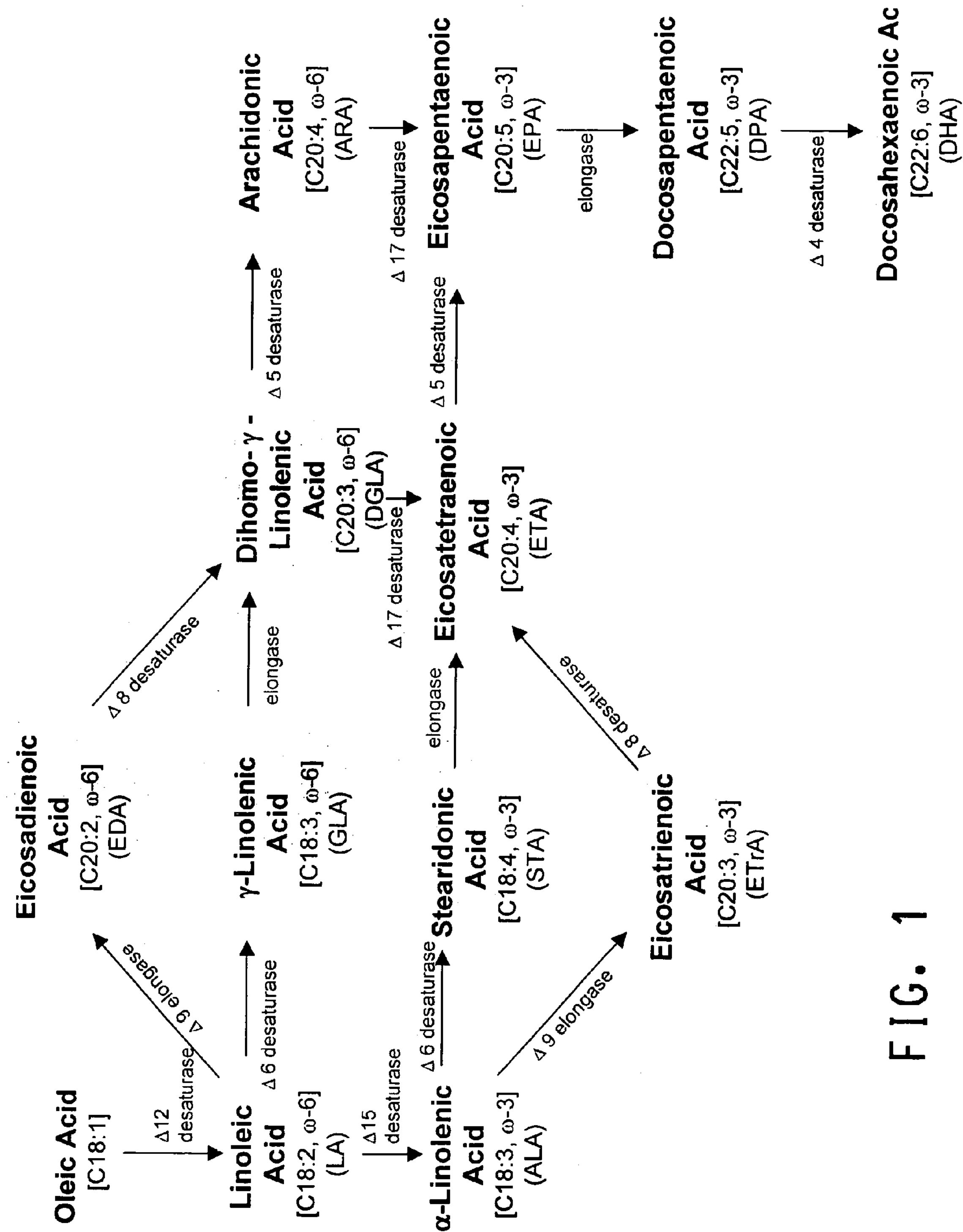
FIG. 1 illustrates the ω-3 and ω-6 fatty acid biosynthetic pathways.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode some or all of the following enzymes: Δ12 desaturase, Δ6 desaturase, elongase, Δ5 desaturase, Δ17 desaturase, Δ15 desaturase, Δ9 desaturase, Δ8 desaturase and Δ4 desaturase. A representative pathway is illustrated in FIG. 1, providing for the conversion of oleic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway, whereas that portion that generates only ω-6 fatty acids will be referred to herein as the ω-6 fatty acid biosynthetic pathway.

The term "functional" as used herein in context with the ω-3/ω-6 fatty acid biosynthetic pathway means that some (or all) of the genes in the pathway express active enzymes, resulting in in vivo catalysis or substrate conversion. It should be understood that "ω-3/ω-6 fatty acid biosynthetic pathway" or "functional ω-3/ω-6 fatty acid biosynthetic pathway" does not imply that all the genes listed in the above paragraph are required, as a number of fatty acid products will only require the expression of a subset of the genes of this pathway.

The term "desaturase" refers to a polypeptide that can desaturate, i.e., introduce a double bond, in one or more fatty acids to produce a mono- or polyunsaturated fatty acid. Despite use of the omega-reference system throughout the specification in reference to specific fatty acids, it is more convenient to indicate the activity of a desaturase by counting from the carboxyl end of the substrate using the delta-system. Of particular interest herein are: Δ12 desaturases that desaturate a fatty acid between the $12^{th}$ and $13^{th}$ carbon atoms numbered from the carboxyl-terminal end of the molecule and that catalyze the conversion of oleic acid to LA; Δ15 desaturases that catalyze the conversion of LA to ALA; Δ17 desaturases that catalyze the conversion of ARA to EPA and/or DGLA to ETA; Δ6 desaturases that catalyze the conversion of LA to GLA and/or ALA to STA; Δ5 desaturases that catalyze the conversion of DGLA to ARA and/or ETA to EPA; Δ4 desaturases that catalyze the conversion of DPA to DHA; Δ8 desaturases that catalyze the conversion of EDA to DGLA and/or ETrA to ETA; and Δ9 desaturases that catalyze the conversion of palmitate to palmitoleic acid (16:1) and/or stearate to oleic acid (18:1).

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, whereby CoA is the acyl carrier (Lassner et al., *The Plant Cell* 8:281–292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongases are the conversion of GLA to DGLA, STA to ETA, and EPA to DPA. In general, the substrate selectivity of elongases is somewhat broad but segregated by both chain length and the degree of unsaturation. Accordingly, elongases can have different specificities. For example, a $C_{16/18}$ elongase will prefer a $C_{16}$ substrate, a $C_{18/20}$ elongase will prefer a $C_{18}$ substrate and a $C_{20/22}$ elongase will prefer a $C_{20}$ substrate. In like manner, a Δ9 elongase is able to catalyze the conversion of LA and ALA to EDA and ETrA, respectively.

The term "oleaginous" refers to those organisms that tend to store their energy source in the form of lipid (Weete, In: Fungal Lipid Biochemistry, $2^{nd}$ Ed., Plenum, 1980). Generally, the cellular oil content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419–25 (1991)).

The term "oleaginous yeast" refers to those microorganisms classified as yeasts that can make oil. Generally, the cellular oil or triacylglycerol content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419–25 (1991)). It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces.*

The term "fermentable carbon substrate" means a carbon source that a microorganism will metabolize to derive energy. Typical carbon sources of the invention include, but are not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

As used herein, the terms "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS*. 5:151–153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403–410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111–20. Suhai, Sandor, Ed. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized", as it refers to genes or coding regions of nucleic acid molecules, refers to modification of codons such that the altered codons reflect the typical codon usage of the host organism without altering the polypeptide for which the DNA codes.

"Chemically synthesized", as related to a sequence of DNA, means that the component nucleotides-were assembled in vitro. Manual chemical synthesis of DNA may be accomplished using well-established procedures; or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene(s) and having elements in addition to the foreign gene(s) that facilitate transformation of a particular host cell. "Expression cassette" refers to a specific vector containing a foreign gene(s) and having elements in addition to the foreign gene(s) that allow for enhanced expression of that gene in a foreign host.

The term "homologous recombination" refers to the exchange of DNA fragments between two DNA molecules (during cross over). The fragments that are exchanged are flanked by sites of identical nucleotide sequences between the two DNA molecules (i.e., "regions of homology").

The term "regions of homology" refer to stretches of nucleotide sequence on nucleic acid fragments that participate in homologous recombination that have homology to each other. Effective homologous recombination will generally take place where these regions of homology are at least about 10 bp in length where at least about 50 bp in length is preferred. Typically fragments that are intended for recombination contain at least two regions of homology where targeted gene disruption or replacement is desired.

Standard recombinant DNA and molecular cloning techniques used herein are well known in the art and are described by Sambrook, J., Fritsch, E. F. and Maniatis, T., *Molecular Cloning: A Laboratory Manual,* $2^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Microbial Biosynthesis Of Fatty Acids and Triacylglycerols

The process of de novo synthesis of palmitate (16:0) in oleaginous microorganisms is described in WO 2004/101757 (published Nov. 25, 2004). This fatty acid is the precursor of longer-chain saturated and unsaturated fatty acid derivates, which are formed through the action of elongases and desaturases. For example, palmitate is converted to its unsaturated derivative [palmitoleic acid (16:1)] by the action of a Δ9 desaturase; similarly, palmitate is elongated to form stearic acid (18:0), which can be converted to its unsaturated derivative by a Δ9 desaturase to thereby yield oleic (18:1) acid.

TAGs (the primary storage unit for fatty acids) are formed by a series of reactions. First, one molecule of acyl-CoA is esterified to glycerol-3-phosphate via a GPAT acyltransferase to produce lysophosphatidic acid (LPA) (and CoA as a by-product). Secondly, LPAAT catalyzes a reaction whereby LPA is converted to 2-diacylglycerol phosphate (commonly identified as phosphatidic acid (PA)) (and CoA as a by-product) by the esterification of a second molecule of acyl-CoA. Third, phosphatidic acid phosphatase is responsible for the removal of a phosphate group from phosphatidic acid to yield 1,2-diacylglycerol (DAG). And finally, a third fatty acid is added to the sn-3 position of DAG by a DAG acyltransferase (e.g., PDAT, DGAT1 or DGAT2) to form TAG.

A wide spectrum of fatty acids can be incorporated into TAGs, including saturated and unsaturated fatty acids and short-chain and long-chain fatty acids. Some non-limiting examples of fatty acids that can be incorporated into TAGs by acyltransferases (e.g., DGAT2) include: capric (10:0), lauric (12:0), myristic (14:0), palmitic (16:0), palmitoleic (16:1), stearic (18:0), oleic (18:1), vaccenic (18:1), LA (18:2), eleostearic (18:3), GLA (18:3), ALA (18:3), STA (18:4), arachidic (20:0), EDA (20:2), DGLA (20:3), ETrA (20:3), ARA (20:4), ETA (20:4), EPA (20:5), behenic (22:0), DPA (22:5), DHA (22:6), lignoceric (24:0), nervonic (24:1), cerotic (26:0), and montanic (28:0) fatty acids. In preferred embodiments of the present invention, incorporation of PUFAs into TAG is most desirable.

Genes Encoding LPAAT

Many genes encoding LPAAT enzymes have been identified through genetic means and the DNA sequences of some of these genes are publicly available. For example, some non-limiting examples include the following GenBank Accession Numbers: Q93841 and Q22267 (*Caenorhabditis elegans*); Q99943, 015120, Q9NRZ7, Q9NRZ5, Q9NUQ2 (*Homo sapiens*); 035083 and Q9D1E8 (*Mus musculus*); Q924S1 (*Rattus norvegicus*); Q59188 (*Borrelia burgdorferi*); Q42670 (*Cocos nucifera*); P26647 (*Escherichia coli*); P44848 (*Haemophilus influenzae*); Q9ZJN8 and 025903 (*Helicobacter pylori*); Q42868 (*Limnanthes alba*); Q42870 (*Limnanthes douglasii*); P26974 (*Salmonella typhimurium*); P33333 (*Saccharomyces cerevisiae*); and Q9XFW4 (*Brassica napus*). Additionally, the patent literature provides many additional DNA sequences of LPAAT genes (and/or details concerning several of the genes above and their methods of isolation); see, for example: EP1144649, EP1131438, U.S. Pat. No. 5,968,791, U.S. Pat. No. 6,093,568, WO 00/049156 and WO 04/087902. The work of Renz et al. (WO 04/087902) includes DNA sequences of LPAATs from, e.g., *Mortierella alpina* (GenBank Accession Nos. CQ891252, CQ891250), *Physcomitrella patens* (GenBank Accession Nos. CQ891260, CQ891258, CQ891248, CQ891245, CQ891241, CQ891238), *Shewanella hanedai*

(GenBank Accession No. CQ891254) and *Thraustochytrium* (GenBank Accession No. CQ891235).

Most recently, two putative LPAAT enzymes from the oleaginous yeast *Yarrowia lipolytica* have been identified, based on BLAST (Basic Local Alignment Search Tool; Altschul, S. F., et al., *J. Mol. Biol.* 215:403–410 (1993)) searches of the GenBank database. Specifically, a gene from *Y. lipolytica* designated herein as "LPAAT1" (SEQ ID NOs: 45 and 46) corresponds to GenBank Accession No. CR382131, locus tag "YALI0E18964g", annotated therein as an "unnamed protein product; similar to sp|P33333 *Saccharomyces cerevisiae* YDL052c SLC1 fatty acyltransferase [i.e., LPAAT, E.C. 2.3.1.51], start by similarity". In contrast, a gene from *Y. lipolytica* designated herein as "LPAAT2" (SEQ ID NOs:47 and 48) corresponds to GenBank Accession No. CR382128, locus tag "YALI0B12254g", annotated therein as a "hypothetical protein" "weakly similar to DEHA0D18832g *Debaryomyces hansenii* IPF 2772.1, hypothetical start". Studies are underway to confirm both genes' activities.

Biosynthesis of Omega-3 and Omega-6 Polyunsaturated Fatty Acids

The metabolic process that converts LA to GLA, DGLA and ARA (the ω-6 pathway) and ALA to STA, ETA, EPA, DPA and DHA (the ω-3 pathway) involves elongation of the carbon chain through the addition of two-carbon units and desaturation of the molecule through the addition of double bonds (FIG. 1). This requires a series of desaturation and elongation enzymes. Specifically, oleic acid is converted to LA (18:2), the first of the ω-6 fatty acids, by the action of a Δ12 desaturase. Subsequent ω-6 fatty acids are produced as follows: 1.) LA is converted to GLA by the activity of a Δ6 desaturase; 2.) GLA is converted to DGLA by the action of an elongase; and 3.) DGLA is converted to ARA by the action of a Δ5 desaturase. In like manner, linoleic acid (LA) is converted to ALA, the first of the ω-3 fatty acids, by the action of a Δ15 desaturase. Subsequent ω-3 fatty acids are produced in a series of steps similar to that for the ω-6 fatty acids. Specifically, 1.) ALA is converted to STA by the activity of a Δ6 desaturase; 2.) STA is converted to ETA by the activity of an elongase; and 3.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

In alternate embodiments, a Δ9 elongase is able to catalyze the conversion of LA and ALA to eicosadienoic acid (EDA; C20:2) and eicosatrienoic acid (ETrA; C20:3), respectively. A Δ8 desaturase then converts these products to DGLA and ETA, respectively.

Many microorganisms, including algae, bacteria, molds, fungi and yeast can synthesize PUFAs and omega fatty acids in the ordinary course of cellular metabolism. Alternatively, if the host organism of choice does not natively produce the desired PUFAs (or possess the desired lipid profile), one skilled in the art will be familiar with the considerations and techniques necessary to introduce an expression cassette encoding appropriate enzymes for PUFA biosynthesis into the host organism of choice. For these purposes, a variety of desaturase and elongase genes involved in PUFA production have been identified through genetic means and the DNA sequences of some of these genes are publicly available (e.g., see WO 04/101757 [herein incorporated by reference in its entirety] for a review of available genes in GenBank and/or the patent literature and considerations for choosing a specific polypeptide having desaturase or elongase activity). And, although not elaborated in detail herein, numerous teachings are provided in the literature wherein various organisms are engineered to produce specific PUFAs; some illustrative references are provided as follows, although these should not be construed as limiting: WO 98/46763; WO 98/46764; WO 98/46765; WO 99/64616; WO 02/077213; WO 03/093482; WO 04/057001; WO 04/090123; WO 04/087902; WO 04/101757; U.S. Pat. No. 6,140,486; U.S. Pat. No. 6,459,018; U.S. Pat. No. 6,136,574; U.S. 03/0172399; U.S. 04/0172682; U.S. 04/098762; U.S. 04/0111763; U.S. 04/0053379; U.S. 04/0049805; U.S. 04/0237139; U.S. 04/0172682; Beaudoin F. et al., *PNAS* USA, 97(12):6421–6426 (2000); Dyer, J. M. et al., *Appl. Envi. Microbiol.,* 59:224–230 (2002); Domergue, F. et al. *Eur. J. Biochem.* 269:4105–4113 (2002); Qi, B. et al., *Nature Biotech.* 22:739–745 (2004); and Abbadi et al., *The Plant Cell,* 16:2734–2748 (2004)).

Briefly, however, a variety of ω-3/ω-6 PUFA products can be produced (prior to their transfer to TAGs), depending on the fatty acid substrate and the particular genes of the ω-3/ω-6 fatty acid biosynthetic pathway that are present in (or transformed into) the host cell. As such, production of the desired fatty acid product can occur directly (wherein the fatty acid substrate is converted directly into the desired fatty acid product without any intermediate steps or pathway intermediates) or indirectly (wherein multiple genes encoding the ω-3/ω-6 biosynthetic pathway may be used in combination, such that a series of reactions occur to produce a desired PUFA). Specifically, for example, it may be desirable to transform an oleaginous yeast with an expression cassette comprising a Δ6 desaturase, an elongase, a Δ5 desaturase and a Δ17 desaturase for the overproduction of EPA. As is well known to one skilled in the art, various other combinations of the following enzymatic activities may be useful to express in an oleaginous organism: a Δ15 desaturase, a Δ4 desaturase, a Δ5 desaturase, a Δ6 desaturase, Δ12 desaturase, a Δ9 desaturase, a Δ8 desaturase, a Δ12 desaturase and/or an elongase(s) (see FIG. 1). The particular genes included within a particular expression cassette will depend on the oleaginous organism (and its PUFA profile and/or desaturase/elongase profile), the availability of substrate and the desired end product(s).

Sequence Identification Of *Mortierella Alpina* LPAAT2

Although the native *Yarrowia lipolytica* genes encoding LPAAT have been identified (supra, SEQ ID NOs:45 and 47 herein), neither is expected to favor longer chain PUFAs (i.e., those PUFAs having a chain length equal to or greater than $C_{20}$). Thus, in the present invention, a gene encoding a LPAAT homolog (designated herein as "LPAAT2") has been isolated from *Mortierella alpina. M. alpina* is an organism that naturally accumulates fatty acids having chain lengths equal to or greater than $C_{20}$ in its TAG fraction, thus indicating that the LPAAT2 is likely to have the desired substrate specificity.

Comparison of the LPAAT2 nucleotide base and deduced amino acid sequences to public databases, using a BLAST algorithm (Altschul, S. F., et al., *Nucleic Acids Res.* 25:3389–3402 (1997)), reveals that the most similar known sequences are about 33% identical to the amino acid sequence of LPAAT2 reported herein over a length of 308 amino acids. Preferred amino acid fragments are at least about 70%–80% identical to the sequences herein, where those sequences that are 85%–90% identical are particularly suitable and those sequences that are about 95% identical are most preferred. Similarly, preferred LPAAT2 encoding nucleic acid sequences corresponding to the instant ORF are those encoding active proteins and which are at least about 70%–80% identical to the nucleic acid sequences encoding LPAAT2 reported herein, where those sequences that are 85%–90% identical are particularly suitable and those sequences that are about 95% identical are most preferred.

Isolation Of Homologs

LPAAT2 nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci.* USA 82:1074 (1985); or strand displacement amplification (SDA), Walker, et al., *Proc. Natl. Acad. Sci*. U.S.A., 89:392 (1992)]; and 3.) methods of library construction and screening by complementation.

For example, genes encoding similar proteins or polypeptides to the LPAAT2 described herein could be isolated directly by using all or a portion of the instant nucleic acid fragments as DNA hybridization probes to screen libraries from any desired yeast or fungus using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33–50, IRL: Herndon, Va.; and Rychlik, W., In *Methods in Molecular Biology*, White, B. A. Ed., (1993) Vol. 15, pp 31–39, PCR Protocols: Current Methods and Applications. Humania: Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS* USA 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL, Gaithersburg, Md.), specific 3' or 5' cDNA fragments can be isolated (Ohara et al., *PNAS* USA 86:5673 (1989); Loh et al., *Science* 243:217 (1989)).

Alternatively, the instant LPAAT2 sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers (e.g., sodium citrate, Tris-HCl, PIPES or HEPES (pH range about 6–9)), about 0.05 to 0.2% detergent (e.g., sodium dodecylsulfate), or between 0.5–20 mM EDTA, FICOLL (Pharmacia Inc.) (about 300–500 kdal), polyvinylpyrrolidone (about 250–500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening of DNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can then be used to screen DNA expression libraries to isolate full-length DNA clones of interest (Lerner, R. A. *Adv. Immunol.* 36:1 (1984); Maniatis, supra).

Gene Optimization for Improved Heterologous Expression

It may be desirable to modify the expression of the instant LPAAT2 and/or ω-3/ω-6 biosynthetic pathway enzymes to achieve optimal conversion efficiency of each, according to the specific TAG composition of interest. As such, a variety of techniques can be utilized to improve/optimize the expression of a polypeptide of interest in an alternative host. Two such techniques include codon-optimization and mutagenesis of the gene.

Codon Optimization

As will be appreciated by one skilled in the art, it is frequently useful to modify a portion of the codons encoding a particular polypeptide that is to be expressed in a foreign host, such that the modified polypeptide uses codons that are preferred by the alternate host. Use of host-preferred codons can substantially enhance the expression of the foreign gene encoding the polypeptide.

In general, host-preferred codons can be determined within a particular host species of interest by examining codon usage in proteins (preferably those expressed in the largest amount) and determining which codons are used with highest frequency. Thus, the coding sequence for a specific polypeptide of interest can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

Thus, for example, it may be desirable to modify a portion of the codons encoding the LPAAT2 polypeptide, to enhance the expression of the gene in *Yarrowia lipolytica*. The codon usage profile and the consensus sequence around the 'ATG' translation initiation codon for this particular organism are taught in co-pending U.S. patent application Ser. No. 10/840,478 (herein incorporated entirely by reference); likewise, a method for rapid synthesis of genes optimized for expression in *Y. lipolytica* is also provided.

Mutagenesis

Methods for synthesizing sequences and bringing sequences together are well established in the literature. For example, in vitro mutagenesis and selection, site-directed mutagenesis, error prone PCR (Melnikov et al., *Nucleic Acids Research,* 27(4):1056–1062 (Feb. 15, 1999)), "gene shuffling" or other means can be employed to obtain mutations of naturally occurring LPAAT2 genes. This would permit production of an LPAAT2 polypeptide having activity in vivo with more desirable physical and kinetic parameters for function in the host cell (e.g., a longer half-life or a higher rate of synthesis of TAGs from fatty acids).

If desired, the regions of a LPAAT2 polypeptide important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a LPAAT2 polypeptide important for activity. A mutated construct is expressed, and the ability of the resulting altered protein to function as desired is assayed. Such structure-function analysis can determine which regions may be deleted, which regions tolerate insertions, and which point mutations allow the mutant protein to function in substantially the same way as the native LPAAT2.

All such mutant proteins and nucleotide sequences encoding them that are derived from the LPAAT2 described herein are within the scope of the present invention.

Metabolic Engineering to Up-Regulate Genes and Biosynthetic Pathways Affecting Fatty Acid Synthesis and Oil Accumulation in Oleaginous Yeast Methods useful for manipulating biochemical pathways are well known to those skilled in the art. It is expected that introduction of chimeric genes encoding the LPAAT2 described herein, under the control of the appropriate promoters, will result in increased transfer of fatty acids to storage TAGs. As such, the present invention encompasses a method for increasing the TAG content in an oleaginous yeast comprising expressing the LPAAT2 enzyme of the present invention in a transformed oleaginous yeast host cell producing a fatty acid, such that the fatty acid is transferred to the TAG pool.

Additional copies of LPAAT2 genes may be introduced into the host to increase the transfer of fatty acids to the TAG fraction. Expression of the genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of heterologous genes is to increase the translational efficiency of the encoded mRNAs by replacement of codons in the native gene with those for optimal gene expression in the selected host.

In one specific embodiment, the present invention encompasses a method of increasing the ω-3 and/or ω-6 fatty acid content of TAGs in an oleaginous yeast, since it is possible to introduce an expression cassette encoding each of the enzymes necessary for ω-3 and/or ω-6 fatty acid biosynthesis into the organism (since naturally produced PUFAs in these organisms are limited to 18:2 (i.e., LA), and less commonly 18:3 (i.e., ALA) fatty acids). Thus, the method comprises:

- a) providing a transformed oleaginous yeast host cell possessing at least one gene encoding at least one enzyme of the ω-3/ω-6 fatty acid biosynthetic pathway and the LPAAT2 enzyme of the present invention;
- b) growing the yeast cells of step (a) in the presence of a fermentable carbon substrate, whereby the gene(s) of the ω-3/ω-6 fatty acid biosynthetic pathway and LPAAT2 are expressed, whereby a ω-3 and/or ω-6 fatty acid is produced, and whereby the ω-3 and/or ω-6 fatty acid is transferred to TAGs.

Within the context of the present invention, it may be useful to modulate the expression of the TAG biosynthetic pathway by any one of the methods described above. For example, the present invention provides a gene encoding a key enzyme in the fatty acid biosynthetic pathway leading to the storage of TAGs. This gene encodes the LPAAT2 enzyme. It will be particularly useful to express this gene in oleaginous yeast to maximize production and accumulation of TAGs using various means for metabolic engineering of the host organism. In preferred embodiments, modification of the expression levels of this gene in combination with expression of ω-3/ω-6 biosynthetic genes can be utilized to maximize production and accumulation of preferred PUFAs in the TAG pool.

Metabolic Engineering to Down-Regulate Undesirable Genes and Biosynthetic Pathways Affecting Fatty Acid Synthesis and Oil Accumulation in Oleaginous Yeast In some embodiments, it may be useful to disrupt or inactivate a host organism's native LPAAT, based on the complete sequences described herein, the complement of those complete sequences, substantial portions of those sequences, codon-optimized acyltransferases derived therefrom, and those sequences that are substantially homologous thereto. In an alternate embodiment, a transformant host organism comprising a disruption or inactivation of its native LPAAT may then be advantageously transformed to express a heterologous LPAAT2 (e.g., if the heterologous LPAAT2 has different substrate specificity than the native LPAAT).

For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al., *J. Bacteriol.* 171:4617–4622 (1989); Balbas et al., *Gene* 136:211–213 (1993); Gueldener et al., *Nucleic Acids Res.* 24:2519–2524 (1996); and Smith et al., *Methods Mol. Cell. Biol.* 5:270–277(1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology, 2$^{nd}$* ed. (1989) Sinauer Associates: Sunderland, Mass.; or Deshpande, Mukund V., *Appl. Biochem. Biotechnol.,* 36:227 (1992).

Another non-specific method of gene disruption is the use of transposable elements or transposons. Transposons are genetic elements that insert randomly into DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available [see, for example:

1.) The Primer Island Transposition Kit, available from Perkin Elmer Applied Biosystems, Branchburg, N.J., based upon the yeast Tyl element;
2.) The Genome Priming System, available from New England Biolabs, Beverly, Mass., based upon the bacterial transposon Tn7; and 3.) the EZ::TN Transposon Insertion Systems, available from Epicentre Technologies, Madison, Wis., based upon the Tn5 bacterial transposable element].

As described in U.S. Patent Application No. 60/624,812, the Applicants have discovered that expression of heterologous acyltransferases in conjunction with knockouts of the corresponding native *Yarrowia lipolytica* acyltransferase can significantly increase the overall long-chain ω-3 PUFAs that are produced in transformant *Y. lipolytica* host cells engineered for PUFA biosynthesis. This manipulation is thought to reduce substrate competition between the native and heterologous acyltransferase; and, when the heterologous acyltransferase has specificity for those fatty acids that are 18:3 and greater (in comparison to the native enzymes that may not efficiently catalyze reactions with longer chain fatty acids since naturally produced PUFAs in *Y. lipolytica are limited to* 18:2 fatty acids), more efficient acyltransferase reactions are likely enabled within the transformant host. Thus, within the context of the present invention, it may be useful to disrupt or inactivate a host organism's native LPAAT (e.g., the *Y. lipolytica* LPAAT1 or LPAAT2 (SEQ ID NOs:45 and 47, respectively)) that does not have specificity for long-chain PUFAs (e.g., 20:0, 22:0) or that has difficulty efficiently synthesizing TAGs comprising fatty acids that are 18:3 and greater in length (e.g., EPA). Then, the heterologous (or "foreign") LPAAT2 of the present invention (i.e. SEQ ID NO:2) could be expressed to enable increased accumulation of long-chain PUFAs in the organism's TAG fraction, since substrate competition between the native and heterologous acyltransferase would be reduced. One skilled in the art would readily be able to apply the teachings herein toward the advantageous manipulation of LPAAT enzymes and homologs (e.g., LPAAT2) in other oleaginous organisms.

In conjunction with this approach, or alternatively, it may be necessary to disrupt genes and pathways that diminish the existing fatty acid pool and/or that hydrolyze TAGs to regulate (and/or maximize) TAG accumulation.

Expression Systems, Cassettes And Vectors

The gene and gene product of the instant sequences described herein may be produced in microbial host cells, particularly in the cells of oleaginous yeast (e.g., *Yarrowia lipolytica*). Expression in recombinant microbial hosts may be useful for the transfer of various fatty acids to TAGs.

Microbial expression systems and expression vectors containing regulatory sequences that direct high level expression of foreign proteins are well known to those skilled in the art. Any of these could be used to construct chimeric genes for production of the gene products of the instant LPAAT2 sequences. These chimeric genes could then be introduced into appropriate microorganisms via transformation to provide high level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions or promoters which are useful to drive expression of the instant ORF in the desired host cell are numerous and familiar to those skilled in the art. Virtually any promoter capable of directing expression of this gene in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (see U.S. patent application Ser. No. 10/869,630), phosphoglycerate mutase (see U.S. patent application Ser. No. 10/869,630), fructose-bisphosphate aldolase (see U.S. patent application Ser. No. 10/987,548), phosphoglucose-isomerase, phosphoglycerate kinase, glycerol-3-phosphate O-acyltransferase (see U.S. Patent Application No. 60/610,060), etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest (see, e.g., U.S. patent application Ser. No. 10/840,478 for specific teachings applicable for *Yarrowia lipolytica*).

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of the LPAAT2 enzyme described herein.

Preferred Microbial Hosts for Recombinant Expression of LPAAT2

Host cells for expression of the instant LPAAT2 gene and nucleic acid fragments may include microbial hosts that grow on a variety of feedstocks, including simple or complex carbohydrates, organic acids and alcohols and/or hydrocarbons over a wide range of temperature and pH values. Although the gene described in the instant invention has been isolated for expression in an oleaginous yeast, and in particular *Yarrowia lipolytica*, it is contemplated that because transcription, translation and the protein biosynthetic apparatus is highly conserved, any bacteria, yeast, algae and/or filamentous fungus will be a suitable host for expression of the present nucleic acid fragments.

Preferred microbial hosts are oleaginous organisms, such as oleaginous yeast. These oleaginous organisms are naturally capable of oil synthesis and accumulation, wherein the total oil content can comprise greater than about 25% of the cellular dry weight, more preferably greater than about 30% of the cellular dry weight and most preferably greater than about 40% of the cellular dry weight. Additionally, there is basis for the use of these organisms for the production of PUFAs, as seen in co-pending U.S. patent applications Ser. No. 10/840,579 and No. 60/624,812, each incorporated entirely by reference herein.

Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982, ATCC #90812 and/or LGAM S(7)1 (Papanikolaou S., and Aggelis G., *Bioresour. Technol.* 82(1):43–9 (2002)).

Transformation Of Microbial Hosts

Once the DNA encoding a polypeptide suitable for expression in an oleaginous yeast has been obtained, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology,* 194:186–187 (1991)]), protoplast fusion, biolistic impact, electroporation, microinjection, or any other method that introduces the gene of interest into the host cell. More specific teachings applicable for oleaginous yeast (i.e., *Yarrowia lipolytica*) include U.S. Pat. Nos. 4,880,741 and 5,071,764 and Chen, D. C. et al. (*Appl Microbiol Biotechnol.* 48(2):232–235-(1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Desirably, resistance to kanamycin, hygromycin and the amino glycoside G418 are of interest, as well as ability to grow on media lacking uracil or leucine.

Following transformation, substrates suitable for the gene products of the instant sequence (and optionally other PUFA enzymes that are expressed within the host cell), may be produced by the host either naturally or transgenically, or they may be provided exogenously.

Fermentation Processes for Triacylglycerol Biosynthesis and Accumulation

The transformed microbial host cell is grown under conditions that optimize activity of fatty acid biosynthetic genes, acyltransferase genes and the LPAAT2 of the invention herein. This leads to production of the greatest and the most economical yield of fatty acids, which can in turn be transferred to TAGs for storage. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon substrate may include one-carbon substrates (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing substrates and will only be limited by the choice of the host organism. Although all of the above mentioned carbon substrates and mixtures thereof are expected to be suitable in the present invention, preferred carbon substrates are sugars and/or fatty acids. Most preferred is glucose and/or fatty acids containing between 10–22 carbons.

Nitrogen may be supplied from an inorganic (e.g., $(NH_4)_2SO_4$) or organic (e.g., urea, glutamate) source. In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for fatty acid production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61–97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of fatty acids and TAGs in oleaginous yeast cells requires a two-stage process, since the metabolic state must be "balanced" between growth and synthesis/storage of fats. Thus, most preferably, a two-stage fermentation process is necessary for the production of oils in oleaginous yeast. This approach is described in WO 2004/101757, as are various suitable fermentation process designs (i.e., batch, fed-batch and continuous) and considerations during growth.

Purification Of Fatty Acids

Fatty acids, including PUFAs, may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463–491 (1992)). A brief review of downstream processing is also available by A. Singh and O. Ward (*Adv. Appl. Microbiol.* 45:271–312 (1997)).

In general, means for the purification of fatty acids (including PUFAS) may include extraction with organic solvents, sonication, supercritical fluid extraction (e.g., using carbon dioxide), saponification and physical means such as presses, or combinations thereof. One is referred to the teachings of WO 2004/101757 (published Nov. 25, 2004) for additional details.

DESCRIPTION OF PREFERRED EMBODIMENTS

The Applicants' ultimate goal is the development of an oleaginous yeast that accumulates TAGs enriched in ω-3 and/or ω-6 PUFAs. In support of this goal, acyltransferases must be identified that function efficiently in oleaginous yeast to enable synthesis and high accumulation of preferred TAGs in these hosts. Specifically, modification of the expression levels of these acyltransferases will enable increased transfer of fatty acids (and particularly, PUFAs having chain lengths equal to or greater than $C_{20}$) to TAGs. Thus, identification of efficient acyltransferases is necessary for the manipulation of the amount of ω-3/ω-6 PUFAs incorporated into the TAG fraction produced in transformant host cells.

In the present invention, Applicants have isolated and cloned a gene (i.e., "LPAAT2") from *Mortierella alpina* that encodes a LPAAT homolog. Based on the ability of the native organism to synthesize ARA at concentrations greater than 50% of the total fatty acids (TFAs), it was expected that LPAAT2 would have excellent efficiency synthesizing TAGs comprising long-chain fatty acids. Furthermore, the Applicants hypothesized that the *M. alpina* LPAAT2 would be useful for expression in various microbial hosts, and particularly for over-expression in oleaginous yeast whose native LPAAT may not have the substrate specificity necessary to enable efficient incorporation of PUFAs having chain lengths equal to or greater than $C_{20}$ into the TAG fraction. To test this, the *M. alpina* LPAAT2 was over-expressed in an engineered strain of *Yarrowia lipolytica* producing about 14% EPA. Transformant strains possessed increased oil content (total fatty acids as a % of dry cell weight) relative to the parental strains. Additional benefits may result, since expression of the LPAAT2 of the instant invention may also be placed under the control of strong constitutive or regulated promoters that do not have the regulatory constraints of the native gene.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

*E. coli* TOP10 cells were obtained from Invitrogen (Carlsbad, Calif.). *E. coli* (XL1-Blue) competent cells were purchased from the Stratagene Company (San Diego, Calif.). *E. coli* strains were typically grown at 37° C. on Luria Bertani (LB) plates.

General molecular cloning was performed according to standard methods (Sambrook et al., supra). Oligonucleotides were synthesized by Sigma-Genosys (Spring, Tex.). PCR products were cloned into Promega's pGEM-T-easy vector (Madison, Wis.).

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR, Inc., (Madison, Wis.).

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia Lipolytica*

*Y. lipolytica* strains ATCC #20362, #76982 and #90812 were purchased from the American Type Culture Collection (Rockville, Md.). *Y. lipolytica* strains were usually grown at 28° C. on YPD agar (1% yeast extract, 2% bactopeptone, 2% glucose, 2% agar).

Transformation of *Y. lipolytica* was performed according to the method of Chen, D. C. et al. (*Appl. Microbiol Biotechnol.* 48(2):232–235 (1997)), unless otherwise noted. Briefly, *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μl of resuspended cells, and maintained at 39° C. for 1 hr with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (DIFCO Laboratories, Detroit, Mich.) without ammonium sulfate or amino acids, 2% glucose, 0.1% proline, pH 6.1). Supplements of leucine and/or uracil were added as appropriate to a final concentration of 0.01% (thereby producing "MMLe" and "MMU" selection media, each prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (DIFCO Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Finally, for the "two-stage growth conditions" designed to promote conditions of oleaginy, High Glucose Media ("HGM") was prepared as follows: 14 g/L $KH_2PO_4$, 4 g/L $K_2HPO_4$, 2 g/L $MgSO_4.7H_2O$, 80 g/L glucose (pH 6.5).

Fatty Acid Analysis of *Yarrowia Lipolytica*

For fatty acid analysis, cells were collected by centrifugation and lipids were extracted as described in Bligh, E. G. & Dyer, W. J. (*Can. J. Biochem. Physiol.* 37:911–917 (1959)). Fatty acid methyl esters were prepared by transesterification of the lipid extract with sodium methoxide (Roughan, G., and Nishida I. *Arch Biochem Biophys.* 276 (1):38–46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5–10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

Example 1

Construction of a *Mortierella Alpina* cDNA Library

The present Example describes the construction of a cDNA library of *Mortierella alpina* using the BD-Clontech Creator Smart® cDNA library kit (Mississauga, ON, Canada), according to the manufacturer's protocol.

Specifically, *M. alpina* strain ATCC #16266 was grown in 60 mL YPD medium (2% Bacto-yeast extract, 3% Bactor-peptone, 2% glucose) for 3 days at 23° C. Cells were pelleted by centrifugation at 3750 rpm in a Beckman GH3.8 rotor for 10 min and resuspended in 6×0.6 mL Trizole reagent (Invitrogen). Resuspended cells were transferred to six 2 mL screw cap tubes each containing 0.6 mL of 0.5 mm glass beads. The cells were homogenized at the HOMOGENIZE setting on a Biospec (Bartlesville, Okla.) mini bead beater for 2 min. The tubes were briefly spun to settle the beads. Liquid was transferred to 4 fresh 1.5 mL microfuge tubes and 0.2 mL chloroform/isoamyl alcohol (24:1) was added to each tube. The tubes were shaken by hand for 1 min and let stand for 3 min. The tubes were then spun at 14,000 rpm for 10 min at 4° C. The upper layer was transferred to 4 new tubes. Isopropyl alcohol (0.5 mL) was added to each tube. Tubes were incubated at room temperature for 15 min, followed by centrifugation at 14,000 rpm and 4° C. for 10 min. The pellets were washed with 1 mL each of 75% ethanol, made with RNase-free water and air-dried. The total RNA sample was then redissolved in 500 μl of water, and the amount of RNA was measured by A260 nm using 1:50 diluted RNA sample. A total of 3.14 mg RNA was obtained.

This total RNA sample was further purified with the Qiagen RNeasy total RNA Midi kit following the manufacturer's protocol. Thus, the total RNA sample was diluted to 2 mL and mixed with 8 mL of buffer RLT with 80 μl of β-mercaptoethanol and 5.6 mL 100% ethanol. The sample was divided into 4 portions and loaded onto 4 RNeasy midid columns. The columns were then centrifuged for 5 min at 4500×g. To wash the columns, 2 mL of buffer RPE was loaded and the columns centrifuged for 2 min at 4500×g. The washing step was repeated once, except that the centrifugation time was extended to 5 min. Total RNA was eluted by applying 250 μl of RNase-free water to each column, waiting for 1 min and centrifuging at 4500×g for 3 min.

PolyA(+)RNA was then isolated from the above total RNA sample, following Pharmacia's kit protocol. Briefly, 2 oligo-dT-cellulose columns were used. The columns were washed twice with 1 mL each of high salt buffer. The total RNA sample from the previous step was diluted to 2 mL total volume and adjusted to 10 mM Tris/HCl, pH 8.0, 1 mM EDTA. The sample was heated at 65° C. for 5 min, then placed on ice. Sample buffer (0.4 mL) was added and the sample was then loaded onto the two oligo-dT-cellulose columns under gravity feed. The columns were centrifuged at 350×g for 2 min, washed 2× with 0.25 mL each of high salt buffer, each time followed by centrifugation at 350×g for 2 min. The columns were further washed 3 times with low salt buffer, following the same centrifugation routine. Poly (A)+RNA was eluted by washing the column 4 times with 0.25 mL each of elution buffer preheated to 65° C., followed by the same centrifugation procedure. The entire purification process was repeated once. Purified poly(A)+RNA was obtained with a concentration of 30.4 ng/μl.

cDNA was generated, using the LD-PCR method specified by BD-Clontech and 0.1 μg of polyA(+) RNA sample. Specifically, for 1$^{st}$ strand cDNA synthesis, 3 μl of the poly(A)+RNA sample was mixed with 1 μl of SMART IV oligo nucleotide (SEQ ID NO:4) and 1 μl of CDSIII/3' PCR primer (SEQ ID NO:5). The mixture was heated at 72° C. for 2 min and cooled on ice for 2 min. To the tube was added the following: 2 μl first strand buffer, 1 μl 20 mM DTT, 1 μl 10 mM dNTP mix and 1 μl Powerscript reverse transcriptase. The mixture was incubated at 42° C. for 1 hr and cooled on ice.

The 1$^{st}$ strand cDNA synthesis mixture was used as template for the PCR reaction. Specifically, the reaction mixture contained the following: 2 μl of the 1$^{st}$ strand cDNA mixture, 2 μl 5'-PCR primer (SEQ ID NO:6), 2 μl CDSIII/3'-PCR primer (SEQ ID NO:5), 80 μl water, 10 μl 10× Advantage 2 PCR buffer, 2 μl 50×dNTP mix and 2 μl 50× Advantage 2 polymerase mix. The thermocycler conditions were set for 95° C. for 20 sec, followed by 14 cycles of 95° C. for 5 sec and 68° C. for 6 min on a GenAmp 9600 instrument. PCR product was quantitated by agarose gel electro-phoresis and ethidium bromide staining.

Seventy-five μl of the above PCR products (cDNA) were mixed with 3 μl of 20 μg/μl proteinase K supplied with the kit. The mixture was incubated at 45° C. for 20 min, then 75 μl of water was added and the mixture was extracted with 150 μl phenol:chloroform:isoamyl alcohol mixture (25:24:1). The aqueous phase was further extracted with 150 μl chloroform:isoamyl alcohol (25:1). The aqueous phase was then mixed with 15 μl of 3 M sodium acetate, 2 μl of 20 μg/μl glycogen and 400 μl of 100% ethanol. The mixture was immediately centrifuged at room temperature for 20 min at 14000 rpm in a microfuge. The pellet was washed once with 150 μl of 80% ethanol, air dried and dissolved in 79 μl of water.

Dissolved cDNA was subsequently digested with SfiI (79 μl of the cDNA was mixed with 10 μl of 10× SfiI buffer, 10 μl of SfiI enzyme and 1 μl of 100× BSA and the mixture was incubated at 50° C. for 2 hrs). Xylene cyanol dye (2 μl of 1%) was added. The mixture was then fractionated on the Chroma Spin-400 column provided with the kit, following the manufacturer's procedure exactly. Fractions collected from the column were analyzed by agarose gel electrophoresis. The first three fractions containing cDNA were pooled and cDNA precipitated with ethanol. The precipitated cDNA was redissolved in 7 μl of water, and ligated into kit-supplied pDNR-LIB.

Library Sequencing

The ligation products were used to transform *E. coli* XL-1 Blue electroporation competent cells (Stratagene). An estimated total of $2\times10^6$ colonies was obtained. Sequencing of the cDNA library was carried out by Agencourt Bioscience Corporation (Beverly, Mass.), using an M13 forward primer (SEQ ID NO:7).

Example 2

Identification of a Partial LPAAT2 Sequence From *Mortierella Alpina*

The present Example describes the identification of a cDNA fragment (SEQ ID NO:8) encoding the 3' portion of the *M. alpina* LPAAT2 (provided herein as SEQ ID NOs:3 and 2), from among 9,984 cDNA sequences.

Identity of the sequence was determined by conducting BLAST (Basic Local Alignment Search Tool; Altschul, S. F., et al., *J. Mol. Biol.* 215:403–410 (1993)) searches of *M. alpina* cDNA sequences for similarity to sequences contained in the BLAST "nr" database (comprising all nonredundant GenBank CDS translations, sequences derived from the 3-dimensional structure Brookhaven Protein Data Bank, the SWISS-PROT protein sequence database, EMBL and DDBJ databases). cDNA sequences were translated in all reading frames and compared for similarity to all publicly available protein sequences contained in the "nr" database, using the BLASTX algorithm (Gish, W. and States, D. J. *Nature Genetics* 3:266–272 (1993)) provided by the NCBI. One cDNA fragment (SEQ ID NO:8) bore significant homology to a number of LPAATs and thus was tentatively identified as LPAAT2.

The results of the BLAST comparison summarizing the sequence to which SEQ ID NO:8 has the most similarity are reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance. Thus, the translated amino acid sequence of SEQ ID NO:8 had 34% identity and 72% similarity with the protein sequence of 1-acylglycerol-3-phosphate acyltransferase from *Schizosaccharomyces pombe* (GenBank Accession No. CAA22289), with an expectation value of 2e-04; additionally, the translated partial cDNA fragment had 33% identity and 55% similarity with LPAAT from *Triticum aestivum* (GenBank Accession No. MP80656).

Example 3

Sequencing of the Complete *Mortierella Alpina* LPAAT2

Analysis of the partial LPAAT2 cDNA sequence (SEQ ID NO:8) indicated that the 3'-end of the cDNA fragment extended to the end of the ORF, based on the presence of a stop codon and a polyA tail; in contrast, the 5' end was incomplete. To obtain the missing 5'-end of the cDNA, Invitrogen's 5'-end RACE kit (Catalog No. 18374-058) was utilized to enable cloning of the complete *M. alpina* LPAAT2 cDNA.

Although the manufacturer's protocol was followed for 5'-end RACE, the procedure will be briefly described below. For 1$^{st}$ strand cDNA synthesis, 1.25 μl of 20 μM MLPAT-RC-1 (SEQ ID NO:9) was mixed with 3 μl of 30.4 ng/μl *M. alpina* polyA(+)RNA from Example 1. DEPC-treated water was added to a final volume of 15.5 μl. The mixture was incubated at 70° C. for 10 min, chilled on ice for 1 min and spun briefly in an Eppendorf microfuge. The following kit reagents were then added: 2.5 μl of 10× PCR buffer, 2.5 μl of 25 mM $MgCl_2$, 2.5 μl of 0.1M DTT, 1 μl of 10 mM dNTP. The mixture was incubated for 1 min at 42° C. before the addition of 1 μl of SuperScript™ II reverse transcriptase and then the mixture was incubated (42° C. for 50 min). The reaction was terminated by incubation at 70° C. for 15 min. RNA was degraded by adding 1 μl of RNase to the above mixture, followed by a 30 min incubation at 37° C.

cDNA was purified with the kit's S.N.A.P.™ column. Specifically, 120 μl of binding solution was added to the RNase-digested cDNA sample. The mixture was transferred into the column and centrifuged at 13,000 rpm for 20 sec. The column was washed 4× with 0.4 mL each of 1× wash buffer at 4° C., followed by twice with 0.4 mL each of 70% ethanol at 4° C. For each of the wash steps, the wash solution was removed by centrifugation at 13,000 rpm for 20 sec. After the final ethanol wash, the column was centrifuged for an additional 1 min at 13,000 rpm. cDNA was collected by adding 50 μl of water heated to 65° C. to the column, and centrifuging at 13,000 rpm for 20 sec.

The purified cDNA (10 μl) was mixed with 5 μl of 5× tailing buffer, 6.5 μl of DEPC-treated water and 2.5 μl of 2 mM dCTP. The mixture was incubated at 94° C. for 3 min followed by 2 min on ice. After the addition of 1 μl of TdT (terminal deoxynucleotidyl transferase) mix, the reaction mixture was incubated for 10 min at 37° C., followed by 10 min at 65° C.

The dC-tailed cDNA (5 μl) was used as the template for 1$^{st}$ round PCR amplification of the 5' region of the cDNA. The reaction mixture also contained 2 μl of 10 μM kit primer AAP, 1 μl of 20 μM MLPAT-RC-2 (SEQ ID NO:10), 12 μl water and 25 μl of ExTaq premix 2×Taq PCR solution (TaKaRa Bio Inc., Otsu, Shiga, 520-2193, Japan). Amplification was carried out as follows: initial denaturation at 94° C. for 150 sec, followed by 30 cycles of denaturation at 94° C. for 30 sec, annealing at 55° C. for 30 sec and elongation at 72° C. for 60 sec. A final elongation cycle at 72° C. for 10 min was carried out, followed by reaction termination at 4° C. PCR product was purified using a Qiagen (Valencia, Calif.) QiaQuick PCR purification kit according to the manufacturer's protocol.

Purified 1$^{st}$ round PCR product (1 μl) was used as template for nested amplification, wherein the reaction mixture additionally contained: 1 μl of 20 μM MLPAT-RC-3 (SEQ ID NO:11), 2 μl of 10 μM kit primer AUAP, 21 μl water and 25 μl ExTaq premix 2× Taq PCR solution (supra). Amplification was performed as described above.

Agarose gel analysis showed that an ~800 bp DNA fragment was amplified. This fragment was cloned into TOPO® cloning vector pCR2.1-TOPO (Invitrogen) and sequenced. The entire cDNA sequence of the *M. alpina* LPAAT2 (SEQ ID NO:1) was obtained by combining the original partial cDNA sequence (SEQ ID NO:8) with the overlapping sequence of the 5'-RACE product. This yielded a sequence of 1086 bp, comprising: 21 bp upstream of the 'ATG' translation initiation codon of LPAAT2; the 927 bp LPAAT2 ORF (i.e., SEQ ID NO:3); and, 138 bp downstream of the LPAAT2 stop codon. The translated protein sequence (SEQ ID NO:2) had the following homology to known LPAATs, based on BLAST program analysis (supra, Example 2): 33% identity and 55% similarity with the protein sequence of LPAAT from *Brassica napus* (GenBank Accession No. CAB09138), with an expectation value of 6e-38; and, 31% identity and 51% similarity to the protein sequence of LPAAT from *Homo sapiens* (GenBank Accession No. AAH63552), with an expectation value of 7e-34.

Additionally, a protein alignment was created with the *M. alpina* LPAAT2 of the invention (SEQ ID NO:2) and the two *Mortierella alpina* sequences (GenBank Accession Nos. CAH68669 and CAH68670, corresponding to SEQ ID NOs: 17 and 19 in WO 2004/087902) previously identified as LPAATs. As shown in FIG. 2, this alignment revealed substantial differences among the three proteins.

Example 4

Generation of EPA-Producing *Yarrowia Lipolytica* ATCC #20362 Strain Y2067U

The present Example describes the construction of strain Y2067U, derived from *Yarrowia lipolytica* ATCC #20362, capable of producing significant concentrations of EPA relative to the total lipids (FIG. 3A). The affect of *M. alpina* LPAAT2 gene over-expression was examined in this EPA producing strain based on analysis of TAG content, as described in Example 5 (infra).

The development of strain Y2067U herein required the construction of strain M4 (producing 8% DGLA), strain Y2034 (producing 10% ARA), strain E (producing 10% EPA), strain EU (producing 10% EPA) and strain Y2067 (producing 15% EPA).

Construction of Strain M4 Producing 8% DGLA

Construct pKUNF12T6E (FIG. 3B; SEQ ID NO:12) was generated to integrate four chimeric genes (comprising a Δ12 desaturase, a Δ6 desaturase and 2 elongases) into the Ura3 loci of wild type *Yarrowia* strain ATCC #20362, to thereby enable production of DGLA. The pKUNF12T6E plasmid contained the following components:

TABLE 5

Description of Plasmid pKUNF12T6E (SEQ ID NO: 12)

| RE Sites And Nucleotides Within SEQ ID NO: 12 | Description Of Fragment And Chimeric Gene Components |
|---|---|
| AscI/BsiWI (9420-8629) | 784 bp 5' part of *Yarrowia* Ura3 gene (GenBank Accession No. AJ306421) |
| SphI/PacI (12128-1) | 516 bp 3' part of *Yarrowia* Ura3 gene (GenBank Accession No. AJ306421) |
| SwaI/BsiWI (6380-8629) | FBAIN::EL1S:Pex20, comprising:<br>FBAIN: FBAIN promoter (SEQ ID NO: 13; see also U.S. Patent Application No. 10/987548)<br>EL1S: codon-optimized elongase 1 gene (SEQ ID NO: 14), derived from *Mortierella alpina* (GenBank Accession No. AX464731)<br>Pex20: Pex20 terminator sequence from *Yarrowia* Pex20 gene (GenBank Accession No. AF054613) |
| BglII/SwaI (4221-6380) | TEF::Δ6S::Lip1, comprising:<br>TEF: TEF promoter (GenBank Accession No. AF054508)<br>Δ6S: codon-optimized Δ6 desaturase gene (SEQ ID NO: 16), derived from *Mortierella alpina* (GenBank Accession No. AF465281)<br>Lip1: Lip1 terminator sequence from *Yarrowia* Lip1 gene (GenBank Accession No. Z50020) |
| PmeI/ClaI (4207-1459) | FBA::F.Δ12::Lip2, comprising:<br>FBA: FBA promoter (SEQ ID NO: 18; see also U.S. Patent Application No. 10/987548)<br>F.Δ12: *Fusarium moniliforme* Δ12 desaturase gene (SEQ ID NO: 19)<br>Lip2: Lip2 terminator sequence from *Yarrowia* Lip2 gene (GenBank Accession No. AJ012632) |
| ClaI/PacI (1459-1) | TEF::EL2S::XPR, comprising:<br>TEF: TEF promoter (GenBank Accession No. AF054508)<br>EL2S: codon-optimized elongase gene (SEQ ID NO: 21), derived from *Thraustochytrium aureum* (U.S. Pat. No. 6,677,145)<br>XPR: XPR terminator sequence of *Yarrowia* Xpr gene (GenBank Accession No. M17741) |

The pKUNF12T6E plasmid was digested with AscI/SphI, and then used for transformation of wild type *Y. lipolytica* ATCC #20362 according to the General Methods. The transformant cells were plated onto FOA selection media plates and maintained at 30° C. for 2 to 3 days. The FOA resistant colonies were picked and streaked onto MM and MMU selection plates. The colonies that could grow on MMU plates but not on MM plates were selected as Ura-strains. Single colonies of Ura-strains were then inoculated into liquid MMU at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of DGLA in the transformants containing the 4 chimeric genes of pKUNF12T6E (FIG. 3B), but not in the wild type *Yarrowia* control strain. Most of the selected 32 Ura$^-$ strains produced about 6% DGLA of total lipids. There were 2 strains (i.e., strains M4 and 13-8) that produced about 8% DGLA of total lipids.

Construction of Strain Y2034 Producing About 10% ARA

Constructs pDMW232 (FIG. 3C; SEQ ID NO:23) was generated to integrate two Δ5 chimeric genes into the Leu2 gene of *Yarrowia* strain M4. The plasmid pDMW232 contained the following components:

TABLE 6

Description of Plasmid pDMW232 (SEQ ID NO: 23)

| RE Sites And Nucleotides Within SEQ ID NO: 23 | Description Of Fragment And Chimeric Gene Components |
|---|---|
| AscI/BsiWI (5550-4755) | 788 bp 5' part of *Yarrowia* Leu2 gene (GenBank Accession No. AF260230) |
| SphI/PacI (8258-8967) | 703 bp 3' part of *Yarrowia* Leu2 gene (GenBank Accession No. AF260230) |
| SwaI/BsiWI (2114-4755) | FBAIN::MAΔ5::Pex20, comprising:<br>FBAIN: FBAIN Promoter (SEQ ID NO: 13; see also U.S. Patent Application No. 10/987548)<br>MAΔ5: *Mortierella alpina* Δ5 desaturase gene (SEQ ID NO: 24) (GenBank Accession No. AF067654)<br>Pex20: Pex20 terminator sequence of *Yarrowia* Pex20 gene (GenBank Accession No. AF054613) |
| SwaI/ClaI (2114-17) | TEF::MAΔ5::Lip1, comprising:<br>TEF: TEF promoter (GenBank Accession No. AF054508)<br>MAΔ5: as described for FBAIN::MAΔ5::Pex20 (supra)<br>Lip1: Lip1 terminator sequence of *Yarrowia* Lip1 gene (GenBank Accession No. Z50020) |
| PmeI/ClaI (5550-4755) | *Yarrowia* Ura3 gene (GenBank Accession No. AJ306421) |

Plasmid pDMW232 was digested with AscI/SphI, and then used to transform strain M4 according to the General Methods. Following transformation, the cells were plated onto MMLe plates and maintained at 30° C. for 2 to 3 days. The individual colonies grown on MMLe plates from each transformation were picked and streaked onto MM and MMLe plates. Those colonies that could grow on MMLe plates but not on MM plates were selected as Leu2$^-$ strains. Single colonies of Leu2$^-$ strains were then inoculated into liquid MMLe media at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of ARA in pDMW232 transformants, but not in the parental M4 strain. Specifically, among the 48 selected Leu2$^-$ transformants with pDMW232, there were 34 strains that produced less than 5% ARA, 11 strains that produced 6–8% ARA, and 3 strains that produced about 10% ARA of total lipids in the engineered *Yarrowia*. One of the strains that produced 10% ARA was named "Y2034".

Construction of Strain E, Producing About 10% EPA

Construct pZP3L37 (FIG. 3D; SEQ ID NO:26) was created to integrate three synthetic Δ17 desaturase chimeric genes into the acyl-CoA oxidase 3 (i.e., POX3) gene of the Y2034 strain. The plasmid pZP3L37 contained the following components:

TABLE 7

Description of Plasmid pZP3L37 (SEQ ID NO: 26)

| RE Sites And Nucleotides Within SEQ ID NO: 26 | Description Of Fragment And Chimeric Gene Components |
|---|---|
| AscI/BsiWI (6813-6043) | 763 bp 5' part of *Yarrowia* Pox3 gene (GenBank Accession No. AJ001301) |
| SphI/PacI (9521-10345) | 818 bp 3' part of *Yarrowia* Pox3 gene (GenBank Accession No. AJ001301) |
| ClaI/BsiWI (4233-6043) | TEF::Δ17S::Pex20, comprising: TEF: TEF promoter (GenBank Accession No. AF054508) Δ17S: codon-optimized Δ17 desaturase gene (SEQ ID NO: 27), derived from *S. diclina* (US 2003/0196217 A1) Pex20: Pex20 terminator sequence of *Yarrowia* Pex20 gene (GenBank Accession No. AF054613) |
| ClaI/PmeI (4233-1811) | FBAIN::Δ17S::Lip2, comprising: FBAIN: FBAIN promoter (SEQ ID NO: 13; see also U.S. Patent Application No. 10/987548) Δ17S: SEQ ID NO: 27 (supra) Lip2: Lip2 terminator sequence of *Yarrowia* Lip2 gene (GenBank Accession No. AJ012632) |
| PmeI/SwaI (1811-1) | *Yarrowia* Leu2 gene (GenBank Accession No. AF260230) |
| PacI/SwaI (10345-1) | FBAINm::Δ17S::Pex16, comprising: FBAINm: FBAINm promoter (SEQ ID NO: 29; see also U.S. Patent Application No. 10/987548) Δ17S: SEQ ID NO: 27 (supra) Pex16: Pex16 terminator sequence of *Yarrowia* Pex16 gene (GenBank Accession No. U75433) |

Plasmid pZP3L37 was digested with AscI/SphI, and then used to transform strain Y2034 according to the General Methods. Following transformation, the cells were plated onto MM plates and maintained at 30° C. for 2 to 3 days. A total of 48 transformants grown on the MM plates were picked and re-streaked onto fresh MM plates. Once grown, these strains were individually inoculated into liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EPA in most of the transformants with pZP3L37, but not in the parental strain (i.e., Y2034). Among the 48 selected transformants with pZP3L37, there were 18 strains that produced less than 2% EPA, 14 strains that produced 2–3% EPA, and 1 strain that produced about 7% EPA of total lipids in the engineered *Yarrowia*.

The strain that produced 7% EPA was further analyzed after culturing the strain as follows ("two-stage growth conditions"). First, cells were grown in triplicate in liquid MM at 30° C. with shaking at 250 rpm/min for 48 hrs. The cells were collected by centrifugation and the liquid supernatant was extracted. The pelleted cells were resuspended in HGM and grown for 72 hrs at 30° C. with shaking at 250 rpm/min. The cells were again collected by centrifugation and the liquid supernatant was extracted.

GC analyses showed that the engineered strain produced about 10% EPA of total lipids after the two-stage growth. The strain was designated as the "E" strain.

Construction of Strain EU Producinq About 10% EPA

Strain EU (Ura$^-$) was created by identifying mutant cells of strain E that were 5-FOA resistant. Specifically, one loop of *Yarrowia* E strain cells were inoculated into 3 mL YPD medium and grown at 30° C. with shaking at 250 rpm for 24 hrs. The culture with diluted with YPD to an $OD_{600}$ of 0.4 and then incubated for an additional 4 hrs. The culture was plated (100 μl/plate) onto FOA selection plates and maintained at 30° C. for 2 to 3 days. A total of 16 FOA resistant colonies were picked and streaked onto MM and FOA selection plates. From these, 10 colonies grew on FOA selection plates but not on MM plates and were selected as potential Ura$^-$ strains.

One of these strains was used as host for transformation with pY37/F15, comprising a chimeric GPD::*Fusarium moniliforme* Δ15::XPR2 gene and a Ura3 gene as a-selection marker (FIG. 4A; SEQ ID NO:30). After three days of selection on MM plates, hundreds of colonies had grown on the plates and there was no colony growth of the transformation control that carried no plasmid. This 5-FOA resistant strain was designated as strain "EU".

Single colonies of the EU strain were then inoculated into liquid MMU additionally containing 0.1 g/L uridine and cultured for 2 days at 30° C. with shaking at 250 rpm/min. The cells were collected by centrifugation, lipids were extracted, and fatty acid methyl esters were prepared by trans-esterification and subsequently analyzed with a Hewlett-Packard 6890 GC. GC analyses showed that the EU strain produced about 10% EPA of total lipids.

Construction of Strain Y2067 Producing About 15% EPA

Figures 4B, 4C:
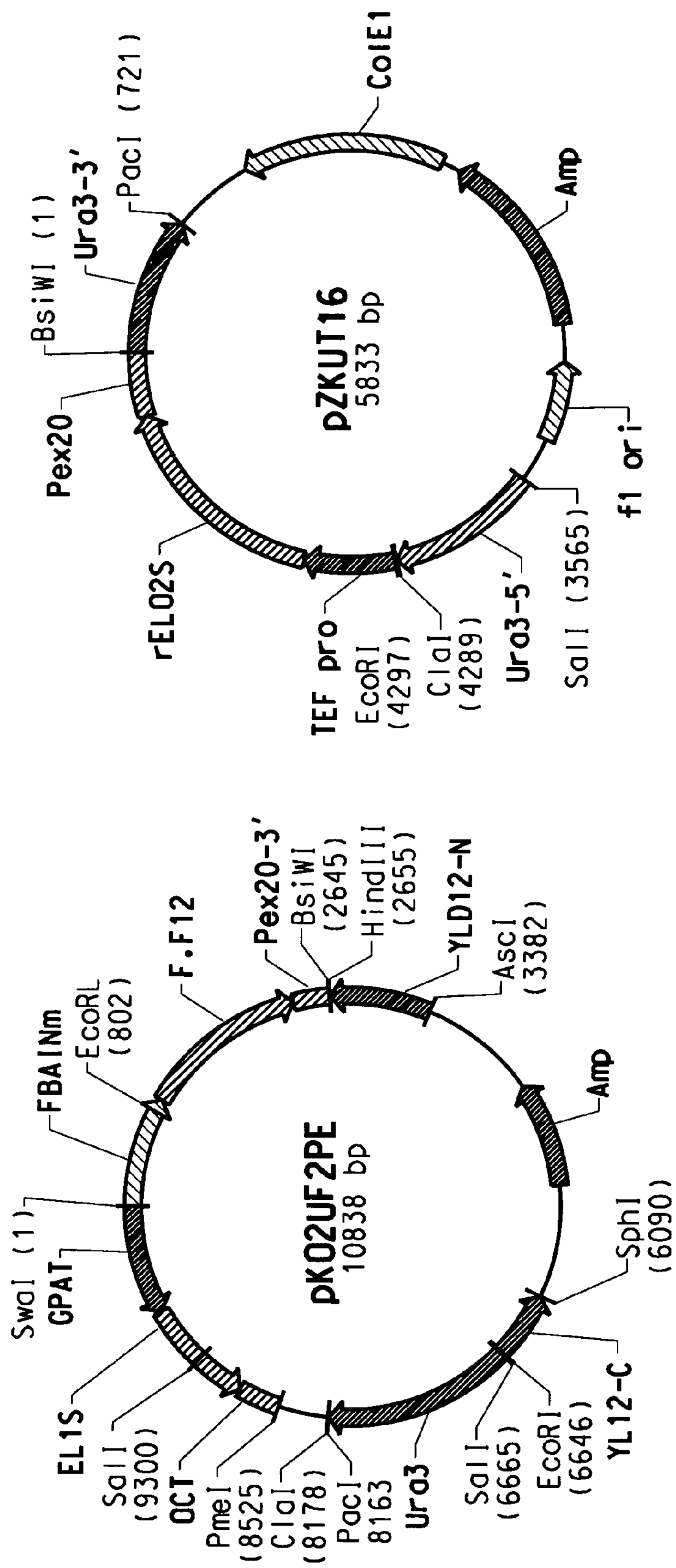

Plasmid pKO2UF2PE (FIG. 4B; SEQ ID NO:31) was created to integrate a cluster containing two chimeric genes (comprising a heterologous Δ12 desaturase and an elongase) and a Ura3 gene into the native *Yarrowia* Δ12 desaturase gene of strain EU (supra). Plasmid pKO2UF2PE contained the following components:

TABLE 8

Description of Plasmid pKO2UF2PE (SEQ ID NO: 31)

| RE Sites And Nucleotides Within SEQ ID NO: 31 | Description Of Fragment And Chimeric Gene Components |
|---|---|
| AscI/BsiWI (3382-2645) | 730 bp 5' part of *Yarrowia* Δ12 desaturase gene (SEQ ID NO: 32) |
| SphI/EcoRI (6090-6646) | 556 bp 3' part of *Yarrowia* Δ12 desaturase gene (SEQ ID NO: 32) |
| SwaI/BsiWI/ (1-2645) | FBAINm::F.Δ12DS::Pex20, comprising: FBAINm: FBAINm promoter (SEQ ID NO: 29; see also U.S. Patent Application No. 10/987548) F.Δ12: *Fusarium moniliforme* Δ12 desaturase gene (SEQ ID NO: 19) Pex20: Pex20 terminator sequence of *Yarrowia* Pex20 gene (GenBank Accession No. AF054613) |
| SwaI/PmeI (1-8525) | GPAT::EL1S::OCT, comprising: GPAT: GPAT promoter (SEQ ID NO: 34; see also U.S. Patent Application No. 60/610060) EL1S: codon-optimized elongase 1 gene (SEQ ID NO: 14), derived from *Mortierella alpina* (GenBank Accession No. AX464731) OCT: OCT terminator sequence of *Yarrowia* OCT gene (GenBank Accession No. X69988) |
| EcoRI/PacI (6646-8163) | *Yarrowia* Ura3 gene (GenBank Accession No. AJ306421) |

Plasmid pKO2UF2PE was digested with AscI/SphI and then used to transform strain EU according to the General Methods (although strain EU was streaked onto a YPD plate and grown for approximately 36 hr prior to suspension in transformation buffer [versus 18 hrs]). Following transformation, cells were plated onto MM plates and maintained at 30° C. for 2 to 3 days. A total of 72 transformants grown on MM plates were picked and re-streaked separately onto fresh MM plates. Once grown, these strains were individually inoculated into liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed the presence of EPA in almost all of the transformants with pKO2UF2PE. More specifically, among the 72 selected transformants, there were 17 strains that produced 8–9.9% EPA, 27 strains that produced 10–10.9% EPA, 16 strains that produced 11–11.9% EPA, and 7 strains that produced 12–12.7% EPA of total lipids in the engineered *Yarrowia*. The strain that produced 12.7% EPA was further analyzed by using two-stage growth conditions. GC analyses showed that the engineered strain produced about 15% EPA of total lipids after the two-stage growth. The strain was designated as strain "Y2067".

Construction of Strain Y2067U Producing About 14% EPA with Ura-Phenotype

In order to disrupt the Ura3 gene in Y2067 strain, construct pZKUT16 (FIG. 4C; SEQ ID NO:35) was created to integrate a TEF::rELO2S::Pex20 chimeric gene into the Ura3 gene of strain Y2067. rELO2S is a codon-optimized rELO gene encoding a rat hepatic enzyme that elongates 16:0 to 18:0. The plasmid pZKUT16 contained the following components:

TABLE 9

Description of Plasmid pZKUT16 (SEQ ID NO: 35)

| RE Sites And Nucleotides Within SEQ ID NO: 35 | Description Of Fragment And Chimeric Gene Components |
|---|---|
| BsiWI/PacI (1-721) | 721 bp 5' part of *Yarrowia* Ura3 gene (GenBank Accession No. AJ306421) |
| SalI/ClaI (3565-4289) | 724 bp 3' part of *Yarrowia* Ura3 gene (GenBank Accession No. AJ306421) |
| ClaI/BsiWI (4289-1) | TEF::rELO2S::Pex20, comprising: TEF: TEF Promoter (GenBank Accession No. AF054508) rELO2S: codon-optimized rELO2 elongase gene (SEQ ID NO: 36), derived from rat (GenBank Accession No. AB071986) Pex 20: Pex20 terminator sequence of *Yarrowia* Pex20 gene (GenBank Accession No. AF054613) |

The plasmid pZKUT16 was digested with SalI/PacI, and then used to transform Y2067 strain according to the General Methods. Following transformation, cells were plated onto FOA selection plates and maintained at 30° C. for 2 to 3 days.

A total of 24 transformants grown on FOA plates were picked and re-streaked onto MM plates and FOA plates, separately. The strains that could grow on FOA plates, but not on MM plates, were selected as Ura-strains. A total of 10 Ura-strains were individually inoculated into liquid MMU media at 30° C. and grown with shaking at 250 rpm/min for 1 day. The cells were collected by centrifugation, lipids were extracted, and fatty acid methyl esters were prepared by trans-esterification, and subsequently analyzed with a Hewlett-Packard 6890 GC.

GC analyses showed the presence of 5 to 7% EPA in all of the transformants with pZKUT16 after one day growth in MMU media. The strain that produced 6.2% EPA was further analyzed using two-stage growth conditions (48 hrs MM+96 hrs in HGM). GC analyses showed that the engineered strain produced about 14% EPA of total lipids. The strain was designated as strain "Y2067U". The final genotype of this strain with respect to wildtype *Yarrowia lipolytica* ATCC #20362 was as follows: Ura3-, Pox3-, Y.Δ12-, FBA::F.Δ12::Lip2, FBAlNm::F. Δ12::Pex20, TEF::Δ6S::Lip1, FBAlN::EIS::Pex20; GPAT::E1S:: Oct, TEF1::E2S::Xpr; FBAlN::MAΔ5::Pex20, TEF::MAΔ5::Lip 1, FBAlN::Δ17S::Lip2, FBAlNm::Δ17S::Pex16, TEF::Δ17S::Pex20 and TEF::rELO2S::Pex20.

Example 5

Heterologous Expression of the *Mortierella Alpina* LPAAT2 in *Yarrowia Lipolytica*

The present Example describes the over-expression of the *M. alpina* LPAAT2 ORF in a chimeric gene under the control of a *Yarrowia lipolytica* promoter in *Y. lipolytica* strain Y2067U, and the effect of the over-expression as determined by an analysis of TAG content.

Figures 5A, 5B:
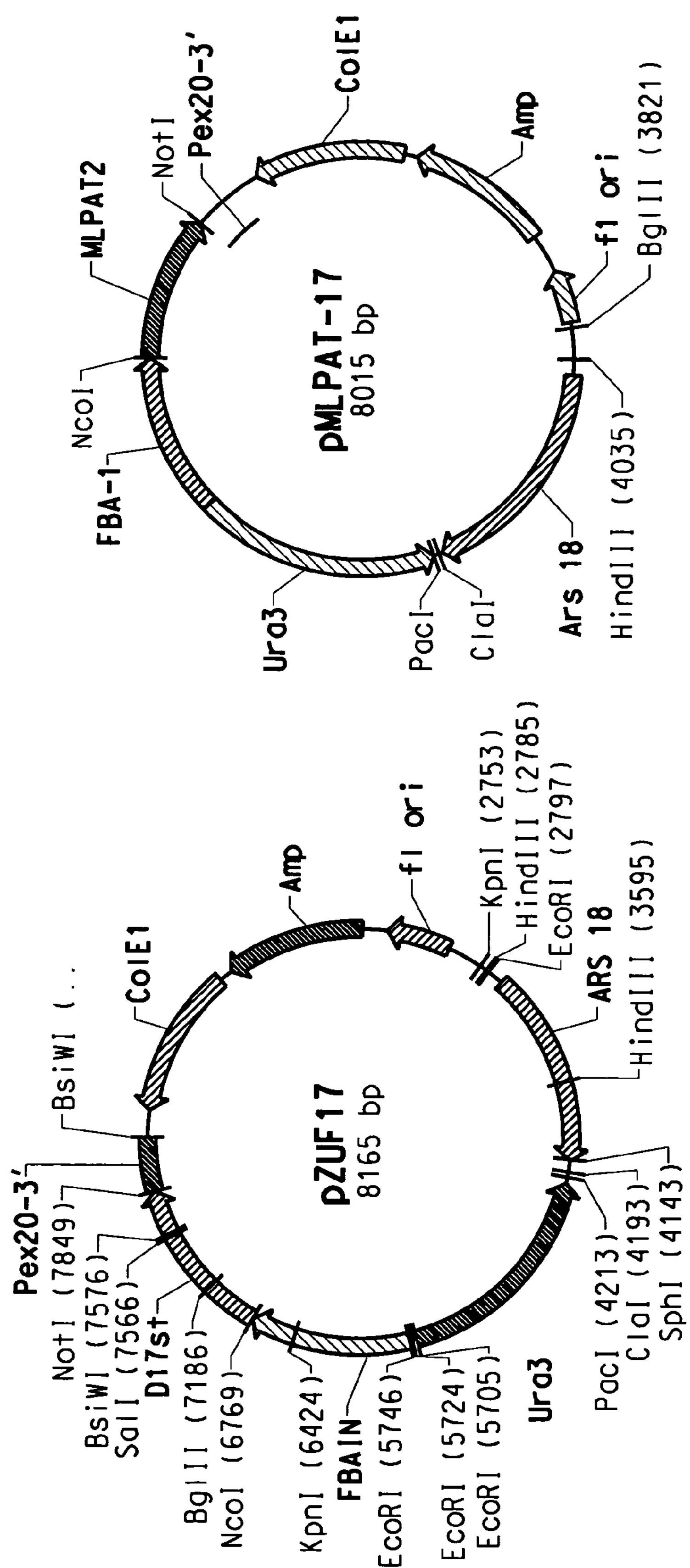

Construction of Plasmid pMLPAT-17, Comprising a FBAlN::LPAAT2::PEX20-3' Chimeric Gene The *M. alpina* LPAAT2 ORF was cloned as follows. Primers MLPAT-F and MLPAT-R (SEQ ID NOs:38 and 39) were used to amplify the LPAAT2 ORF from the cDNA of *M. alpina* (Example 1) by PCR. The reaction mixture contained 1 μl of the cDNA, 1 μl each of the primers, 22 μl water and 25 μl ExTaq premix 2× Taq PCR solution (TaKaRa Bio Inc., Otsu, Shiga, 520-2193, Japan). Amplification was carried out as follows: initial denaturation at 94° C. for 150 sec, followed by 30 cycles of denaturation at 94° C. for 30 sec, annealing at 55° C. for 30 sec and elongation at 72° C. for 90 sec. A final elongation cycle at 72° C. for 10 min was carried out, followed by reaction termination at 4° C. An ~950 bp DNA fragment was obtained from the PCR reaction. It was purified using a Qiagen (Valencia, Calif.) PCR purification kit according to the manufacturer's protocol. The purified PCR product was digested with NcoI and NotI, and cloned into Nco I-Not I cut pZUF17 vector (SEQ ID NO:40; FIG. 5A), such that the gene was under the control of the *Y. lipolytica* FBAlN promoter and the PEX20-3' terminator region in the auto-replicating vector for expression in *Y. lipolytica*. Correct transformants were confirmed by miniprep analysis and the resultant plasmid was designated as "pMLPAT-17" (SEQ ID NO:41; FIG. 5B).

Construction of Integration Plasmid pMLPAT-Int

To integrate the *M. alpina* LPAAT2 into the genome of *Yarrowia lipolytica*, plasmid pMLPAT-Int was created. Primers LPAT-Re-5-1 and LPAT-Re-5-2 (SEQ ID NOs:42 and 43) were used to amplify a 1129 bp DNA fragment, YLPAT-5' (SEQ ID NO:44), containing a 1103 bp fragment of *Y. lipolytica* genome immediately upstream of the 'AUG' of the *Y. lipolytica* LPAAT1 (SEQ ID NO:45). The reaction mixture contained 1 μl of *Y. lipolytica* genomic DNA, 1 μl each of the primers, 22 μl water and 25 μl ExTaq premix 2×Taq PCR solution (TaKaRa). Amplification was carried out as described above. An ~1130 bp DNA fragment was obtained from the PCR reaction. It was purified using Qiagen's PCR purification kit according to the manufacturer's protocol. The purified PCR product was digested with SalI and ClaI, and cloned into SalI-ClaI cut pBluescript SK(−) vector, resulting in plasmid "pYLPAT-5'".

Primers LPAT-Re-3-1 and LPAT-Re-3-2 (SEQ ID NOs:49 and 50) were then used to amplify a 938 bp fragment, YLPAT-3' (SEQ ID NO:51), containing a 903 bp fragment of

*Y. lipolytica* genome immediately after the stop codon of *Y. lipolytica* LPAAT1, using the same conditions as above. The purified PCR product was digested with ClaI and XhoI, and cloned into ClaI-XhoI digested pYLPAT-5'. Correct transformants were confirmed by miniprep analysis and the resultant plasmid was designated "pYLPAT-5'-3'".

pMLPAT-17 (SEQ ID NO:41; supra) was then digested with ClaI and NotI, and a ~3.5 kb fragment containing the *Y. lipolytica* URA3 gene, the *Y. lipolytica* FBAIN promoter and the *M. alpina* LPAAT2 gene was isolated using a Qiagen QiaexII gel purification kit according to the manufacturer's protocol. This fragment was cloned into ClaI-NotI digested pYLPAT-5'-3'. Correct transformants were confirmed by miniprep and restriction analysis. The resulting plasmid was named "pMLPAT-Int" (SEQ ID NO:52).

Construction of "Control" Vector DZUF-MOD-1

Figure 5C:
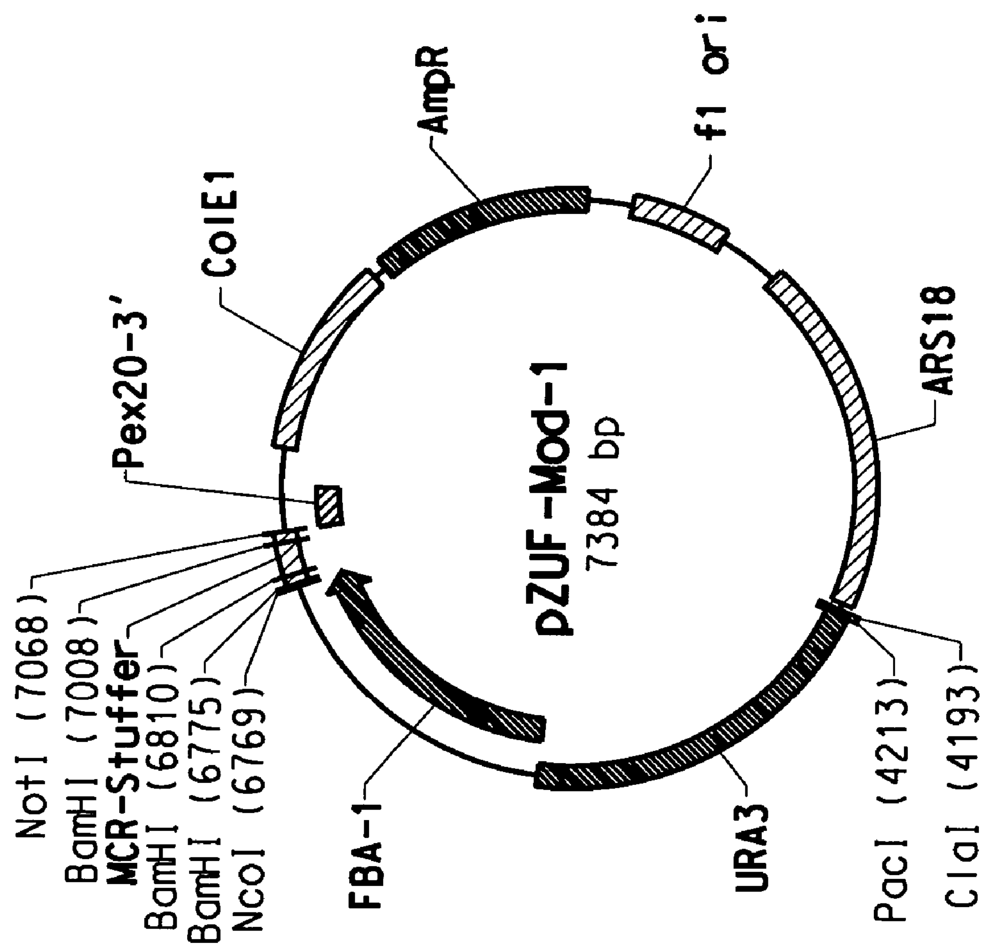

"Control" vector pZUF-MOD-1 (SEQ ID NO:53) was prepared as follows. First, primers pzuf-mod1 (SEQ ID NO:54) and pzuf-mod2 (SEQ ID NO:55) were used to amplify a 252 bp "stuffer" DNA fragment using pDNR-LIB (ClonTech, Palo Alto, Calif.) as template. The amplified fragment was purified with a Qiagen QiaQuick PCR purification kit, digested with NcoI and NotI using standard conditions, and then purified again with a QiaQuick PCR purification kit. This fragment was ligated into similarly digested NcoI-/NotI-cut pZUF17 vector (SEQ ID NO:40; FIG. 5A) and the resulting ligation mixture was used to transform *E. coli* Top 10 cells (Invitrogen). Plasmid DNA was purified from 4 resulting colonies using a Qiagen QiaPrep Spin Miniprep kit. The purified plasmids were digested with NcoI and NotI to confirm the presence of the ~250 bp fragment. The resulting plasmid was named "pZUF-MOD-1" (SEQ ID NO:53; FIG. 5C).

Analysis of Lipid Content in Transformant *Y. lipolytica* Strain Y2067U Over-Expressing *M. alpina* LPAAT2

*Y. lipolytica* strain Y2067U (from Example 4, producing 14% EPA of total lipids) was transformed with plasmid pMLPAT-17, plasmid pZUF-MOD-1 (control) and SpeI/XbaI-digested plasmid pMLPAT-Int, respectively, according to the General Methods. Transformants were grown for 2 days in synthetic MM supplemented with amino acids, followed by 4 days in HGM. The fatty acid profile of two transformants containing pZUF-MOD-1, two transformants containing pMLPAT-17, and two transformants having pMLPAT-Int integrated into the genome are shown below in the Table, based on GC analysis (as described in the General Methods). Fatty acids are identified as 18:0, 18:1 (oleic acid), 18:2 (LA), GLA, DGLA, ARA, ETA and EPA; and the composition of each is presented as a % of the total fatty acids.

TABLE 10

Lipid Content In *Yarrowia* Strain Y2067U Engineered To Over-Express *M. alpina* LPAAT2

| | Total Fatty Acids | | | | | | | |
|---|---|---|---|---|---|---|---|---|
| Strain | 18:0 | 18:1 | 18:2 | GLA | DGLA | ARA | ETA | EPA |
| Y2067U + pZUF-MOD-1 #1 | 1.1 | 4.7 | 10.9 | 19.4 | 6.3 | 0.9 | 3.9 | 13.8 |
| Y2067U + pZUF-MOD-1 #2 | 0.9 | 4.4 | 9.5 | 19.3 | 6.6 | 0.9 | 4.0 | 14.1 |
| Y2067U + pMLPAT-17 #1 | 1.0 | 4.4 | 9.8 | 18.6 | 5.9 | 0.8 | 3.4 | 15.5 |
| Y2067U + pMLPAT-17 #2 | 0.7 | 3.5 | 8.4 | 16.7 | 6.2 | 1.0 | 2.9 | 16.0 |
| Y2067U + pMLPAT-Int #1 | 1.9 | 4.9 | 13.9 | 21.1 | 4.8 | 1.1 | 2.7 | 16.6 |
| Y2067U + pMLPAT-Int #2 | 1.7 | 4.2 | 12.1 | 21.3 | 5.2 | 1.2 | 2.9 | 17.3 |

As demonstrated above, expression of the *M. alpina* LPAAT2 from pMLPAT-17 increased the EPA concentration from ~14% in the "control" strains to 15.5–16%. An additional increase in EPA to 16.6–17.3% was achieved when *M. alpina* LPAAT2 was integrated into the genome with pMLPAT-Int.

What is claimed is:

1. An isolated nucleic acid molecule, selected from the group consisting of:

(a) an isolated nucleic acid molecule encoding a lysophosphatidic acid acyltransferase enzyme having the amino acid sequence as set forth in SEQ ID NO:2;

(b) an isolated nucleic acid molecule encoding a lysophosphatidic acid acyltransferase enzyme that hybridizes with (a) under the following hybridization conditions: 0.1×SSC, 0.1% SDS, 65° C. and washed with 2×SSC, 0.1% SDS followed by 0.1×SSC, 0.1% SDS; or, an isolated nucleic acid molecule that is completely complementary to (a) or (b).

2. The isolated nucleic acid molecule of claim 1 as set forth in SEQ ID NO:3.

3. An isolated nucleic acid molecule comprising a first nucleotide sequence encoding a lysophosphatidic acid acyltransferase enzyme of at least 308 amino acids that has at least about 95% identity based on the BLAST method of alignment when compared to a polypeptide having the sequence as set forth in SEQ ID NO:2;

or a second nucleotide sequence comprising the complement of the first nucleotide sequence.

4. An isolated host cell transformed with a nucleic acid molecule comprising the nucleic acid molecule of claim 1 selected from the group consisting of algae, bacteria, fungi and yeast.

5. The transformed host cell of claim 4, wherein the yeast is an oleaginous yeast.

6. The transformed host cell of claim 5, wherein the oleaginous yeast cell is selected from the group consisting of: *Yarrowia, Candida, Rhodotorula, Rhodosporidium, Cryptococcus, Trichosporon* and *Lipomyces*.

7. The transformed host cell of claim 6, wherein the host cell is *Yarrowia lipolytica*.

* * * * *

UNITED STATES PATENT AND TRADEMARK OFFICE

CERTIFICATE OF CORRECTION

PATENT NO. : 7,189,559 B2
APPLICATION NO. : 11/251466
DATED : March 13, 2007
INVENTOR(S) : Howard Glenn Damude and Zhixiong Xue It is certified that error appears in the above-identified patent and that said Letters Patent is hereby corrected as shown below:

Column 8, line 8: change "γ-Linoleic" to --γ-Linolenic--
Column 8, line 10: change "Dihomo-γ-Linoleic" to --Dihomo-γ-Linolenic--

Signed and Sealed this

Eighteenth Day of December, 2007

JON W. DUDAS
*Director of the United States Patent and Trademark Office*